(12) United States Patent
Bishop et al.

(10) Patent No.: US 7,521,439 B2
(45) Date of Patent: *Apr. 21, 2009

(54) GLUCOCORTICOID RECEPTOR LIGANDS FOR THE TREATMENT OF METABOLIC DISORDERS

(75) Inventors: Richard D. Bishop, Grayslake, IL (US); Russell Drew Cink, Grayslake, IL (US); Bradley D. Gates, Mount Prospect, IL (US); Lars T. Hagberg, Stockholm (SE); Peer B. Jacobsen, Libertyville, IL (US); Philip R. Kym, Grayslake, IL (US); Chunqiu Lai, Libertyville, IL (US); Marvin Robert Leanna, Grayslake, IL (US); James T. Link, Evanston, IL (US); Steven J. Richards, Chicago, IL (US); Noah Tu, Singapore (SG); Tom W. von Geldern, Richmond, IL (US)

(73) Assignee: Karo Bio AB, Huddinge (SE)

( * ) Notice: Subject to any disclaimer, the term of this patent is extended or adjusted under 35 U.S.C. 154(b) by 246 days.

This patent is subject to a terminal disclaimer.

(21) Appl. No.: 11/491,337

(22) Filed: Jul. 21, 2006

(65) Prior Publication Data

US 2007/0027117 A1    Feb. 1, 2007

Related U.S. Application Data

(63) Continuation of application No. 10/460,491, filed on Jun. 12, 2003, now Pat. No. 7,141,559.

(60) Provisional application No. 60/390,056, filed on Jun. 19, 2002.

(51) Int. Cl.
*A61K 31/56*    (2006.01)
(52) U.S. Cl. .................. 514/179; 514/866; 514/909
(58) Field of Classification Search ............... 514/179
See application file for complete search history.

(56) References Cited

U.S. PATENT DOCUMENTS

| 5,462,933 A | 10/1995 | Kramer |
| 5,780,444 A | 7/1998 | Kahne |

FOREIGN PATENT DOCUMENTS

| EP | 0 489 423 A1 | 12/1991 |
| WO | WO 08/27986 | 2/1998 |
| WO | WO 99/44616 | 9/1999 |
| WO | WO 00/58337 | 5/2000 |

OTHER PUBLICATIONS

Kramer, W. and Wess, G.: European Journal of Clinical Investigation, "*Bile acid transport systems as pharmaceutical targets*", vol. 26, p. 715-732 (1996).

Kramer, Werner, et al.: The Journal of Biological Chemistry, "*Liver-specific Drug Targeting by Coupling to Bile Acids*", vol. 287, No. 26, p. 18598-18604 (1992).

*Primary Examiner*—Barbara P Badio
(74) *Attorney, Agent, or Firm*—Todd E. Garabedian; Wiggin and Dana LLP

(57) ABSTRACT

This invention relates to novel compounds that are liver selective glucocorticoid receptor antagonists, to methods of preparing such compounds, and to methods for using such compounds in the regulation of metabolism, especially lowering serum glucose levels, insulin levels, or lipid levels, and/or decreasing body weight.

12 Claims, 3 Drawing Sheets

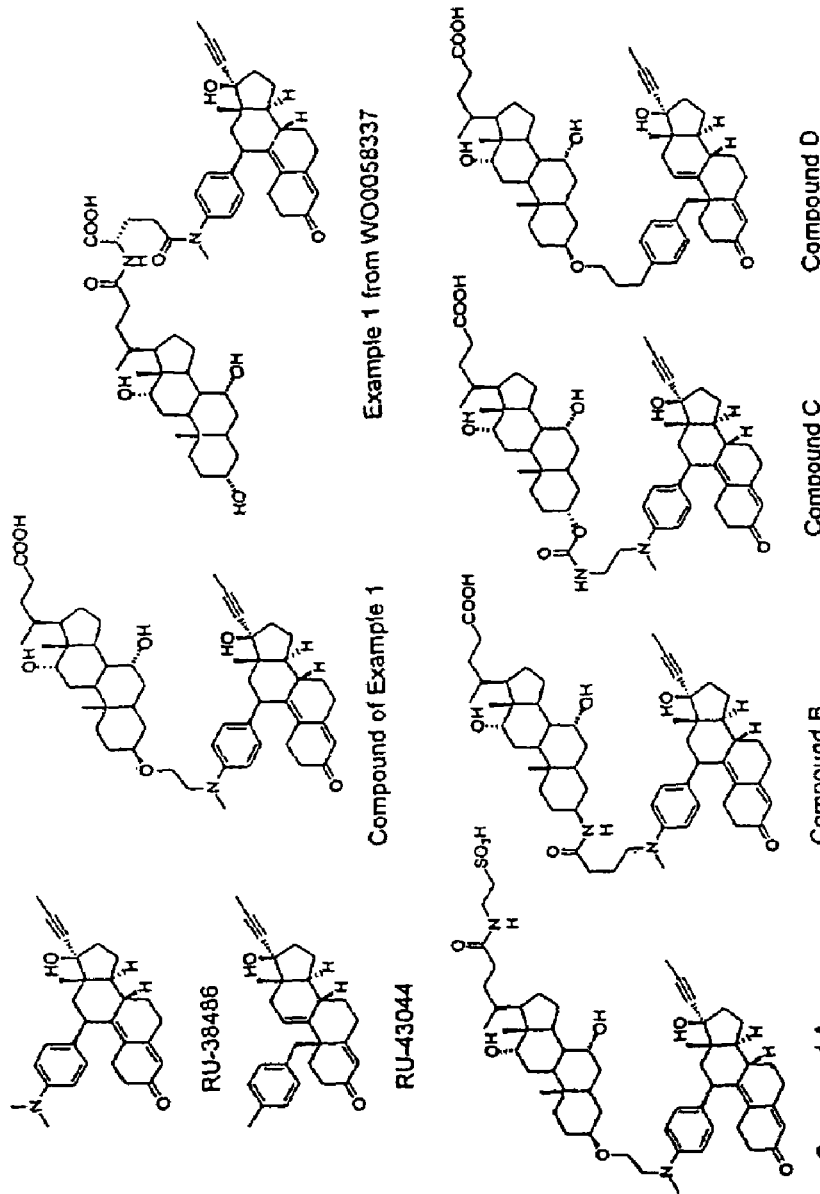
Figure 1. Representative GR antagonist-bile acid conjugates, including the compound of Example 1.

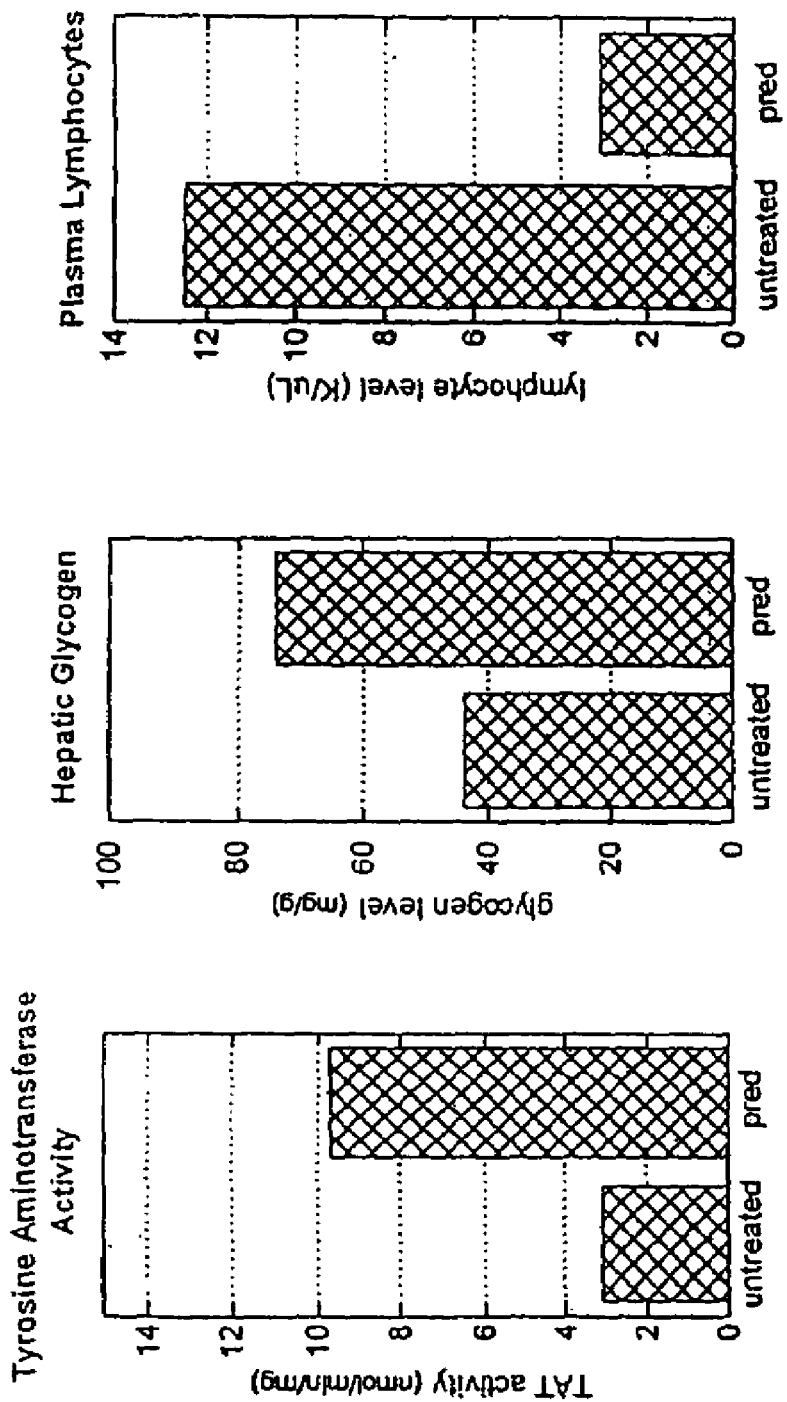
Figure 2. The effects of a 10-mpk dose of prednisolone on hepatic-(TAT, glycogen) and systemic- (lymphocyte levels) glucocorticoid-regulated responses in the rat

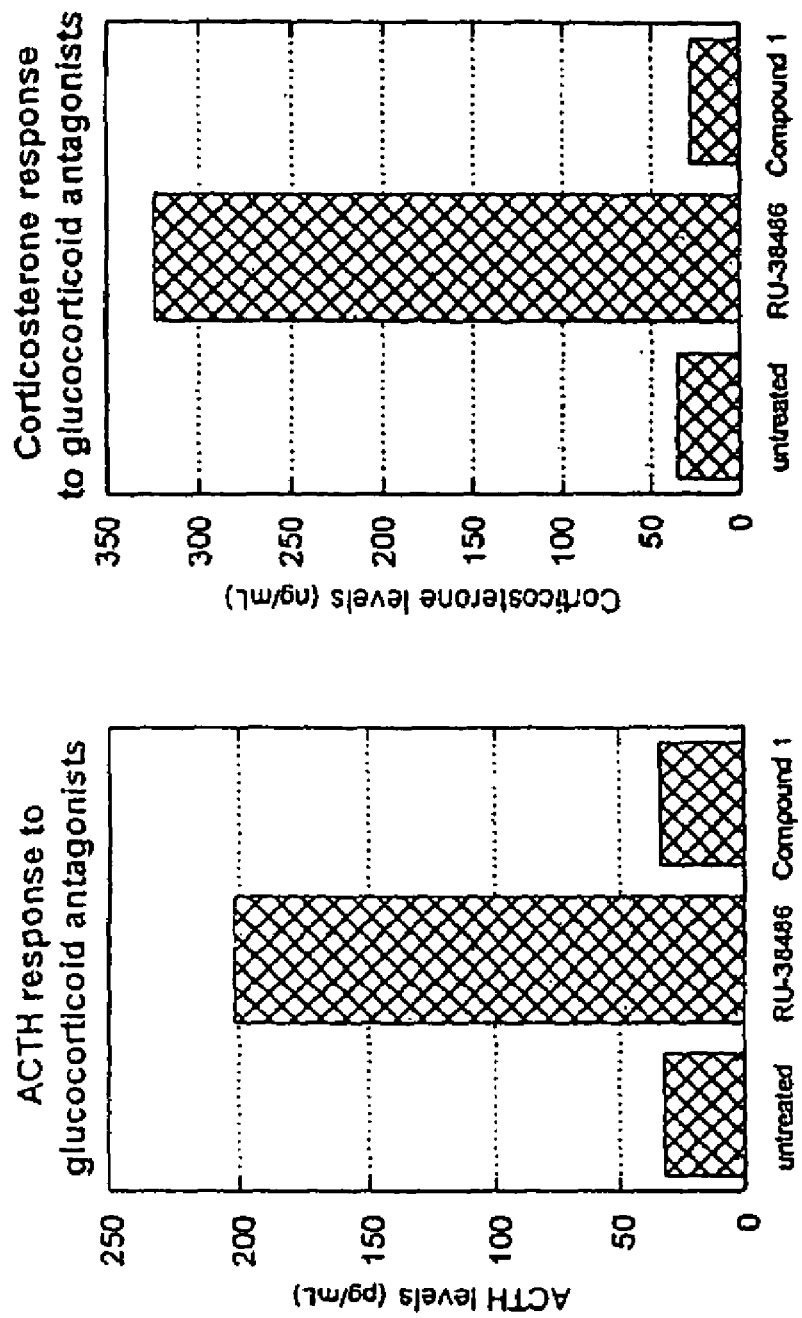
Figure 3. Effect of glucocorticoid antagonists on the hypothalamic-pituitary-adrenal (HPA) axis. Both RU-38486 and Compound 1 are given at a 100 mpk dose to normal mice; responses are measured after 1 hr.

GLUCOCORTICOID RECEPTOR LIGANDS FOR THE TREATMENT OF METABOLIC DISORDERS

This application is a Continuation of U.S. patent application Ser. No. 10/460,491, filed on Jun. 12, 2003, now U.S. Pat. No. 7,141,559, which claims the benefit of U.S. Provisional Application Ser. No. 60/390,056, filed on Jun. 19, 2002, both of which are incorporated herewith by reference.

FIELD OF INVENTION

This invention relates to novel compounds that are liver selective glucocorticoid receptor antagonists, to methods of preparing such compounds, and to methods for using such compounds in the regulation of metabolism, especially lowering serum glucose levels and/or decreasing body weight.

BACKGROUND OF THE INVENTION

A major problem with both Type 2 and Type 1 diabetes is that there is excessive and inappropriate production of glucose by the liver. This abnormality is the primary cause of fasting hyperglycemia and occurs in addition to defects in regulation of insulin release and in peripheral sensitivity to insulin. Therefore, agents that decrease liver glucose production would be beneficial for treating Type 2 and Type 1 diabetes.

Intensive treatment of the hyperglycemia of Type 1 diabetes mellitus has been shown to decrease the development of ocular, renal and neuropathic complications, and there is evidence that treatment is also beneficial for Type 2 diabetes. The available data also indicate that most patients with Type 2 or Type 1 diabetes are not receiving appropriate treatment. This inadequacy exists in spite of the availability of several different types of preparations of insulin as well as a number of other treatments which include agents that stimulate insulin release (e.g., sulfonylureas); influence liver glucose production (e.g., metformin); affect the sensitivity to insulin (e.g., troglitazone) and glucose absorption (e.g., α-glucosidase inhibitors). In spite of the availability of several different orally active agents that lower blood glucose levels, many patients with Type 2 diabetes also require insulin for control of their blood sugar levels. Overall, insulin usage in Type 2 diabetes exceeds that for Type 1 diabetes, and there is general agreement that there is a need for additional orally active agents to treat Type 2 diabetes and other obesity-related illnesses.

The glucocorticoid secretions of the adrenal gland (dominantly cortisol in humans) were so-named because of their ability to regulate glucose metabolism. These steroids stimulate the production of glucose in the liver by promoting gluconeogenesis, which is the biosynthesis of new glucose (i.e. not glucose from glycogen). Thus, in glucocorticoid insufficiency there is a tendency to hypoglycemia, with decreased liver glucose production. Further development of Addison's disease in the diabetic generally leads to lowered glucose levels. Conversely, glucocorticoid excess can provoke frank diabetes in individuals with latent diabetes mellitus, and generally aggravates glycemic control in established diabetics. Similar influences have been observed in various animal models.

The increased glucose production in response to glucocorticoids is due to effects on a number of proteins. Important among these are effects on various transaminases that convert amino acids to glucose precursors, and the induction of key gluconeogenic enzymes like glucose-6 phosphatase and phosphoenolpyruvate carboxy-kinase (PEPCK). Even a modest increase of PEPCK, as obtained in transgenic mice, gives rise to hyperglycemia. A genetic mouse model of Type 2 diabetes has increased levels of corticosterone (the endogenous glucocorticoid of that species) and concomitantly increased expression of PEPCK. This overexpression of PEPCK can be repressed by treatment with the GR antagonist RU-38486 with resulting in a decrease in the hyperglycemia. Other liver proteins are similarly regulated by glucocorticoids. For example, the hepatic enzyme tyrosine aminotransferase (TAT) is induced by treatment with the GR agonists prednisolone or dexamethasone; the elevated levels of this enzyme are normalized through treatment with RU-38486.

The considerations outlined above indicate that if the actions of endogenous glucocorticoids on liver glucose production could be blocked in a specific manner, glycemic control could be improved for the benefit of the diabetic patients. However, to date, all means to block glucocorticoid action have been systemic. These procedures result in undesirable side effects due to suppressed systemic glucocorticoid signaling. Thus, adrenalectomy leaves the patient with frank adrenal insufficiency and the problems of Addison's disease. Blockade of adrenal steroid production, for example by metyrapone, or of glucocorticoid action, for example with RU-38486, is ordinarily of limited duration of effectiveness; and when it is effective, it also results in generalized adrenal insufficiency. In the long term, compensatory ACTH hypersecretion and increased cortisol release eventually override the block and overcome these treatments. Elevated peripheral cortisol levels can trigger undesired side effects like hypokalemia. By contrast, a liver-specific GR antagonist would not have these problems, should counter-act the increased liver glucose production in diabetes mellitus and should be useful for treatment of Type 2 diabetes.

Previous efforts to block glucocorticoid action as a method for treating diabetes and obesity have been hampered by the fact that compounds used would generally block glucocorticoid action in all tissues and would lead to the potential problems of glucocorticoid insufficiency, such as hypotension, shock and ultimately death if the organism is exposed to sufficiently strong stress conditions. In contrast, a liver-selective GR-antagonist with minimal effects outside the liver could be used as a front line therapy for Type 2 diabetes, or could be used in conjunction with other existing therapies.

A liver selective GR antagonist offers a number of advantages. First, it would decrease liver glucose production. This action will have a significant effect on glycemic control. In fact, excessive liver glucose production can be the major defect in Type 2 diabetes. Secondly, such a drug should enhance insulin sensitivity because of the overall improvement in the metabolic milieu and the amelioration of the hyperglycemia-induced defects in insulin action and secretion. The decreased demand on β-cell secretion, as a result of a reduction in glycemia, would retard the progressive β-cell dysfunction characteristic of Type 2 diabetes. Another advantage that a liver selective GR antagonist would have compared to sulfonylurea or insulin treatment is that the patient would run a lower risk of hypoglycemia.

SUMMARY OF THE INVENTION

The present invention is directed to compounds of formula (I), which are useful for treating type II diabetes, obesity, Syndrome X, hyperglycemia, hypertension, inadequate glucose clearance, hyperinsulinemia, hyperlipidemia, and elevated hepatic glucocorticoid levels,

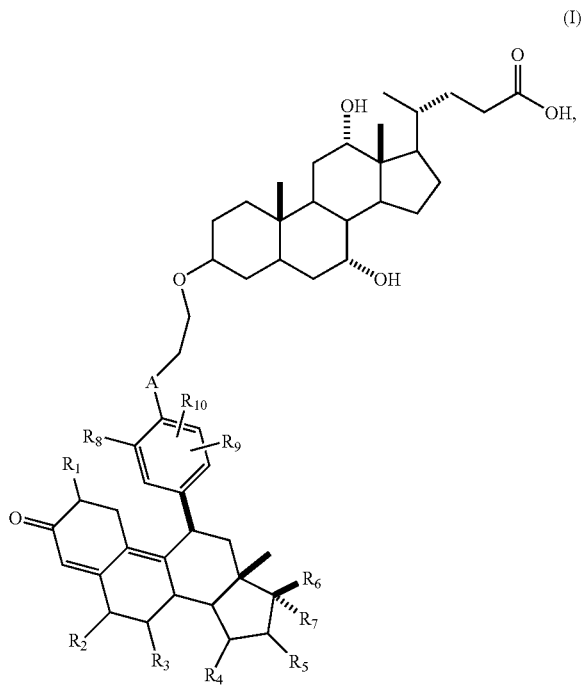

(I)

or a pharmaceutically suitable salt or prodrug thereof, wherein

A is a member selected from the group consisting of —O— or —$NR_A$— wherein $R_A$ is a member selected from the group consisting of hydrogen and alkyl;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, alkoxy, hydroxy, alkoxyalkyl, hydroxyalkyl, and halogen; and $R_8$, $R_9$ and $R_{10}$ are independently members selected from the group consisting of hydrogen, alkyl, alkenyl, alkynyl, alkoxy, hydroxy, cyano, halogen, and —$NR_B R_C$ wherein $R_B$ and $R_C$ are independently members selected from the group consisting of hydrogen and alkyl.

In another embodiment, the present invention is directed to a method of selectively antagonizing the effects of the glucocorticoid receptors in a mammal comprising administering a therapeutically effective amount of a compound of formula (I).

In another embodiment, the present invention is directed to a method of selectively antagonizing the effects of the liver glucocorticoid receptors in mammals comprising administering a therapeutically effective amount of one or more of a compound of formula (I).

In a further embodiment, the present invention is directed to a method of treating diabetes, hyperglycemia, hyperinsulinemia, inadequate glucose clearance, obesity, Syndrome X, hyperlipidemia, diabetic hypertension, and elevated hepatic glucocorticoid levels, comprising administering one or more compounds of formula (I).

In yet another embodiment, the invention is directed to pharmaceutical compositions containing compounds of formula (I).

A further embodiment of the present invention is directed to pharmaceutically suitable prodrugs of compounds of formula (I).

BRIEF DESCRIPTION OF THE DRAWINGS

The invention will be more fully understood from the following detailed description taken in conjunction with the accompanying drawing in which:

FIG. 1 is representative GR antagonist-bile acid conjugates;

FIG. 2 is bar graphs that illustrate the effects of a 10-mpk dose of prednisolone on hepatic-(TAT, glycogen) and systemic-(lymphocyte levels) glucocorticoid-regulated responses in a rat; and FIG. 3 is bar graphs showing the effect of glucocorticoid antagonists on the hypothalamic-pituitary adrenal (HPA) axis.

DETAILED DESCRIPTION OF THE INVENTION

The term "alkenyl" refers to a monovalent straight or branched chain group of two to twelve carbons derived from a hydrocarbon having at least one carbon-carbon double bond. The alkenyl groups of this invention can be optionally substituted with 1-5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "alkoxy" refers to an alkyl group attached to the parent molecular group through an oxygen atom.

The term "alkoxyalkyl" refers to an alkoxy group attached to the parent molecular group through an alkylene group.

The term "alkyl" refers to a monovalent straight or branched chain group of one to twelve carbons derived from a saturated hydrocarbon. The alkyl groups of this invention can be optionally substituted with 1-5 substitutents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "alkynyl" refers to a monovalent straight or branched chain hydrocarbon of two to twelve carbons with at least one carbon-carbon triple bond. The alkynyl groups of this invention can be optionally substituted with 1-5 substituents selected from alkoxy, alkanoyloxy, alkoxycarbonyl, amino, azido, carboxamido, carboxy, cyano, halo, hydroxy, nitro, perfluoroalkyl, perfluoroalkoxy, oxo, thioalkoxy, unsubstituted or substituted aryl, unsubstituted or substituted heteroaryl, and unsubstituted or substituted heterocycle. The substituted aryl, substituted heteroaryl, and substituted heterocycle groups substituting the alkyl groups of this invention are substituted with at least one substituent selected from alkyl, alkoxy, carboxy, azido, carboxaldehyde, halo, hydroxy, perfluoroalkyl, and perfluoroalkoxy.

The term "aryl" refers to a mono- or bicyclic carbocyclic ring system having one or two aromatic rings. The aryl group can also be fused to a cyclohexane, cyclohexene, cyclopentane, or cyclopentene ring. The aryl groups of this invention can be optionally substituted with 1-5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioakoxyalkenyl, unsubstituted or substituted aryl, unsubstituted or substituted heteroaryl, and unsubstituted or substituted heterocycle. The substituted aryl, heteroaryl, and heterocycle groups substituting the aryl groups of this invention are substituted with at least one substituent selected from alkyl, alkoxy, carboxy, azido, carboxaldehyde, halo, hydroxyl, perfluoroalkyl, and perfluoroalkoxy.

The term "cyano" refers to —CN.

The term "halo" or "halogen" refers to F, Cl, Br, or I.

The term "heterocycle" as used herein, refers to cyclic, non-aromatic, four-, five-, six-, or seven-membered rings containing at least one atom selected from the group consisting of oxygen, nitrogen, and sulfur. The four-membered rings have zero double bonds, the five-membered rings have zero or one double bonds, and the six- and seven-membered rings have zero, one, or two double bonds. Heterocycle groups of the invention are exemplified by dihydropyridinyl, morpholinyl, piperazinyl, pyrrolidinyl, tetrahydropyridinyl, piperidinyl, thiomorpholinyl, 1,3-dioxolanyl, 1,4-dioxanyl, 1,3-dioxanyl and the like. The heterocycle groups of this invention can be fused to an aryl group or a heteroaryl group. The heterocycle groups of the invention are connected to the parent molecular group through a substitutable carbon or nitrogen atom in the ring. Heterocyclyls also include bridged bicyclic groups wherein a monocyclic heterocyclic group is bridged by an alkylene group such as

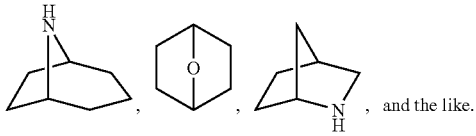

, and the like.

The heterocycle groups of this invention can be optionally substituted with 1-5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxcarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heterbaryl, and unsubstituted or substituted heterocycle. The substituted aryl, heteroaryl, and heterocycle groups substituting the heterocycle groups of this invention are substituted with at least one substituent selected from alkyl, alkoxy, carboxy, azido, carboxaldehyde, halo, hydroxyl, perfluoroalkyl, and perfluoroalkoxy.

The term "heteroaryl" as used herein, refers to cyclic, aromatic five- and six-membered groups, wherein at least one atom is selected from the group consisting of N, O and S, and the remaining atoms are carbon. The five-membered rings have two double bonds, and the six-membered rings have three double bonds. The heteroaryl groups of the invention are connected to the parent molecular group through a substitutable carbon or nitrogen in the ring. Heteroaryls are exemplified by furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of this invention can be fused to an aryl group, a heterocycle, or another heteroaryl. The heteroaryl groups of this invention can be optionally substituted with 1-5 substituents independently selected from alkyl, alkoxy, alkoxyalkyl, alkoxyalkenyl, alkanoyl, alkanoyloxy, alkanoyloxyalkyl, alkanoyloxyalkenyl, alkoxycarbonyl, alkoxycarbonylalkyl, alkoxycarbonylalkenyl, alkylsulfonyl, alkylsulfonylalkyl, alkylsulfonylalkenyl, amino, aminoalkyl, aminoalkenyl, aminosulfonyl, aminosulfonylalkyl, aminosulfonylalkenyl, azido, carboxaldehyde, (carboxaldehyde)alkyl, (carboxaldehyde)alkenyl, carboxamido, carboxamidoalkyl, carboxamidoalkenyl, carboxy, carboxyalkyl, carboxyalkenyl, cyano, cyanoalkyl, cyanoalkenyl, halo, haloalkyl, haloalkenyl, hydroxy, hydroxyalkyl, hydroxyalkenyl, nitro, oxo, perfluoroalkyl, perfluoroalkoxy, perfluoroalkoxyalkyl, perfluoroalkoxyalkenyl thioalkoxy, thioalkoxyalkyl, thioalkoxyalkenyl, unsubstituted or substituted aryl, unsubstituted or substituted heteroaryl, and unsubstituted or substituted heterocycle. The substituted aryl, heteroaryl, and heterocycle substituting the heteroaryl groups of this invention are substituted with at least one substituent selected from alkyl, alkoxy, carboxy, azido, carboxaldehyde, halo, hydroxyl, perfluoroalkyl, and perfluoroalkoxy.

The term "hydroxy" refers to —OH.

The term "hydroxyalkyl" refers to a hydroxy group attached to the parent molecule through an alkyl group.

The present invention is directed to compounds of formula (I),

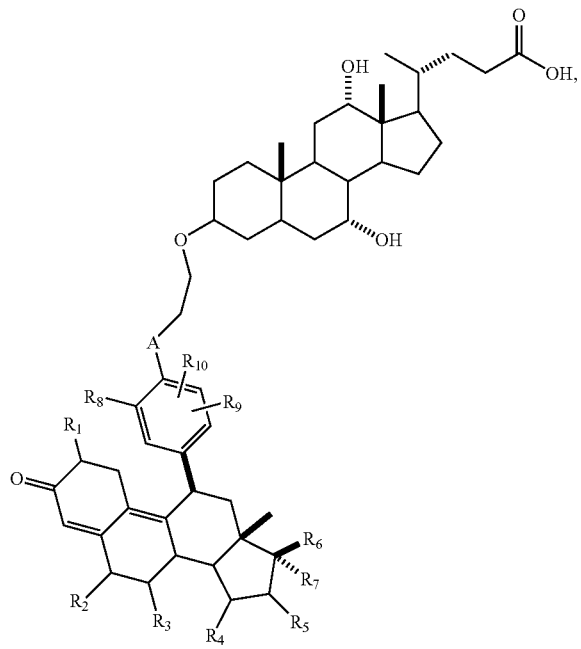

or a pharmaceutically suitable salt or prodrug thereof, wherein

A is a member selected from the group consisting of —O or —NR$_A$ wherein R$_A$ is a member selected from the group consisting of hydrogen and alkyl;

R$_1$, R$_2$, R$_3$, R$_4$, R$_5$, R$_6$ and R$_7$ are independently members selected from the group consisting of hydrogen, (C$_1$-C$_6$)-alkyl, alkenyl, alkynyl, alkoxy, hydroxy, alkoxyalkyl, hydroxyalkyl, and halogen; and $R_8$, $R_9$ and $R_{10}$ are independently members selected from the group consisting of hydrogen, alkyl, alkenyl, alkynyl, alkoxy, hydroxy, cyano, halogen, and —$NR_BR_C$ wherein $R_B$ and $R_C$ are independently members selected from the group consisting of hydrogen and alkyl.

According to one embodiment of the present invention there is provided a compound of formula (I), wherein $R_1$, $R_2$, $R_3$ and $R_4$ are hydrogen; and $R_5$ is a member selected from the group consisting of hydrogen and alkyl, and A, $R_6$, $R_7$, $R_8$, $R_9$, $R_{10}$, $R_A$, $R_B$ and $R_C$ are defined in formula (I).

In another embodiment of the present invention there is provided a compound of formula (I), wherein $R_1$, $R_2$, $R_3$, $R_4$, $R_8$, $R_9$, and $R_{10}$ are hydrogen; $R_5$ is a member selected from the group consisting of hydrogen and alkyl; $R_6$ is OH; $R_7$ is alkyne, and A, $R_8$, $R_9$, $R_{10}$ $R_A$, $R_B$ and $R_C$ are defined in formula (I).

In another embodiment of the present invention there is provided a compound of formula (I), wherein $R_1$, $R_2$, $R_3$, $R_4$, $R_8$, $R_9$, and $R_{10}$ are hydrogen; $R_5$ is a member selected from the group consisting of hydrogen and alkyl; $R_6$ is OH; $R_7$ is —C≡C—$CH_3$, and A, $R_8$, $R_9$, $R_{10}$ $R_A$, $R_B$ and $R_C$ are defined in formula (I).

In another embodiment of the present invention there is provided a compound of formula (I), wherein $R_1$, $R_2$, $R_3$, $R_4$, $R_8$, $R_9$, and $R_{10}$ are hydrogen; $R_5$ is a member selected from the group consisting of hydrogen and alkyl; $R_6$ is OH; $R_7$ is —C≡C—$CH_3$; A is —$NCH_3$, and $R_8$, $R_9$, $R_{10}$ $R_A$, $R_B$ and $R_C$ are defined in formula (I).

In another embodiment of the present invention there is provided a compound of formula (I), wherein $R_6$ is OH; $R_7$ is —C≡C—$CH_3$; A is —O—, and $R_1$, $R_2$, $R_3$, $R_4$, $R_5$, $R_8$, $R_9$, $R_{10}$ $R_A$, $R_B$ and $R_C$ are defined in formula (I).

Another embodiment of the present invention is directed to pharmaceutically suitable prodrugs of the compounds of formula (I).

In one embodiment, the present invention is directed to prodrugs that are cleaved to release a compound of formula (I) within the alimentary tract.

In another embodiment of the present invention there is provided a compound of formula (II), wherein (II)

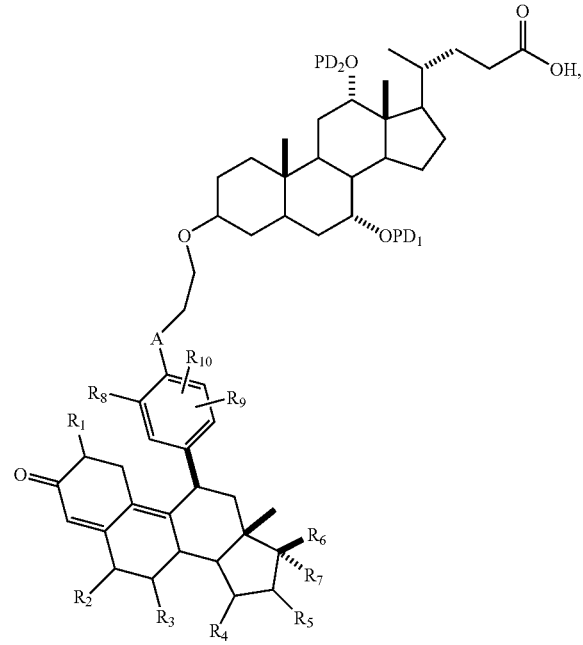

or a pharmaceutically suitable salt thereof, wherein A is a member selected from the group consisting of —O— and —$NR_A$; $R_1$, $R_2$, $R_3$, $R_4$, $R_5$, $R_6$ and $R_7$ are independently members selected from the group consisting of hydrogen ($C_1$-$C_6$)-alkyl, alkenyl, alkynyl, alkoxy, hydroxy, alkoxyalkyl, hydroxyalkyl, and halogen; $R_8$, $R_9$, $R_{10}$ are selected from the group consisting of hydrogen, alkyl, alkenyl, alkynyl, alkoxy, cyano, hydroxy, halogen and —$NR_BR_C$; $R_A$ is a member selected from the group consisting of hydrogen and alkyl; $R_B$ and $R_C$ are independently members selected from the group consisting of hydrogen and alkyl; and one or more of $PD_1$ and $PD_2$ are moieties which are cleaved in vivo in the alimentary tract.

In another embodiment of the present invention there is provided a compound of formula (II), wherein $R_1$, $R_2$, $R_3$, $R_4$, $R_8$, $R_9$, and $R_{10}$, are hydrogen; $R_5$ is a member selected from the group consisting of hydrogen and alkyl; $R_6$ is OH; $R_7$ is —C≡C—$CH_3$. In one embodiment of the present invention there is provided a method of selectively antagonizing the effects of the glucocorticoid receptors in a mammal comprising administering a therapeutically effective amount of a compound of formula (I).

In one embodiment of the present invention there is provided a method of selectively antagonizing the effects of the —$NR_A$; $R_1$, $R_2$, $R_3$, $R_4$, $R_5$, $R_6$, $R_7$ are independently members selected from the group consisting of hydrogen, ($C_1$-$C_6$)-alkyl, alkenyl, alkynyl, alkoxy, hydroxy, alkoxyalkyl, hydroxyalkyl, and halogen; $R_8$, $R_9$ and $R_{10}$ are independently members selected from the group consisting of hydrogen, alkyl, alkenyl, alkynyl, alkoxy, hydroxy, cyano, halogen, and —$NR_BR_C$; $R_A$ is a member selected from the group consisting of hydrogen and alkyl; $R_B$ and $R_C$ are selected from the group consisting of hydrogen and alkyl; and one or more of $PD_1$ and $PD_2$ are cleaved in vivo. In another embodiment of the present invention there is provided a compound of formula (II), wherein (II)

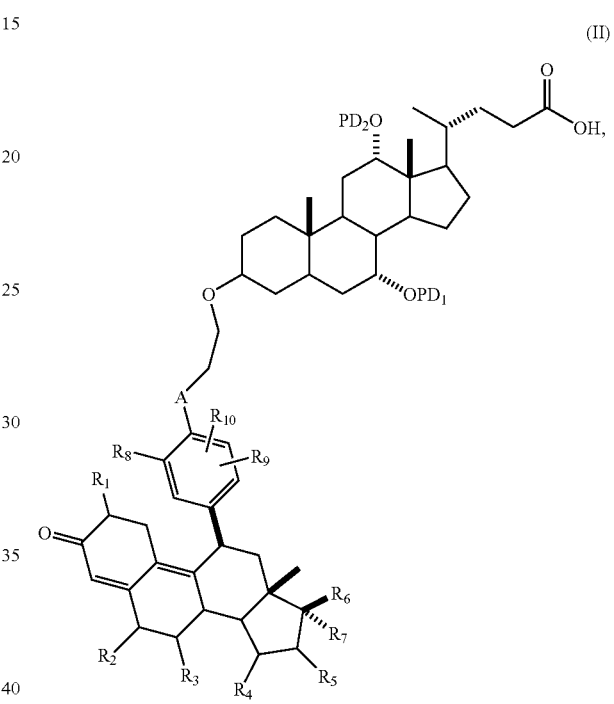

glucocorticoid receptors in a mammal comprising administering a therapeutically effective amount of a compound of formula (II).

In one embodiment of the present invention there is provided a method of selectively antagonizing the effects of the liver glucocorticoid receptors in mammals comprising administering a therapeutically effective amount of a compound of formula (I).

In one embodiment of the present invention there is provided a method of selectively antagonizing the effects of the liver glucocorticoid receptors in mammals comprising administering a therapeutically effective amount of a compound of formula (II).

In one embodiment of the present invention there is provided a method of treating diabetes, obesity, or Syndrome X in a mammal comprising administering a therapeutically effective amount of a compound of formula (I).

In one embodiment of the present invention there is provided a method of treating diabetes, obesity, or Syndrome X in a mammal comprising administering a therapeutically effective amount of a compound of formula (II).

In one embodiment of the present invention there is provided a method of treating hyperglycemia, inadequate glucose clearance, hyperinsulinemia, hyperlipidemia, diabetic hypertension, or elevated hepatic glucocorticoid levels in a mammal comprising administering a therapeutically effective amount of a compound of formula (I).

In one embodiment of the present invention there is provided a method of treating hyperglycemia, inadequate glucose clearance, hyperinsulinemia, hyperlipidemia, diabetic hypertension, or elevated hepatic glucocorticoid levels in a mammal comprising administering a therapeutically effective amount of a compound of formula (II).

In one embodiment of the present invention there is provided a pharmaceutical composition comprising a therapeutically effective amount of a compound of formula (I) in combination with a pharmaceutically suitable carrier.

In one embodiment of the present invention there is provided a pharmaceutical composition comprising a therapeutically effective amount of a compound of formula (II) in combination with a pharmaceutically suitable carrier.

In one embodiment of the present invention there is provided a process of making compounds of structural formula (1H),

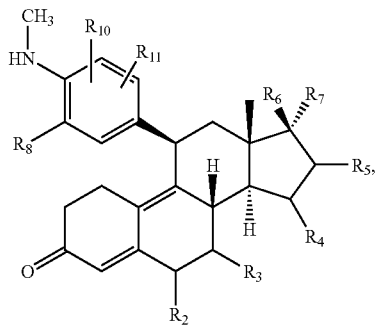
(1H)

wherein $R_2$, $R_3$, $R_4$, $R_5$, $R_6$, $R_7$, $R_8$, $R_9$, $R_{10}$ and $R_{11}$ are as defined in claim 1, comprising, in toto, the steps of: (a) treating a compound having structural formula (1T)

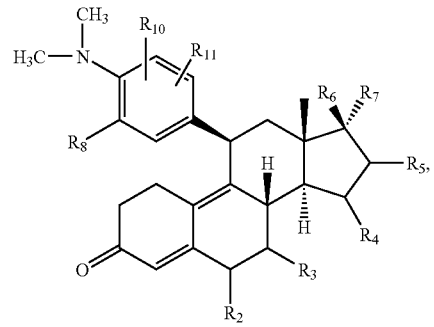
(1T)

with an oxidizing reagent to provide a compounds having structural formula (1U); and

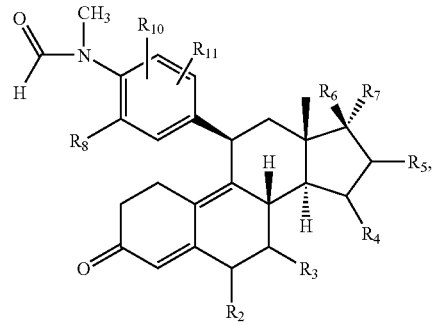
(1U)

(b) treating the compound having structural formula (1U) with dilute acid to provide the compound having structural formula (1H).

In one embodiment of the present invention there is provided a process of making compounds of structural formula (1H),

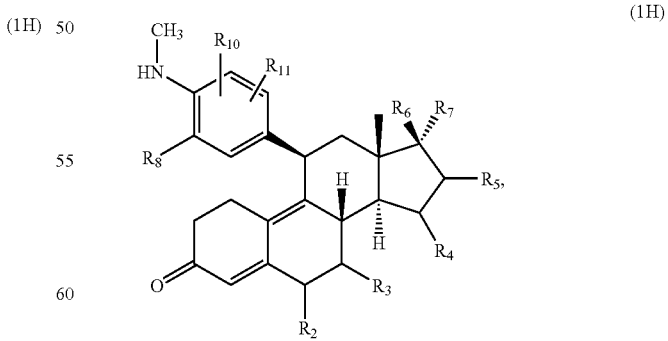
(1H)

wherein $R_2$, $R_3$, $R_4$, $R_5$, $R_6$, $R_7$, $R_8$, $R_9$, $R_{10}$ and $R_{11}$ are as defined in claim 1, comprising, in toto, the steps of: (a) treating a compound having structural formula (1T)

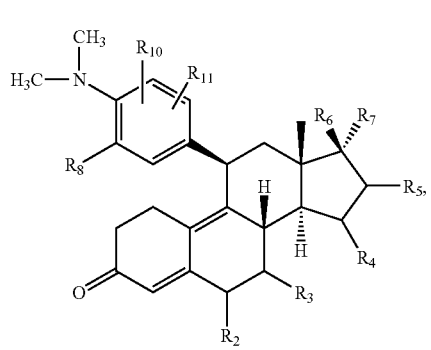

(1T)

with tetrapropylammonium perruthenate and N-methylmorpholine N-oxide to provide a compounds having structural formula (1U); and

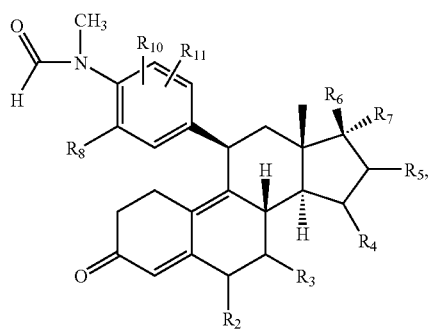

(1U)

(b) treating the compound having structural formula (1U) with dilute acid to provide the compound having structural formula (1H).

In another embodiment of the present invention there is provided a process of making compounds of structural formula (1H), comprising in toto the steps of: (a) adding N-methylmorpholine N-oxide to a solution of a compound of structural formula (1T) in dicloromethane; (b) cooling the solution to −10° C. under an atmosphere of nitrogen; (c) adding a solution of tetrapropylammonium perruthenate in dichloromethane; (d) quenching any remaining oxidizing reagents with a 10% sodium bisulfite solution; and (e) treating the formed product with a 5% hydrochloric acid solution to provide the compound having structural formula (1H).

In one embodiment of the present invention there is provided a process of making compounds of formula (Ia),

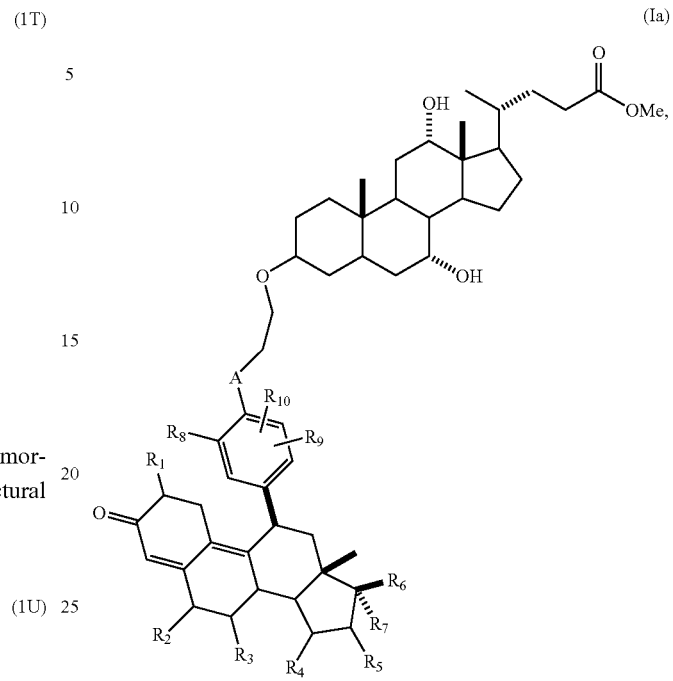

(Ia)

wherein $R_2$, $R_3$, $R_4$, $R_5$, $R_6$, $R_7$, $R_8$, $R_9$, $R_{10}$ and $R_{11}$ are as defined in claim 1, comprising, treating a compound having structural formula (1T)

(1T)

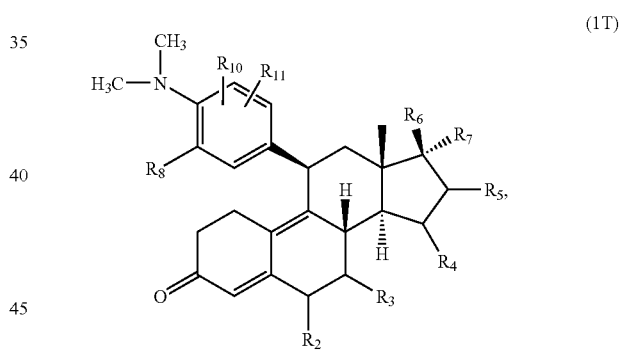

with a compound of structural formula (1M),

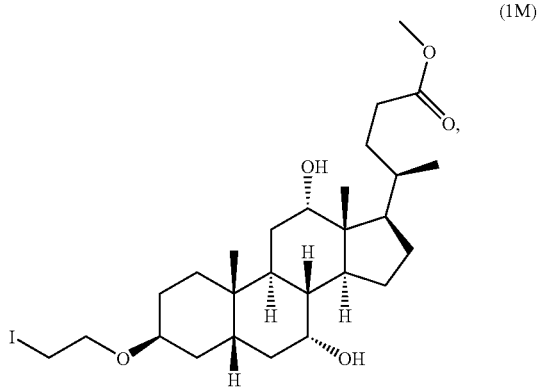

(1M)

to provide a compound of formula (Ia).

In one embodiment of the present invention there is provided a process of making compounds of formula (Ia),

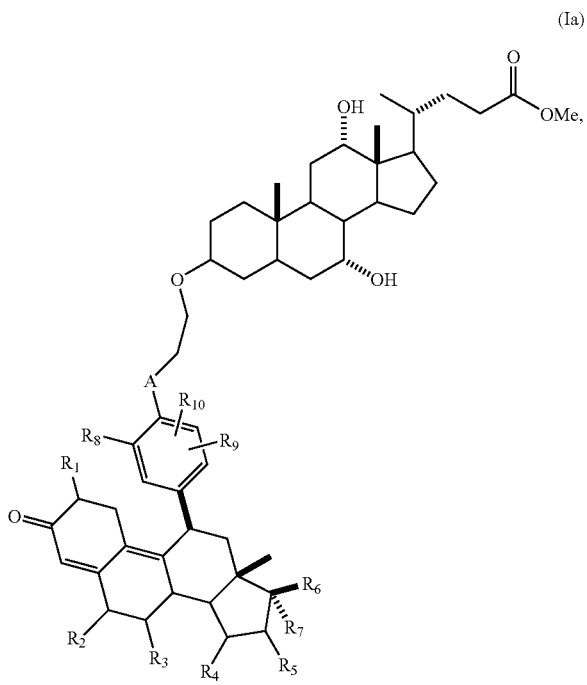

wherein $R_2$, $R_3$, $R_4$, $R_5$, $R_6$, $R_7$, $R_8$, $R_9$, $R_{10}$ and $R_{11}$ are as defined in claim 1, comprising, in toto, the steps of: (a) treating a compound having structural formula (1L)

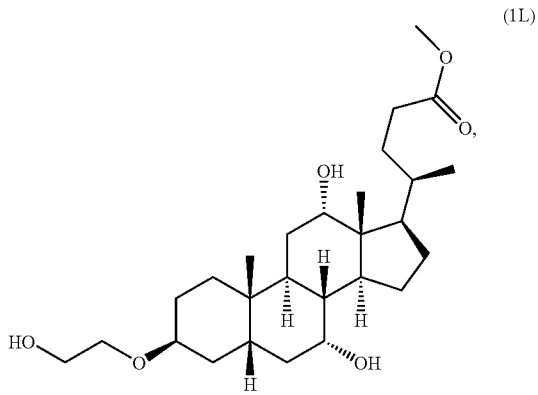

with a reagent which will activate the primary alcohol; and
(b) treating the product of step (a) with a compound having structural formula (1T),

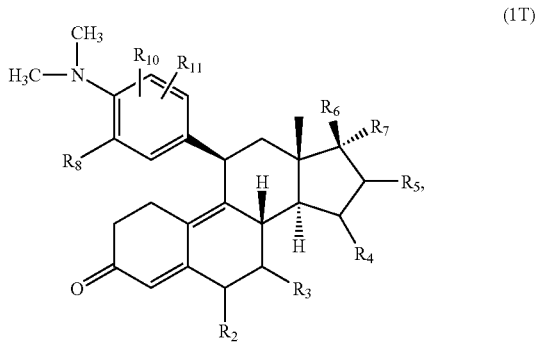

to provide a compound of formula (Ia).

The activation of the primary alcohol described in the present invention includes the transformation of the primary alcohol into a triflate, mesylate or tosylate utilizing reagents known to those skilled in the art. The term activation of the alcohol in the present invention is also intended to include the tranformation of the alcohol into a chloride, bromide or iodide or other reactive intermediate useful in the described scheme.

In one embodiment of the present invention there is provided a process of making compounds of formula (Ia),

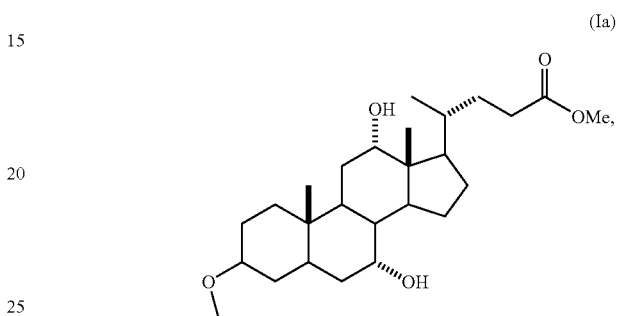

wherein $R_2$, $R_3$, $R_4$, $R_5$, $R_6$, $R_7$, $R_8$, $R_9$, $R_{10}$ and $R_{11}$ are as defined in claim 1, comprising, in toto, the steps of: (a) treating a compound having structural formula (1L)

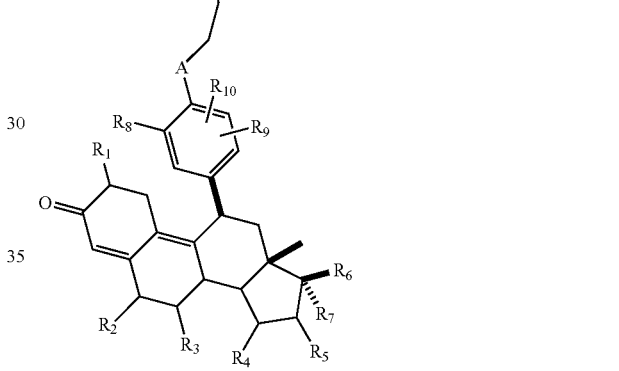

with trifluoromethanesulfonic anhydride; and
(b) treating the product of step (a) with a compound having structural formula (1T),

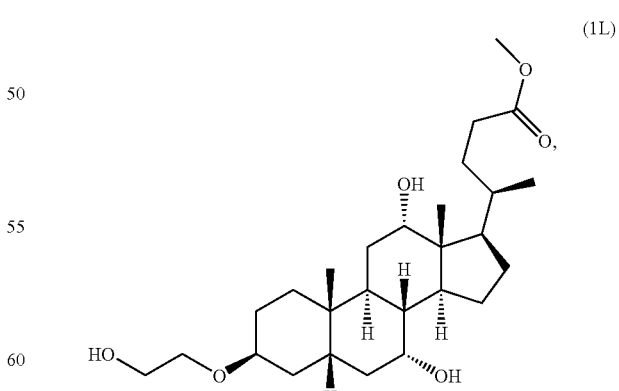

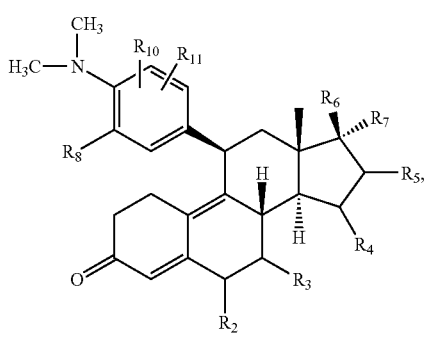

(1T)

to provide a compound of formula (Ia).

In the present invention, the term "prodrug" represents compounds that are transformed in vivo to the compound of formula (I), for example, by hydrolysis in blood or in the alimentary tract. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically suitable prodrugs" represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the various ionic forms, of the compounds of the invention. For example, ester prodrugs may be prepared according to the methods of Anderson and Taphouse, described in J. Pharm. Sci. 1981, 70, 181-186. Phosphate prodrugs may be prepared according to the methods described by Kitagawa, Mohri, and Kitagawa in Arzneim.-Forschung 1972, 22, 402-410; or by the procedures of Thaisrivongs et al. in J. Med. Chem. 1993, 36, 2575-2577. Phosphoryloxy-methyl carbonates and carbamates may be prepared according to strategies outlined by Safadi, Oliyai, and Stella in Pharm. Res. 1993, 10(9), 1350-1355. These and other prodrugs including acyloxymethyl and phosphoryloxymethyl ethers may also be prepared according to the strategies outlined by Hewawasam et al., in Bioorg. Med. Chem. Letts. 2003, 13, 1695-1698. Additional examples of water-soluble prodrugs are described by Y. Hattori, S. Kawakami, F. Yamashita, and M. Hashida in J. Controlled Release 69 (2000), 369-377, and by R. Sauer, J. Maurinsh, U. Reith, F. Fulle, K-N. Klotz, and C. Muller in J. Med. Chem. 2000, 43, 440-448, both of which are incorporated herein by example.

The term "pharmaceutically suitable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically suitable salts are well known in the art. For example, S. M. Berge, et al. describe pharmaceutically suitable salts in detail in J. Pharmaceutical Sciences, 66:1-19 (1977). The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thyocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a ring. Substituents around a carbon-carbon double bond are designated as being in the Z or E configuration where the term "Z" represents substituents on the same side of the carbon-carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substituents are disposed on both the same and opposite sides of plane of the ring are designated cis/trans.

The present invention also provides pharmaceutical compositions, which comprise compounds of the present invention formulated together with one or more non-toxic pharmaceutically suitable carriers. The pharmaceutical compositions may be specially formulated for oral administration in solid or liquid form, for parenteral injection, or for rectal administration.

The pharmaceutical compositions of the invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to mode of administration which include intravenous, intramuscular, intraperitoneal, instrasternal, subcutaneous and intraarticular injection and infusion.

Pharmaceutical compositions of this invention for parenteral injection comprise pharmaceutically suitable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically suitable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also compromise buffering agents.

Solid compositions of a similar type may also be employed as fillers in soft and hard-filled gelatin capsules using such excipients as lactose or milk sugar as well as high molecular weight polyethylene glycols and the like.

The solid dosage form of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically suitable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzonate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acids esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glyucol or suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically suitable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically suitable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.1 to about 50, more preferably of about 1 to about 10 mg of active compound per kilogram of body weight per day are administered orally to a mammalian patient. If desired, the effective daily dose may be divided into multiple doses for purposes of administration, e.g., two to four separate doses per day.

The compounds of the invention can be prepared by employing reactions shown in the Schemes below. It will be readily apparent to one of ordinary skills in the art that the compounds can be synthesized by substitution of the appropriate reactants in these syntheses, and that the steps themselves can be conducted in varying order. For example, in the schemes below, $R^1, R^2, R^3, R^4, R^5, R^8, R^9$, and $R^{10}$, whenever convenient, are hydrogen for ease of illustration only. The chemistry employed in the schemes can be conducted when these groups are other than hydrogen. It will also be apparent that protection and deprotection steps can be performed to successfully complete the syntheses of the compounds. A thorough discussion of protecting groups is provided in *Protective Groups in Organic Synthesis*, $3^{rd}$ edition, John Wiley & Sons, New York (1999).

Abbreviations that have been used in the descriptions of the scheme and the examples that follow are: DMF for N,N-dimethylformamide, DMSO for dimethylsulfoxide, HFA for hexafluoroacetone trihydrate, PPh₃ for triphenylphosphine, OsO₄ for osmium tetroxide, NaBH₄ for sodium borohydride, (iPr)₂EtN for diisopropylethylamine, NaIO₄ for sodium periodate, LiOH for lithium hydroxide, TBTU for 2-(1H-benzotriazol-1-yl)-1,1,2,2-tetramethyluroniumtetrafluoroborate, NBS for N-bromosuccinimide; and THF for tetrahydrofuran.

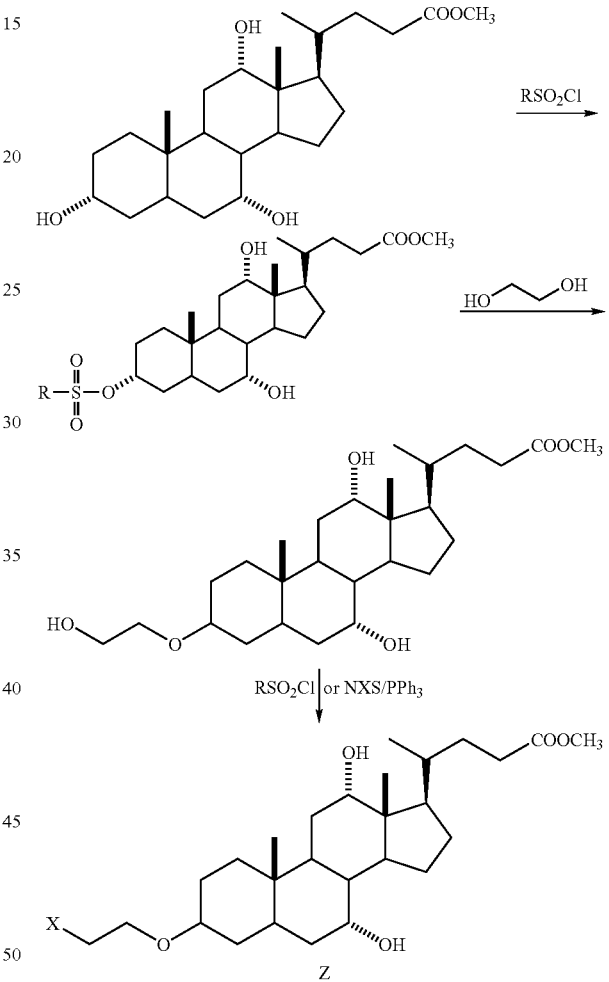

Scheme 1. Preparation of activated bile acid intermediates

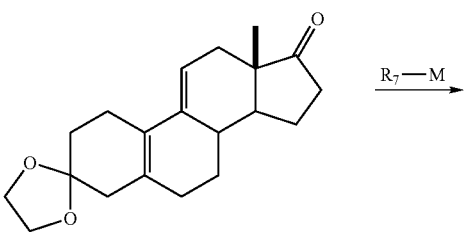

Scheme 2. Preparation of glucocorticoid antagonist intermediates

-continued
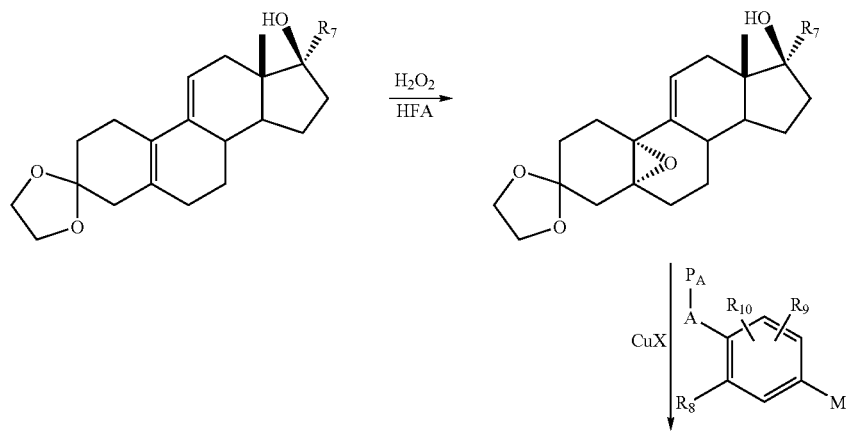
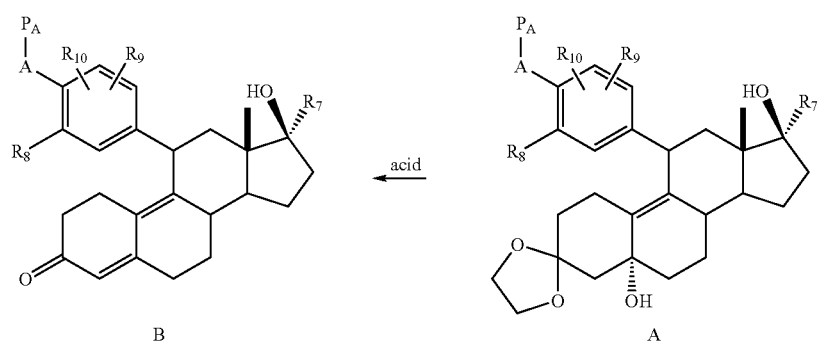
Scheme 3. Assembly of fragments
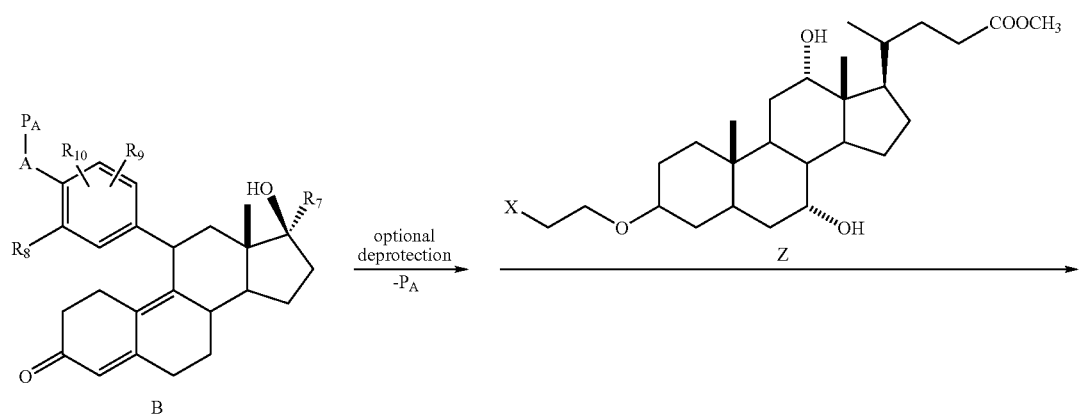

-continued

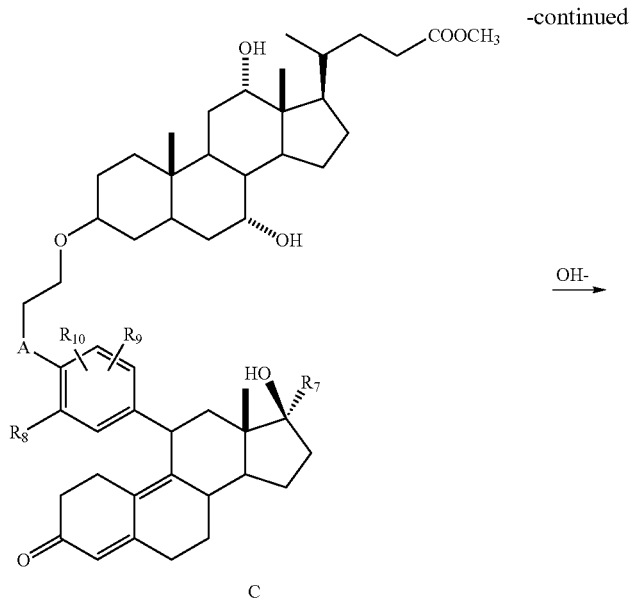

C

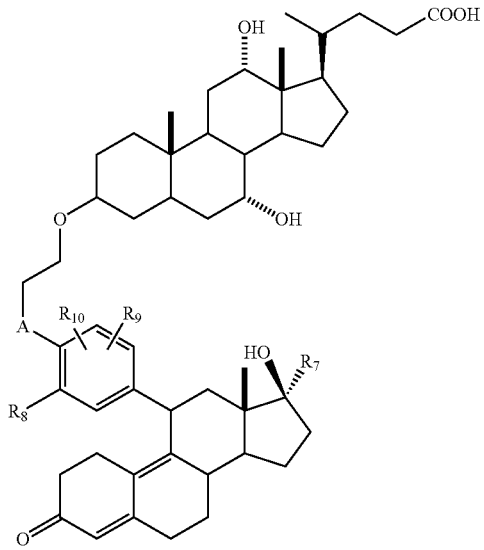

Compounds of the present invention can be prepared according to the methods described in Schemes 1-3. One method for the incorporation of potential linking groups onto cholic acid intermediates is described in Scheme 1. Cholic acid methyl ester is selectively activated at the 3-position, for example through treatment with a sulfonyl halide or the like. The activated 3-alcohol is displaced with ethylene glycol, and the resultant alcohol is activated as a leaving group to provide intermediate Z, for example through conversion to a halide, sulfonate, and the like.

In Scheme 2, intermediates A and B are prepared from the known ketone-ketal in several steps as follows. Addition of an organometallic reagent, for example propynyl-magnesium bromide and the like, to the C-17 ketone leads to the corresponding β-alcohol as the predominant stereoisomer. Selective epoxidation of the Δ(5,10) double bond, for example using hydrogen peroxide catalyzed by hexafluoroacetone, leads to an unsaturated epoxide, which reacts in an $SN_2'$ fashion with an organometallic reagent, for example 4-(N-Boc-N-methyl)-phenylmagnesium bromide, to provide the corresponding C-11 substituted allylic alcohol A. Acid-catalyzed deprotection, for example using p-toluenesulfonic acid hydrate, or hydrochloric acid, and the like, occurs with concomitant elimination of the C-5 alcohol, to provide an enone like B.

In Scheme 3, following an optional deprotection of the linking substituent at C-11, this fragment is coupled with the modified bile acid Z described in Scheme 1, for example using a base like triethylamine and the like to scavenge the acid generated in the course of the reaction. Hydrolysis of the ester group in the resultant linked product C generates the target compound.

Scheme 4. Alternative assembly of fragments

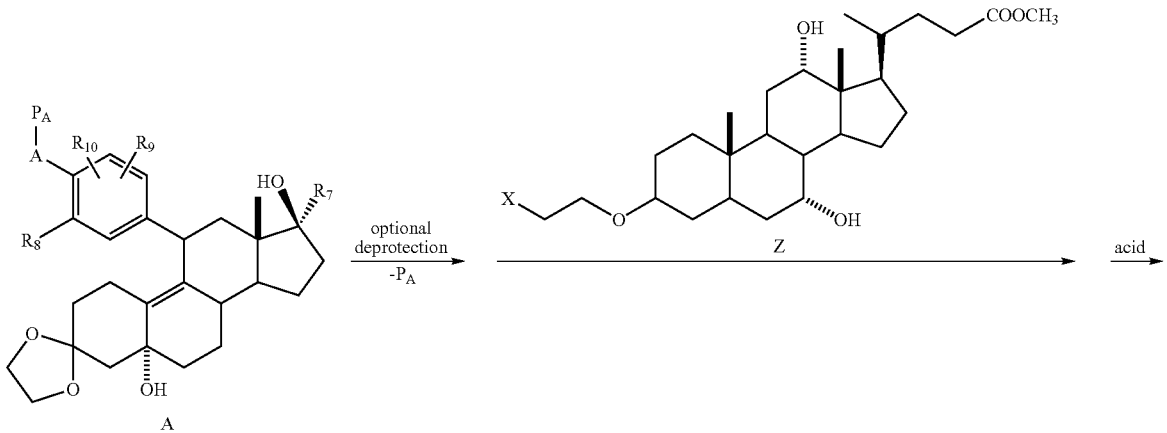

-continued

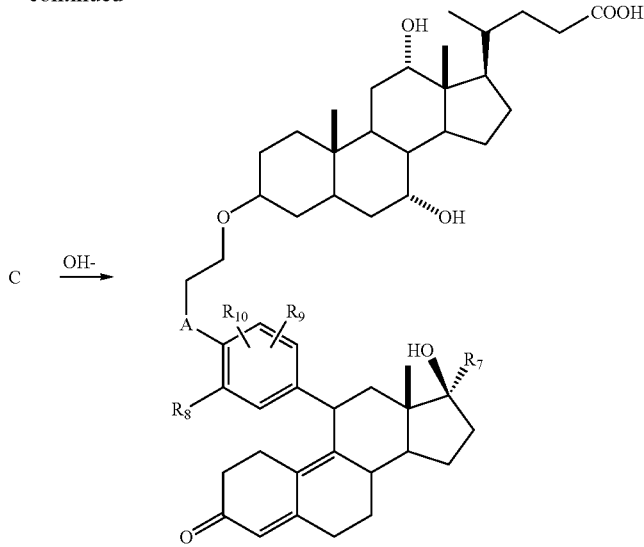

Scheme 4 describes an alternative to the coupling strategy described in Scheme 3. After an optional deprotection of the linking group at C-11, intermediate A from Scheme 2 may be directed coupled with the modified bile acid Z from Scheme 1. The coupled product is treated with an acid to remove the C-3 acetal and eliminate the C-3 alcohol, and the resultant enone-ester C is hydrolyzed as described previously to give the target compound.

Scheme 5. Alternative assembly of glucocorticoid antagonistic intermediates
Scheme 5A.

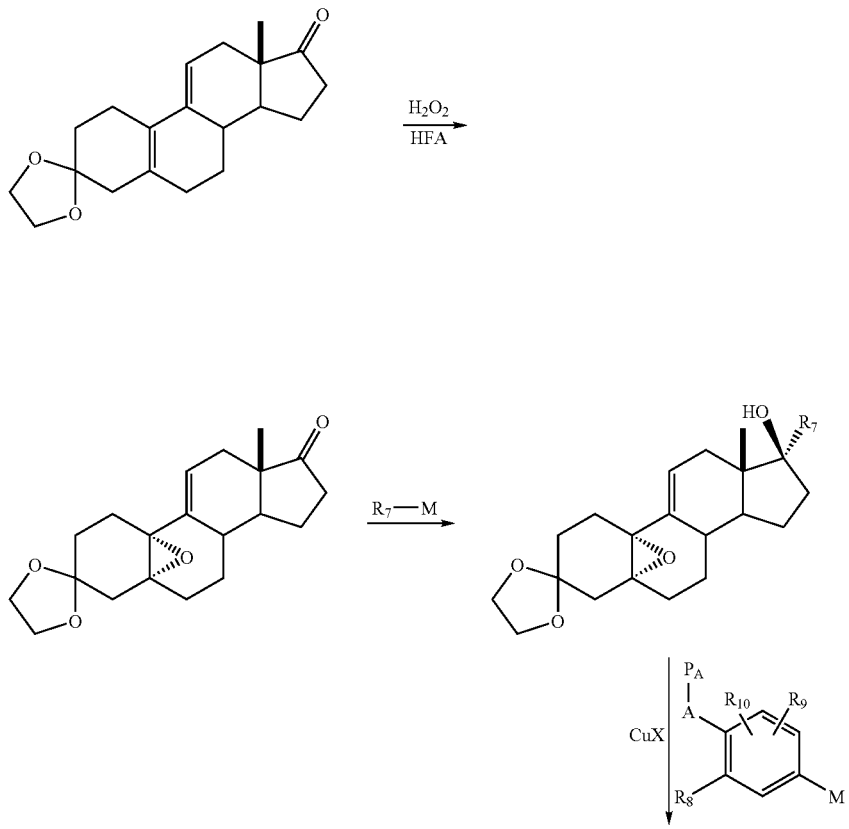

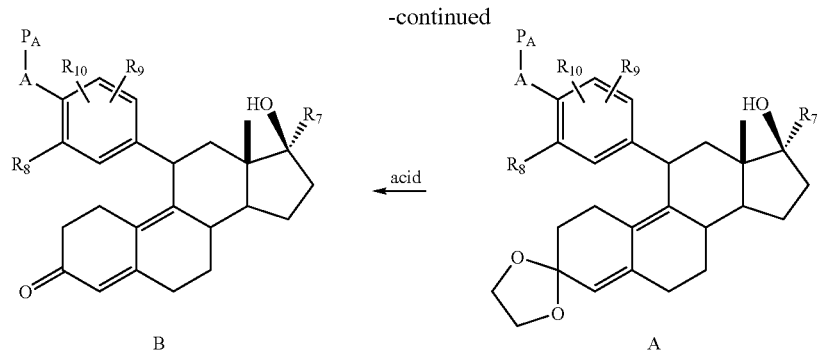
Scheme 5B.
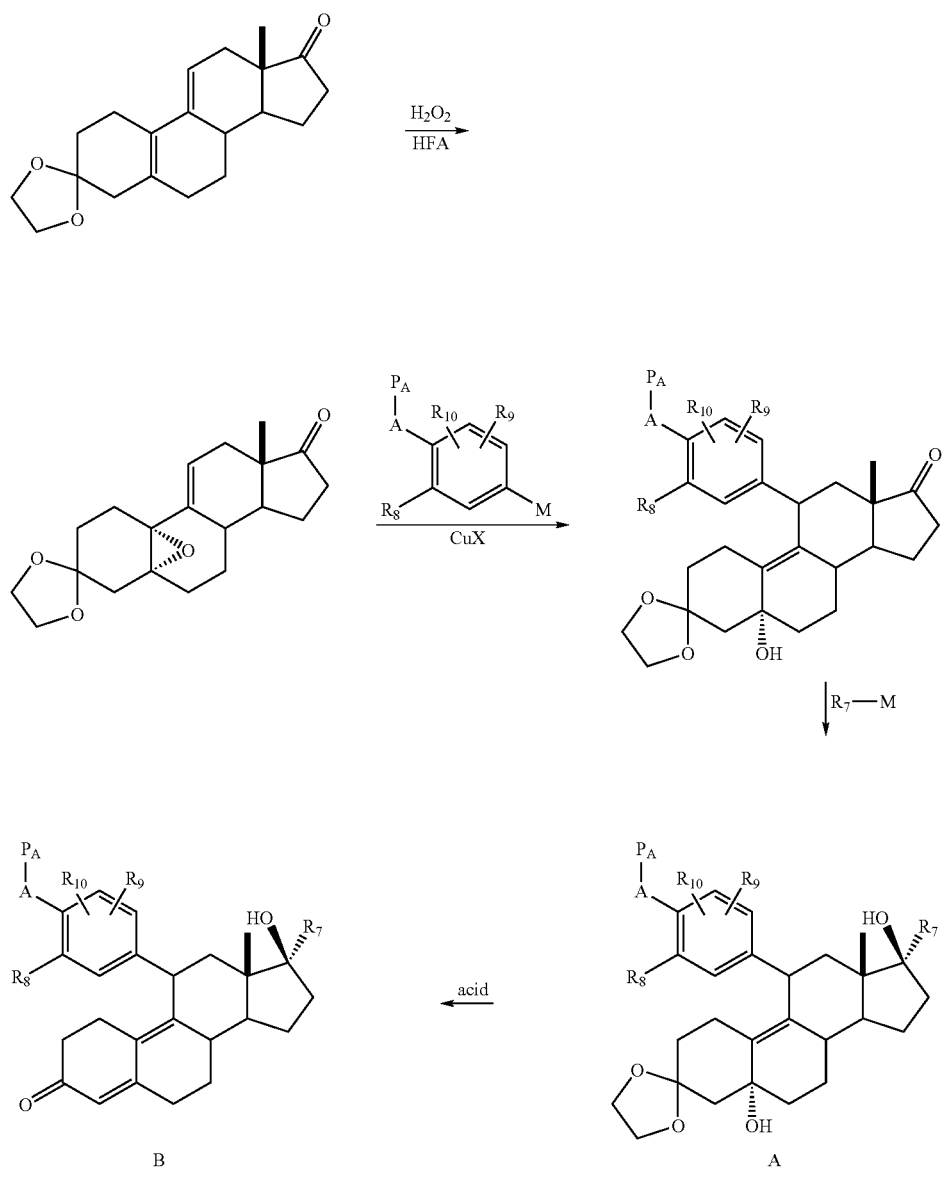

To facilitate structure-activity studies, key intermediates B may be prepared according several alternative strategies as described in Scheme 5. Thus, for example, as described in Scheme 5A, epoxidation of the Δ5,10 olefin may precede addition of the C-17 substituent. Further transformations of the resultant epoxy-alcohol are as described previously in Scheme 2. Alternatively, addition of the C-17 substituent may be postponed until late in the synthesis. In this case, demonstrated in Scheme 5B, the order of the C-11 and C-17 addition steps are reversed. All other transformations are as described in Scheme 2.

Scheme 6

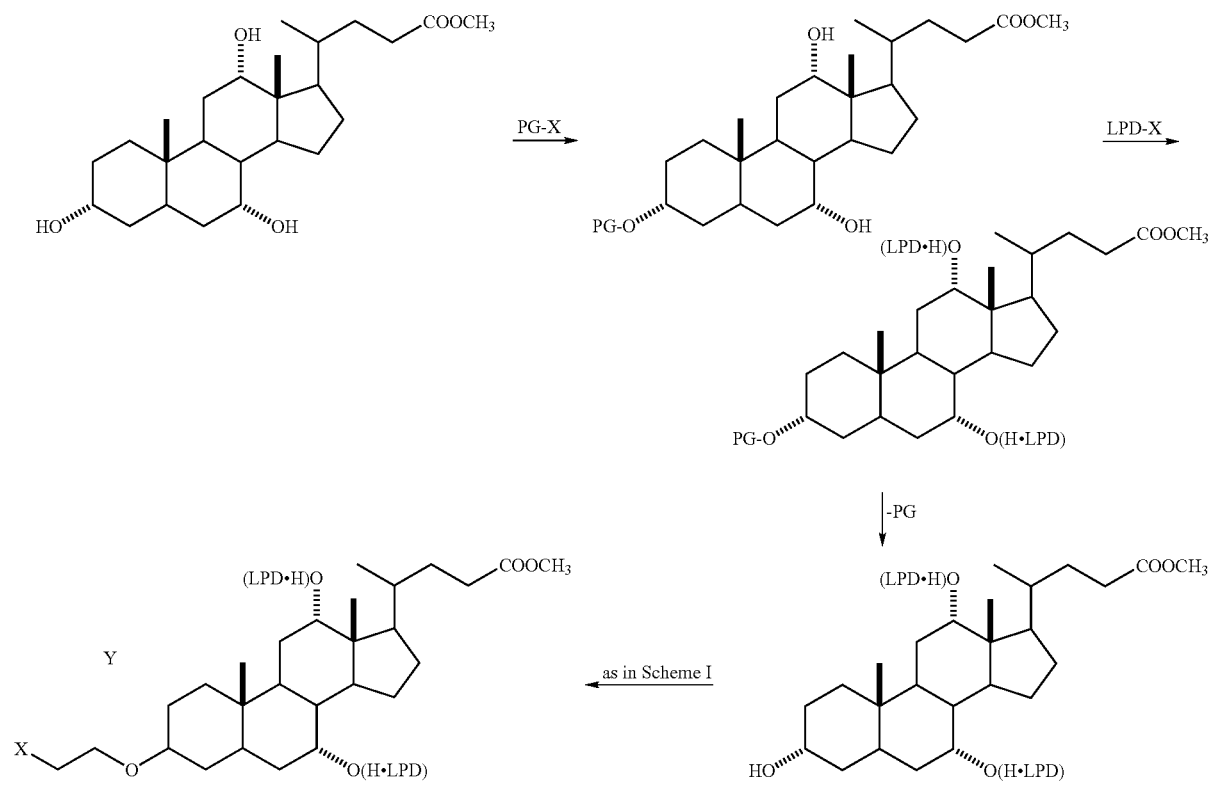

Prodrug forms of the compounds of the invention can be prepared according the methods outlined in Schemes 6-10. In Scheme 6, the C-3 hydroxyl group of a cholic acid derivative is protected, for example as a ester, trialkylsilyl ether and the like, allowing for the C-7 and/or C-12 hydroxyl groups to be treated with a latent form of the in vivo-cleavable moiety. Examples of this reactive group (LPD-X) might include a dialkylphosphochloridate, an activated acid, a chloroformate, and the like. The C-3 protecting group is selectively removed, and the resultant C-3 alcohol is converted to a potential linking group as described previously in Scheme 1, providing intermediate D.

Scheme 7.

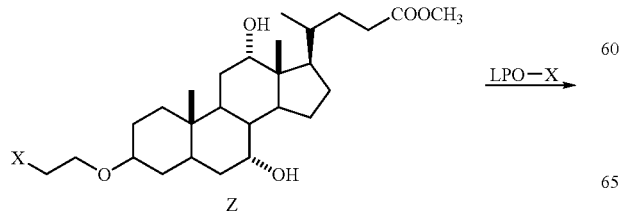

-continued

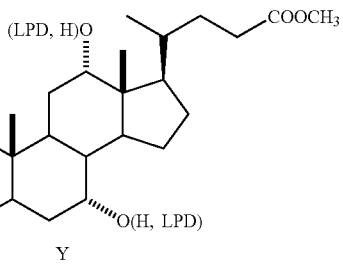

Alternatively, as shown in Scheme 7, a compound Z, prepared according to Scheme 1, may be treated at the C-7 and/or C-12 hydroxyl with a latent form of the in vivo-cleavable moiety to provide intermediate directly.

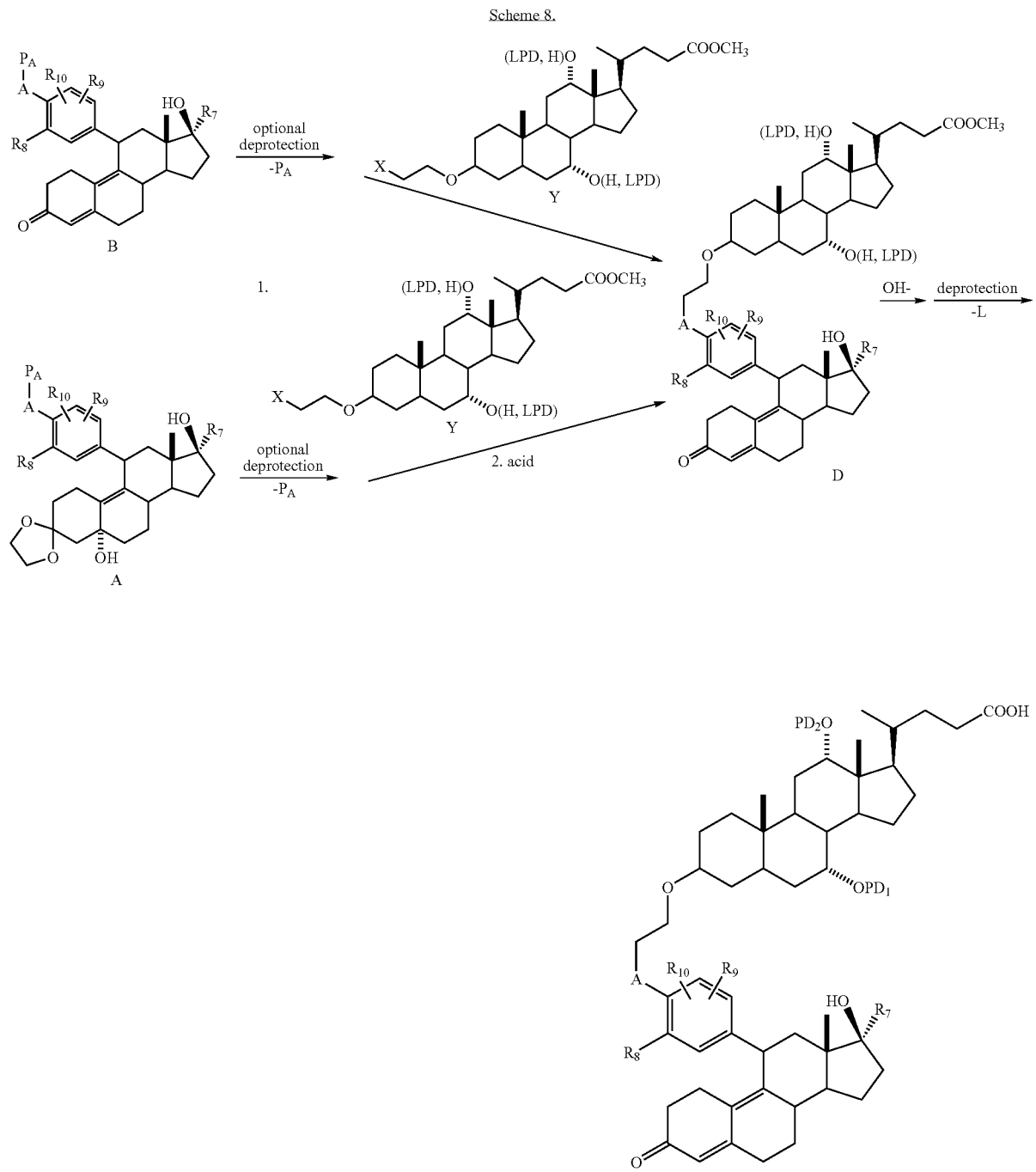

Scheme 8.

As shown in Scheme 8, compound Y prepared according to Scheme 6 or Scheme 7 can be treated with dienone B (after an optional deprotection) as in Scheme 3 to provide the fully protected coupled product D. Hydrolysis of the ester in D is followed by removal of the protecting groups to provide the final prodrug acid. Alternatively, coupled product D can be prepared through reaction of intermediate A (after optional deprotection) with compound Y, followed by treatment under acidic conditions.

33

Scheme 9.

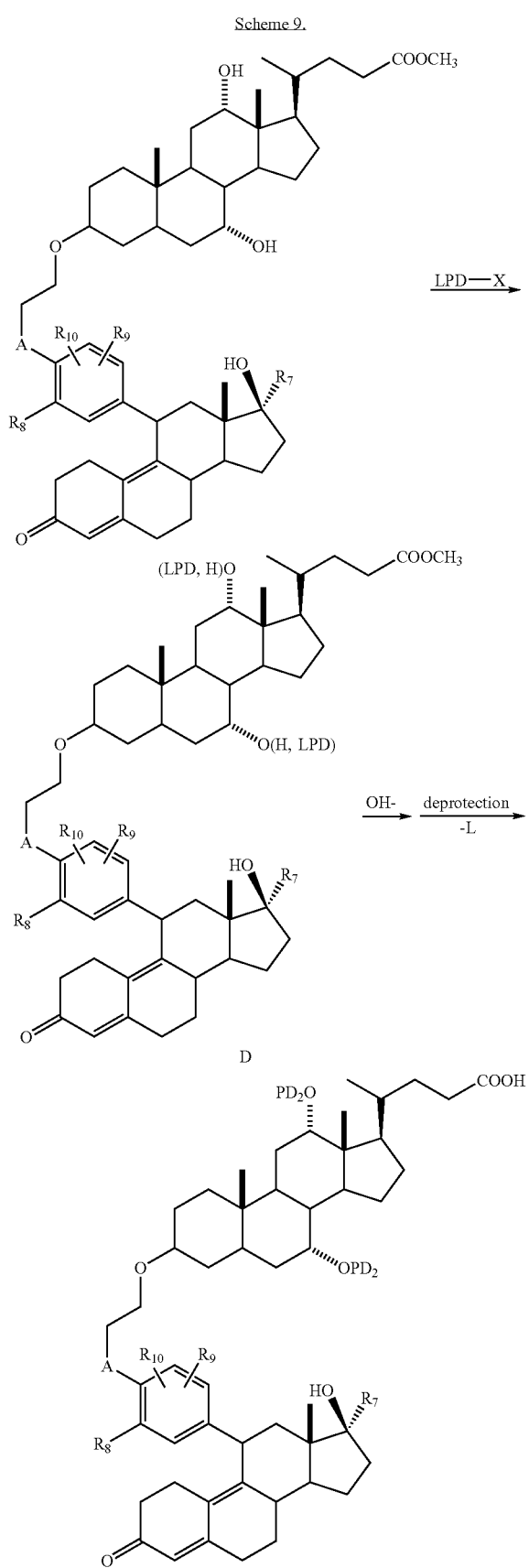

34

Scheme 9 demonstrates that compound D can be prepared directly from penultimate intermediate C through reaction with a latent form of the in vivo-cleavable moiety. Examples of this reactive group might include a dialkylphosphochloridate, an activated acid, a chloroformate and the like. Hydrolysis of the ester in D is followed by removal of the protecting groups to provide the final prodrug acid.

Scheme 10.

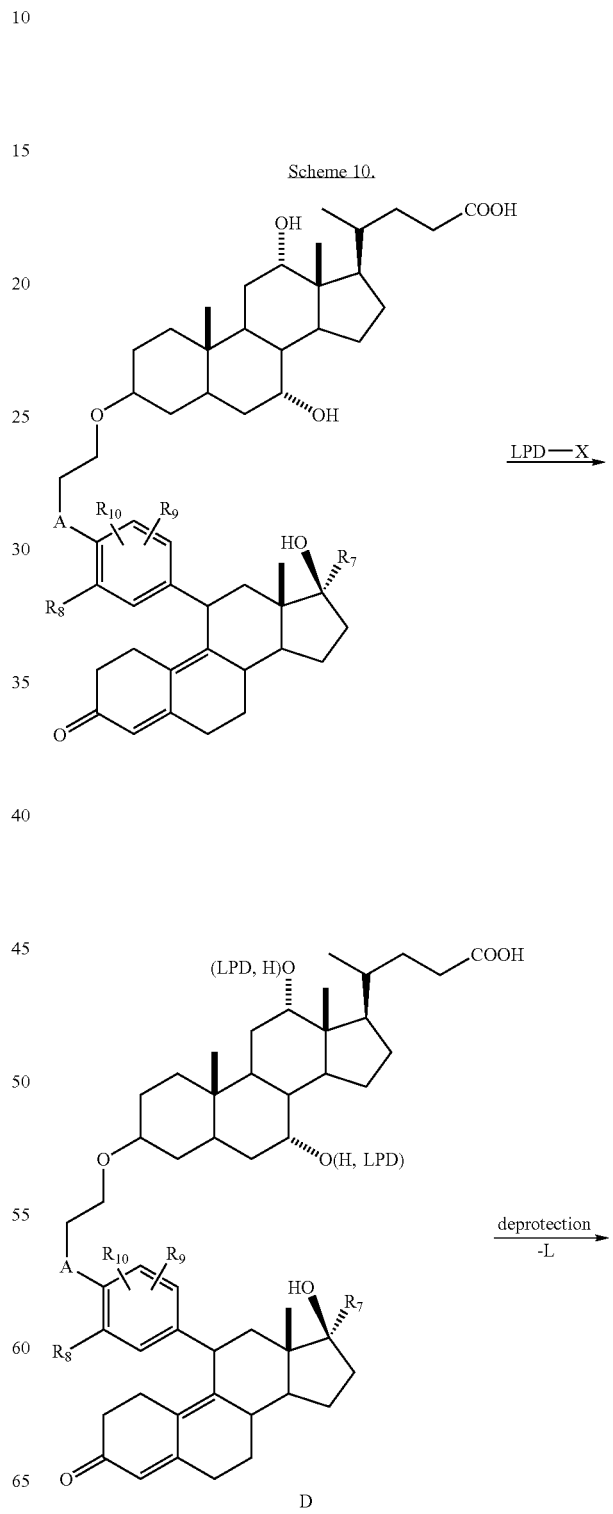

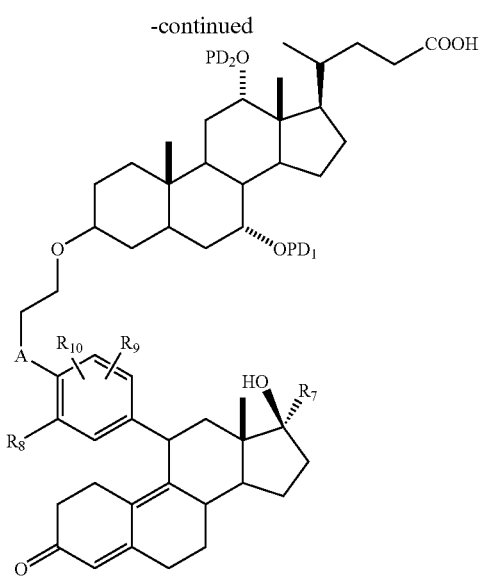

Scheme 10 indicates that compounds of the present invention may be used directly in the preparation of prodrug forms.

The compounds is treated with a latent form of the in vivo-cleavable moiety, followed by removal of the protecting groups. Examples of this reactive group might include a dialkylphosphochloridate, an activated acid, a chloroformate and the like.

The invention will now be described in connection with preferred embodiments of the Schemes, which are not intended to limit its scope. On the contrary, the invention covers all alternatives, modifications, and equivalents which are included within the scope of the claims. Thus, the following examples show an especially preferred practice of the invention, it being understood that the examples are for the purposes of illustration of certain preferred embodiments and are presented to provide what is believed to be the most useful and readily understood description of its procedures and conceptual aspects.

Synthetic Methods

Abbreviations which have been used in the descriptions of the scheme and the Examples that follow are: EtOAc for ethyl acetate, $CH_2Cl_2$ for dichloromethane, $CHCl_3$ for chloroform, $CH_3CN$ for acetonitrile, THF for tetrahydrofuran, MTBE for methyl tert-butyl ether.

EXPERIMENTALS

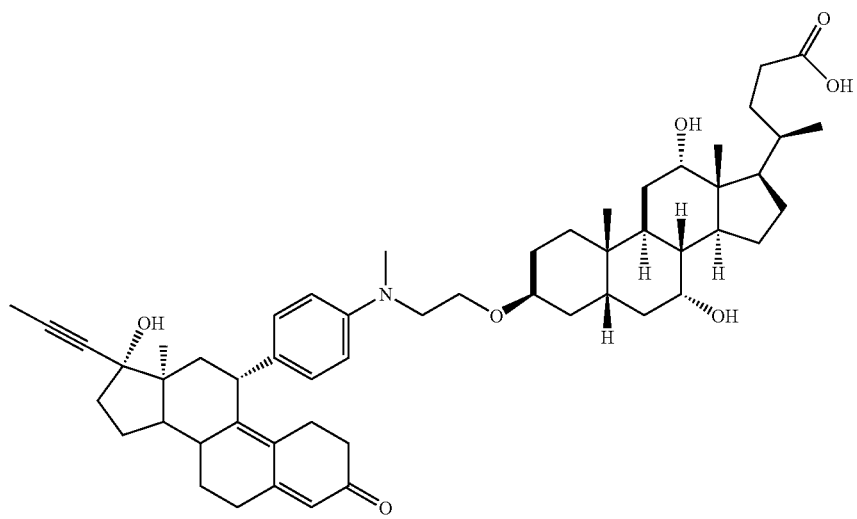

Example 1

(3β,5β,7α,12α)-7,12-Dihydroxy-3-{2-[{4-[17β-hydroxy-3-oxo-17α-prop-1-ynylestra-4,9-dien-11β-yl]phenyl}(methyl)amino]ethoxy}cholan-24-oic acid

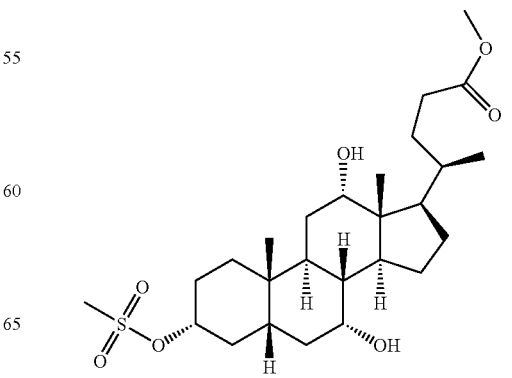

Example 1A

Methyl (3α,5β,7α,12α)-7,12-dihydroxy-3-(methanesulfonyloxy)cholan-24-oate

To a solution of cholic acid methyl ester (25 g, 59.2 mmol) in pyridine (75 mL), stirring at 0° C., was added methanesulfonyl chloride (5.04 mL, 65.1 mmol) dropwise over 30 minutes. The reaction was allowed to warm to room temperature and stir for 6 hours. The reaction mixture was poured into a mixture of EtOAc (200 mL), 1 N HCl (200 mL), and ice. The layers were separated, and the organic layer was washed with 1N HCl (2×50 mL), dried ($Na_2SO_4$) and concentrated to provide a light yellow oil. The crude material was passed through a plug of silica eluting with 50% EtOAc/hexanes to provide 24.5 g (83%) of the title compound as a light yellow oil that foamed into a white, sticky foam when placed on the high vacuum pump.

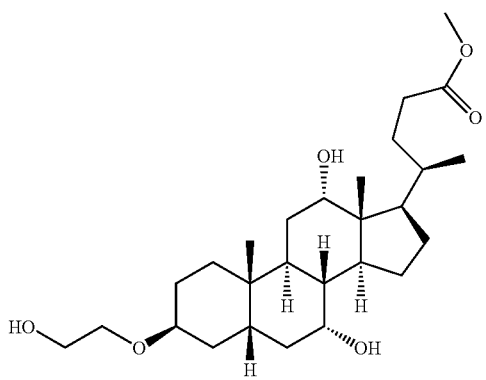

Example 1B

Methyl (3β,5α,7α,12α)-7,12-dihydroxy-3-(2-hydroxyethoxy)cholan-24-oate

A pressure vessel (250 mL flask) containing the compound of Example 1A (10.0 g, 20 mmol) was charged with ethylene glycol (20 mL) and pyridine (4 mL) at ambient temperature, sealed and then heated at 120° C. for 4 hours. The reaction was cooled to ambient temperature, diluted with EtOAc (50 mL), and quenched with 1N HCl (30 mL). The layers were separated and the organic layer was washed with 1N HCl (2×30 mL), dried ($Na_2SO_4$), and concentrated. Purification by silica gel chromatography (10%->40% acetone/hexanes) provided the title compound (3.5 g, 37%). MS (ESI) m/e 484 $(M+NH_4)^+$

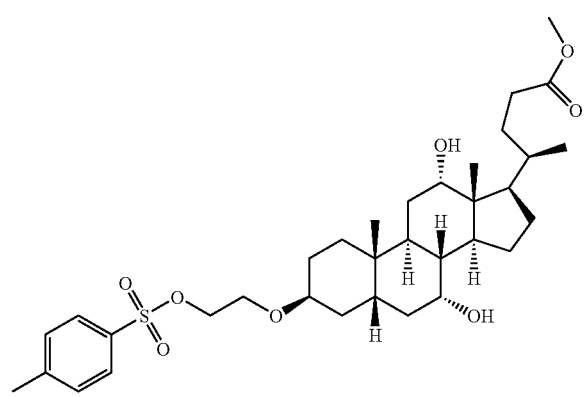

Example 1C

Methyl (3β,5β,7α,12α)-7,12-dihydroxy-3-[2-(p-toluenesulfonyloxy)ethoxy]cholan-24-oate The compound of Example 1B (1.50 g, 3.2 mmol) was dissolved in 15 ml of chloroform and 15 ml of pyridine; p-toluenesulfonyl chloride (920 mg, 4.83 mmol) was added, and the mixture was stirred overnight. Chloroform (250 ml) was added, the resultant solution was washed with 5% HCl solution and sat. $Na_2SO_4$. After solvent removal in vacuo, the crude product was purified by column chromatography on silica gel (40%->60% ethyl acetate/hexanes. The yield of the title compound was 1.40 g (71%).

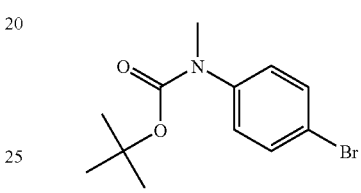

Example 1D

N-Boc-N-methyl-4-bromoaniline 5.0 mmol of 4-bromoaniline (0.86 g) is dissolved in 10 mL of THF; 1.09 g (5.0 mmol) of di-tert-butyl dicarbonate is added, and the resultant solution is warmed to 50° C. for 5 hours. The reaction is partitioned between water and ethyl acetate; the organic layer is washed with brine, dried over $Na_2SO_4$, and concentrated to give a white solid. This crude material is dissolved in 20 mL of dry THF and cooled in an ice bath; and 250 mg (1.25 eq) of NaH (60% oil dispersion) is added portionwise. Gas evolves, leaving a foamy semisolid after 15 min. Additional THF (10 mL) is added to break up the foam, followed by 0.50 mL (1.6 eq) of iodomethane. The resultant mixture is stirred overnight, warming slowly to ambient temperature. The reaction mixture is added carefully to aqueous 1N $H_3PO_4$ (some gas evolves!), the resulting mixture is extracted with ethyl acetate. The organic layer is washed with brine and dried over $Na_2SO_4$. The crude product is purified by silica gel chromatography, eluting with a gradient of 0->10% ethyl acetate/hexanes, providing 1.08 g (76% overall) of the title compound as a slightly yellowish oil.

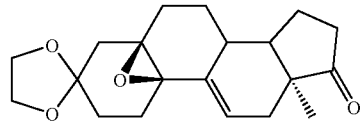

Example 1E (5'R,10'R,13'S)-13'-methyl-1',2',6',7',8',12',13',14', 15',16'-decahydro-17'H-spiro[1,3-dioxolane-2,3'-[5, 10]epoxycyclopenta[a]phenanthren]-17'-one To a solution of diene (5.0 g, 15.9 mmol), hexafluoroacetone trihydrate (349 mg, 1.59 mmol) and pyridine (75 mg, 0.95 mmol) in $CH_2Cl_2$ (160 mL) at 0° C. was added dropwise 30% $H_2O_2$ solution (2.7 g, 23.8 mmol). The reaction was stirred at 0° C. for 2 hours and at ambient temperature for 2 days (monitor by TLC). The reaction was quenched with 10% $Na_2S_2O_3$ solution, extracted with $CH_2Cl_2$ (250 mL×3) and dried over $Na_2SO_4$. Solvents were removed in vacuo, and the resultant yellow solid was triturated with 35 mL of diethyl ether with magnetic stirring overnight in a closed flask. The mixture was suction filtered through a coarse-porosity sintered glass funnel, rinsing three times with 5 mL of diethyl ether, and allowed to suck dry for 1 hours. The resulting filter cake was scraped into a fine powder and dried in vacuo to afford the title compound (2.0 g, 38% yield). The remaining material (~2.6 g) can be resubjected to the above procedure to recover an additional 0.5 g of alpha-epoxide.

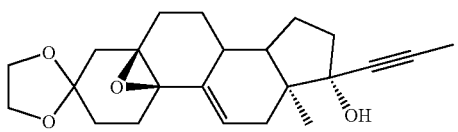

Example 1F (5'R,10'R,13'S,17'S)-13'-methyl-17'-prop-1-ynyl-1', 2',7',8',12',13',14',15',16',17'-decahydro-6'H-spiro[1, 3-dioxolane-2,3'-[5,10]epoxycyclopenta[a]phenanthren]-17'-ol To a solution of 100 mg (0.30 mmol) of the compound of Example 1E in THF (1.2 mL, distilled) at 0° C. was added dropwise 1-propynylmagnesium bromide solution (1.2 mL, 0.60 mmol, 0.5M in THF). the reaction mixture was stirred for 2 hrs. The solvent was removed in vacuo; the residue was quenched with saturated aqueous $NH_4Cl$ solution and extracted with EtOAc (20mL×3). The combined organic extracts were dried over $Na_2SO_4$. Solvent removal in vacuo gave 110 mg of the titled compound (yield: ~100%).

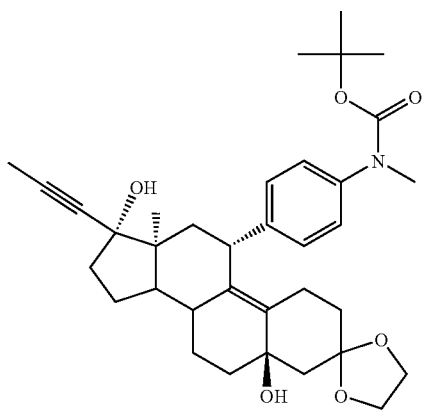

Example 1G tert-butyl 4-((5R,11R,13S,17S))-5,17-dihydroxy-13-methyl-17-prop-1-ynyl-1,2,4,5,6,7,8,11,12,13,14,15, 16,17-tetradecahydrospiro[cyclopenta[a]phenanthrene-3,2'-[1,3]dioxolan]-11-yl)phenyl(methyl)carbamate A 50 mL flask charged with Mg powder (44 mg, 1.8 mmol) was dried with heat-gun under $N_2$. After the apparatus was cooled to room temperature, THF (2 mL) and a small crystal of iodine were added. To the efficiently stirred mixture was added 0.6 mL of a solution of the compound of Example 1D (500 mg, 1.75 mmol) in THF (2 mL). After the mixture was heated to reflux for about 5 minutes, the iodine color quickly faded to colorless and then the mixture was cooled to room temperature. The remainder of the bromide solution was added dropwise over 20 minutes. The mixture was cooled in an ice-water bath for 30 minutes and the CuI (132 mg, 0.69 mmol, powder) was added in one portion. After the mixture was stirred for 2 minutes, a solution of the compound of Example 1F (256 mg, 0.69 mmol) in THF (2 mL) was added, causing the formation of a voluminous light yellow precipitate. After 30 minutes, $NH_4Cl$ (5 mL, sat) solution was slowly added, followed by EtOAc (10 mL). After the mixture was stirred for 10 minutes, the aqueous layer was separated and extracted with EtOAc. The combined organic layer was washed with brine (3×), dried over $Na_2SO_4$ and concentrated. The crude product was purified by HPLC (normal phase) to provide the titled compound (352 mg, 90% yield).

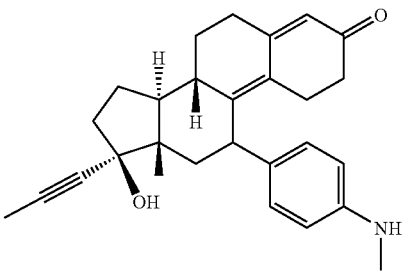

Example 1H (11β,17α)-17-hydroxy-11-(4-(methylamino)phenyl)-17-prop-1-ynylestra-4,9-dien-3-one The compound of Example 1G (36 mg) was dissolved in 0.3 mL of a solution of $TsOH.H_2O/CH_2Cl_2/THF$ (1.9 g/3 mL/3.8 mL); the resultant mixture was stirred at room temperature for 3 hour. The reaction mixture was added dropwise to $NaHCO_3$ solution (2 mL, saturated) and then extracted with EtOAc (3×). The combined organic layer was washed with brine, dried over Na2SO4 and concentrated. The crude product was purified by preparative TLC to provide the titled compound (20 mg, 74% yield).

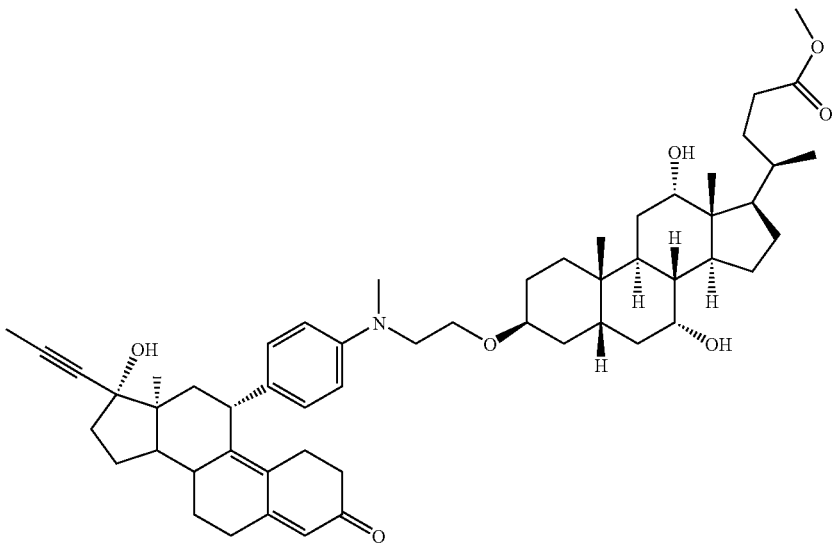

Example 1I

Methyl (3β,5β,7α,12α)-7,12-dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oate The compound of Example 1C (15 g, 24.2 mmol) and the compound of Example 1H (11 g, 26.5 mmol), were combined with NaI (2.7 g), and diisopropylethylamine (3.12 g) in 400 mL of acetonitrile in a 1 liter pressure bottle. The solution was heated at 100° C. TLC (EtOAc:hexane, 60:40) or HPLC was checked for the completion of the reaction; no starting material was observed after 16 hours. The reaction mixture was cooled to ambient temperature and filtered through Celite; the solvents were removed in vacuo. The crude material was diluted with EtOAc (500 mL) and washed with saturated ammonium chloride solution (2×100 ml). The solvent was removed in vacuo, and the crude material was loaded on silica gel column to elute with hexane/EtOAc (3:2-1:1-2:3). Pure fractions were collected and concentrated to provide 14.5 g (63.3%) of the titled compound.

Example 1J (3β,5β,7α,12α)-7,12-Dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 1I (1.40 g, 1.62 mmol) was dissolved in 15 ml of THF; 15 ml of 1N aqueous LiOH was added, and the resulting mixture was stirred for 5 hour at ambient temperature. The organic solvent was removed in vacuo, and enough water was added to make one phase. The solution was acidified with acetic acid to precipitate a light yellow solid, which was collected by filtration and washed several times with water. The product was dried overnight in a lyophilizer. Yield 1.35 g (98%) of the titled compound.

$^1$HNMR (500 MHz, MeOH) δ 7.07-7.71 (m, 4H), 5.76 (s, 1H), 4.57 (d, 1H), 3.95 (s, 1H), 3.78 (d, 1H), 3.74 (t, 1H), 3.44 (m, 1H), 3.23 (m, 3H), 2.86 (m, 1H), 2.66 (m, 1H), 2.50 (m, 2H), 2.16–2.41 (m, 7H), 2.15 (m, 2H), 2.08 (m, 1H), 1.95 (m, 3H), 1.85 (m, 5H), 1.75 (m, 5H), 1.57 (m, 7H), 1.40 (m, 8H), 1.31 (m, 6H), 1.01 (d, 3H), 0.92 (m, 5H), 0.71 (s, 3H), 0.48 (s, 3H); MS (ESI) m/e 850 (M+H)$^+$, 848 (M–H)$^-$; Exact mass Calcd. for $C_{54}H_{75}NO_7$: 850.5616; found 850.5620.

Alternative synthesis of (3β,5β,7α,12α)-7,12-dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid.

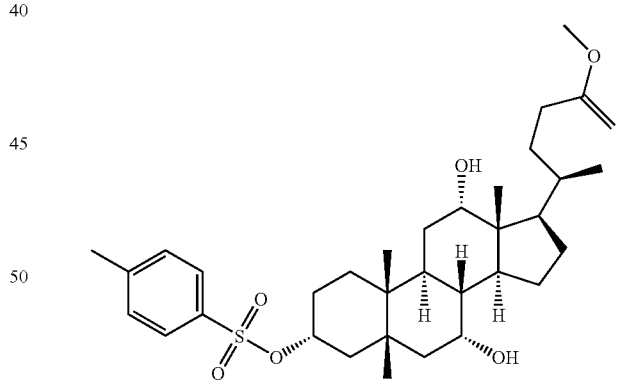

Example 1K, Alternative to Example 1A

Methyl (3α,5β,7α,12α)-7,12-dihydroxy-3-(p-toluenesulfonyloxy)cholan-24-oate

To a solution of cholic acid methyl ester (1000.0 g, 2.366 mol) in pyridine (2250 mL) at –10° C. was added a solution of p-toluenesulfonyl chloride (654.2 g, 2.431 mol) in pyridine (650 mL) dropwise over 2.5 hours while maintaining the reaction temperature at –10 to –6° C. The solution was mixed at −10° C. for an additional 12.5 hours, diluted with water (61.8 g) with continued cooling. The mixture at −7.5° C. was added over a period of 43 minutes to a mixture of MTBE (5 L) and 6N HCl (6.2 L). The layers were separated and the organic phase was washed with 7% NaHCO₃ (2 L), followed by 2% NaCl (2 L), and finally with pH 7 phosphate buffer (2 L). The organic phase was filtered, concentrated under reduced pressure with MTBE (3×200 mL) to give 1608.93 g of a very viscous pale-straw colored oil (95.3% potency adjusted yield) that was used directly in the next step. ¹H NMR (CDCl₃, 400 MHz) δ 7.79 (d, J=8.5 Hz, 2H), 7.32 (d, J=8.6 Hz, 2H), 4.40-4.31 (m, 1H), 3.97 (br s, 9H), 3.83 (br s, 1H), 3.68 (s, 3H), 2.60-2.50 (m, 1H), 2.45 (s, 3H), 2.43-1.34 (m, 25H), 0.99 (d, J=6.3 Hz, 3H), 0.88 (s, 3H), 0.69 (s, 3H). MS (ESI) Expected=576; base=594.2 (576+NH₄⁺).

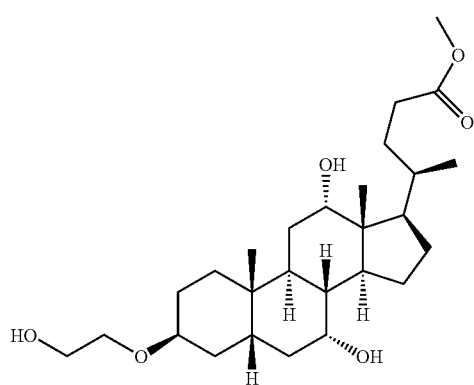

Example 1L, Alternative to Example 1B

Methyl (3β,5β,7α,12α)-7,12-dihydroxy-3-(2-hydroxyethoxy)cholan-24-oate

To the crude secondary tosylate from example 1K (1297.3 g, 2.25 mol) containing residual MTBE (311.5 g) was charged ethylene glycol (2516 g, 40.5 mol) and pyridine (445 g, 5.63 mol) and the mixture was heated to 60° C. for 15 hours then 80° C. for 4 hours. The mixture was cooled below 30° C. and isopropyl acetate (5.3 L) was added followed by 1.15 M HCl (3387 mL). The layers were separated and the aqueous layer was extracted with isopropyl acetate (3 L). The combined organics were washed with 10% brine (5 L) then concentrated to a residue. The residue was dissolved in methanol (15 L) and water (7.5 L) and the mixture was extracted with heptane (30 L). Additional water (7.5 L) was added and the methanol/water solution was heated to 45° C. then extracted with heptane (2×30 L). The methanol/water phase was cooled to room temperature then methylene chloride (15 L) and 20% brine (15 L) were added and the layers were separated. The methylene chloride solution was removed under reduced pressure and to the residue was added toluene, the product was filtered and dried to provide the compound of Example 1B as a white solid (462.2 g, 44%). ¹H NMR (CDCl₃, 400 MHz), δ 3.97 (m, 1H), 3.85 (m, 1H), 3.70 (m, 2H), 3.65 (s, 3H), 3.58 (m, 1H), 3.47 (m, 2H), 1.10-2.40 (m, 27H), 0.98 (d, J=6.3 Hz, 3H), 0.91 (s, 3H), 0.69 (s, 3H). MS (M+NH₄)⁺=484.3.

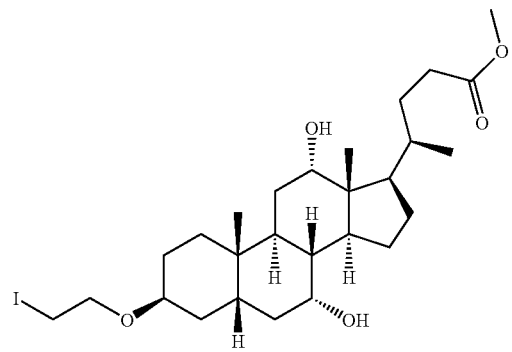

Example 1M, Alternative to Example 1C

Methyl (3β,5β,7α,12α)-7,12-dihydroxy-3-(2-(iodo)ethoxy]cholan-24-oate

To a solution of the primary alcohol from example 1B (30.0 g, 64.2 mmol) in pyridine (67.5 mL) at −11° C. was added p-toluenesulfonyl chloride (15.57 g, 81.5 mmol) in pyridine (22.5 mL) dropwise over 35 minutes while maintaining the reaction temperature at −11 to −8° C. The reaction was mixed at −12° C. for an additional 6 hours then quenched by adding water (1.5 g). The quenched reaction mixture at −12.5° C. was added over a period of 5 minutes into a mixture of t-butyl methyl ether (180 mL) and 3N HCl (369 mL) and the layers were separated. The organic phase was washed with 7% NaHCO₃ (90 mL), followed by 2% NaCl (90 mL), and finally with pH 7 buffer solution (90 mL). The organic phase was then concentrated under reduced pressure and chased with MTBE (90 mL), then acetone (90 mL) to afford 51.26 g of viscous oil. Acetone (386 mL) was added followed by sodium iodide (14.45 g, 96.4 mmol) and the reaction mixture was heated to reflux under nitrogen until the tosylate was consumed. MTBE (200 mL) and H₂O (200 mL) were added to the cooled reaction mixture and the layers were separated. The organic phase was washed with H₂O (150 mL), concentrated then chased with CH₃CN. The product was isolated from CH₃CN by filtration and dried to provide 29.51 g (76.9%) of the title compound.

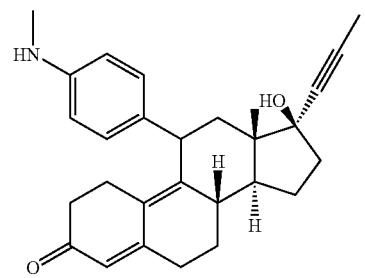

Example 1N, Alternative to Example 1H (11β,17α)-17-hydroxy-11-(4-(methylamino)phenyl)-17-prop-1-ynylestra-4,9-dien-3-one The compound of Example 1G (36 mg) was dissolved in 0.3 mL of a solution of TsOH.H₂O/CH₂Cl₂/THF (1.9 g/mL/3.8 mL); the resultant mixture was stirred at room temperature for 3 hours. The reaction mixture was added dropwise to NaHCO$_3$ solution (2 mL, saturated) and then extracted with EtOAc (3 times). The combined organic layer was washed with brine, dried over Na2SO4 and concentrated. The crude product was purified by preparative TLC to provide the title compound (20 mg, 74% yield).

Example 1O, Additional Alternative to Example 1H (11β,17α)-17-hydroxy-11-(4-(methylamino)phenyl)-17-prop-1-ynylestra-4,9-dien-3-one To a solution of (11β,17α)-17-hydroxy-11-(4-(dimethylamino)phenyl)-17-prop-1-ynylestra-4,9-dien-3-one (200 g, 0.466 mol) in CH$_2$Cl$_2$ (500 mL) was added a filtered solution of NMO (260 g, 2.22 mol) in CH$_2$Cl$_2$ (1250 mL) which has been dried over Na$_2$SO$_4$ and the resulting solution was cooled to a –10° C. under N$_2$. A solution of TPAP (16.1 g, 0.046 mol) in CH$_2$Cl$_{12}$ (150 mL) was added dropwise over 25 minutes and the resulting solution was mixed at –10° C. The reaction was quenched by addition of 10% bisulfite (2100 mL) via addition funnel over 20 min. The solution was then warmed to room temperature and stirred an additional 10 min. EtOAc (3.5 L) and H$_2$O (2 L) were added and the layers were separated. The aqueous layer was back-extracted with EtOAc (2 L) and the combined organics were washed with pH 7 phosphate buffer (2×4 L). The organic layer was then filtered through celite and decolorized with carbon (Darco G-60, 46.1 g). The product solution was concentrated and the product precipitated. The product was filtered and dried to give 130.17 g of the formamide (63.0%). $^1$H NMR (CDCl$_3$, 400 MHz) δ 8.47 (s, 1H), 7.22 (d, J=8.1 Hz, 2H), 7.09 (d, J=8.7 Hz, 2H), 5.80 (s, 1H), 4.44 (d, J=7.2 Hz, 1H), 3.31 (s, 3H), 2.85-2.2 (m, 11H), 1.92 (s, 1H), 2.1-1.3 (m, 6H), 0.53 (s, 3H). Sample also contains ca. 20 mole % EtOAc. MS (ESI), M+1=444, M–1=442.

To a solution of formamide (130.17 g, 0.265 mol) in methanol (2.6 L) at 15-20° C. was added a 5° C. aqueous HCl solution (696 mL conc. HCl and 1440 mL H$_2$O). The reaction was warmed to room temperature and mixed for 40 hours. The reaction mixture was cooled to 15° C. and the pH was adjusted by addition of 10% Na$_2$CO$_3$ solution. The product began to precipitate at pH 3 (final pH=7.05 at 12° C.). The product was isolated by filtration then the wet cake was dissolved in CH$_2$Cl$_2$ (700 mL), the layers were separated and the organic layer was concentrated to a thick residue under vacuum. After solvent switch to CH$_3$CN, the product was filtered and dried to provide the compound of Example 1H (104.2 g, 85.4%). $^1$H NMR (CDCl$_3$, 400 MHz) δ 6.98 (d, J=8.1 Hz, 2H), 6.56 (d, J=8.7 Hz, 2H), 5.77 (s, 1H), 4.35 (d, J=6.9 Hz, 1H), 2.83 (s, 3H), 2.85-2.1 (m, 10H), 1.91 (s, 3H), 2.1-1.3 (m, 6H), 0.53 (s, 3H). Sample also contains ca. 80 mole % CH$_3$CN. MS (ESI), M+1=416, M–1=414.

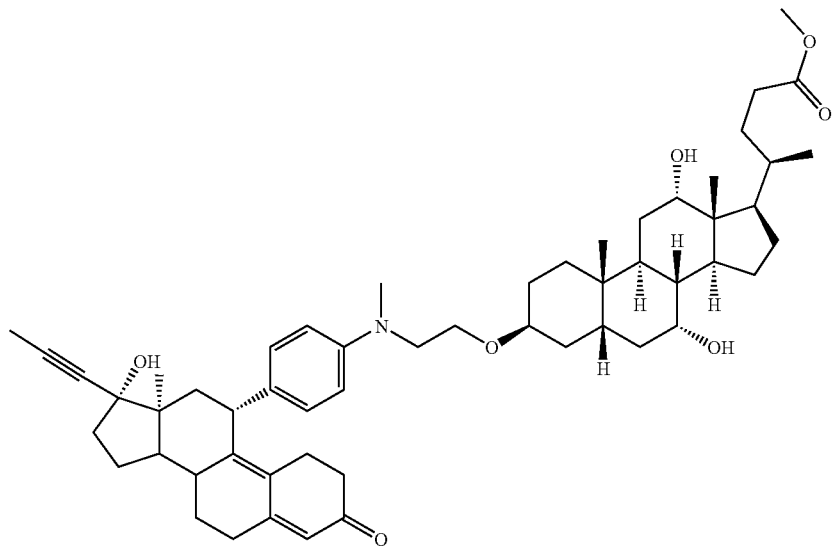

Example 1P, Alternative to Example 1I

Methyl (3β,5β,7α,12α)-7,12-dihydroxy-3-{2-[{4-[(11β,17α)-17-prop-1-ynylestra-4,9-dien-11-yl]phenyl}(methyl)amino]ethoxy}cholan-24-oate A solution of the compound of Example 1H (4.0 g, 9.63 mmol), the primary iodide of Example 1M (7.44 g, 12.9 mmol), diisopropylethylamine (1.66 g, 12.9 mmol) in N,N-dimethylacetamide (20 mL) was heated to 80° C. under nitrogen for 18 h. The cooled reaction mixture was diluted with isopropyl acetate (50 mL) and washed with 10% NH$_4$Cl (50 mL) then pH 7 phosphate buffer (50 mL). The organic phase was then concentrated in vacuo and the crude product was chromatographed on silica (50% EtOAc/heptane to 100% EtOAc) to provide the title compound (5.95 g, 76.8%).

Example 1Q, Additional Alternative to Example 1I

Methyl (3β,5β,7α,12α)-7,12-dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oate A solution of (11β,17α)-17-hydroxy-11-(4-(dimethylamino)phenyl)-17-prop-1-ynylestra-4,9-dien-3-one (4.14 g, 9.63 mmol), the primary iodide from Example 1L (7.44 g, 12.9 mmol), diisopropylethylamine (1.66 g, 12.9 mmol) in N,N-dimethylacetamide (20.7 mL) was heated to 80° C. under nitrogen for 19 h. The cooled reaction mixture was diluted with isopropyl acetate (50 mL) and washed with 10% NH$_4$Cl (50 mL) then pH 7 phosphate buffer (50 mL). The organic phase was then concentrated in vacuo and the crude product was chromatographed on silica (50% EtOAc/heptane to 100% EtOAc) to provide the title compound (4.96 g, 60.6%).

Example 1R, Additional Alternative to Example 1I

Methyl (3β,5β,7α,12α)-7,12-dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oate The primary alcohol from Example 1B (8.69 g, 18.62 mmol) was dissolved in CH$_2$Cl$_2$ (87 mL) and N,N-diisopropylethylamine (6.14 g, 47.52 mmol) was added, and the solution was cooled to −45 to −55° C. Trifluoromethanesulfonic anhydride (5.31 g, 18.82 mmol) was added at −52° to −47° C. over 2.5 h. The solution was mixed at ca. −48° C. for 47 min. then (11β,17α)-17-hydroxy-11-(4-(dimethylamino)phenyl-17-prop-1-ynylestra-4,9-dien-3-one (5.00 g, 11.6 mmol) was added and the mixture was warmed to −6° C. and mixed for 88 h. The solution was washed with 10% NH$_4$Cl solution and the solvent was removed in vacuo. The residue was dissolved in acetonitrile (50 mL) and the solvent was removed in vacuo; acetonitrile was added to obtain a final acetonitrile volume of ca. 10 mL/g of starting aniline. N,N-Diisopropylethylamine (2.27 g, 17.56 mmol) and NaI (5.24 g, 34.96 mmol) were added to the solution and the mixture was heated to reflux an mixed for 45 h. The slightly hazy solution was cooled and CH$_2$Cl$_2$ (20 mL) and EtOAc (50 mL) were added, and the solution was washed with 5% NH$_4$Cl solution followed by 20% NaCl solution. Purification by silica gel chromatography (EtOAc/heptane gradient) provide the title compound (82.7%).

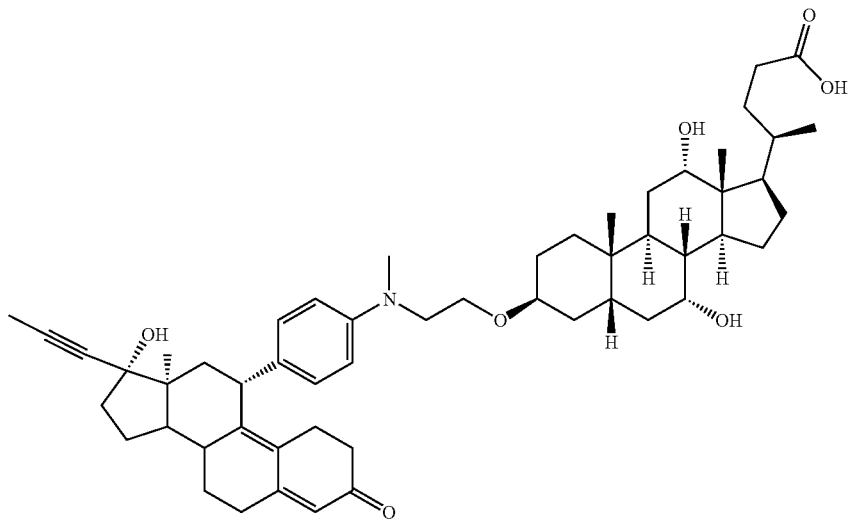

Example 1S, Alternative to Example 1J (3β,5β,7α,12α)-7,12-Dihydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid To a solution of the compound of Example 1I (17.28 g, 20.0 mmol, 91% chemical potency, therefore 15.72 g, 18.2 mmol) in EtOH (173 mL) at 5° C. was charged 3N KOH (33.3 mL, 100 mmol) at a rate to maintain an internal temperature <7° C. The reaction was stirred at 5° C. for 17 hour. The reaction mixture was neutralized with 3N HCl (33.3 mL, 100 mmol) while maintaining the internal temperature <10 ° C. (end pH was adjusted from 4.63 to 4.87 with 0.2 mL of 3N KOH). The reaction mixture crystallized after a few minutes post addition of 3N HCl. The reaction mixture was allowed to warm to ambient temperature, seeded (20 mg of seed crystals), warmed to 40° C. for 3 hours and slowly cooled back to ambient temperature stirred an additional 16 hours. The slurry was filtered, washed and dried to provide 14.30 g (92.4%) of the title compound.

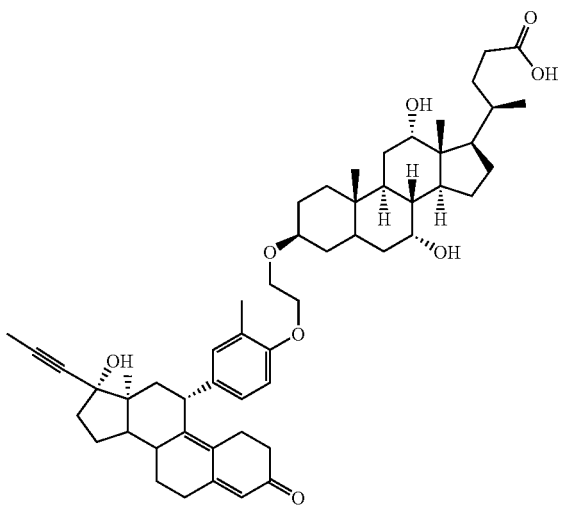

Example 2

(3β,7α,12α)-7,12-dihydroxy-3-(2-(4-(17β-hydroxy-3-oxo-17α-prop-1-ynylestra-4,9-dien-11β-yl)-2-methylphenoxy)ethoxy)cholan-24-oic acid Example 2A 1 Allyloxy-4-bromo-2-methyl-benzene A solution of 4-Bromo-2-methyl-phenol (2.0 g, 10.7 mmol) in THF (100 mL) was added solid $Cs_2CO_3$ (3.8 g, 11.7 mmol) and allyl bromide (1.9 mL, 21.4 mmol). The reaction mixture was stirred at room temperature for 20 hours. Upon completion, the solution was diluted with aqueous $NH_4Cl$ and extracted twice with ethyl acetate. The combined organic extracts were washed with brine, dried ($MgSO_4$), concentrated in vacuo and purified by column chromatography (0 to 100% ethyl acetate in hexanes) to provide 1.1 g (45%) of a white solid.

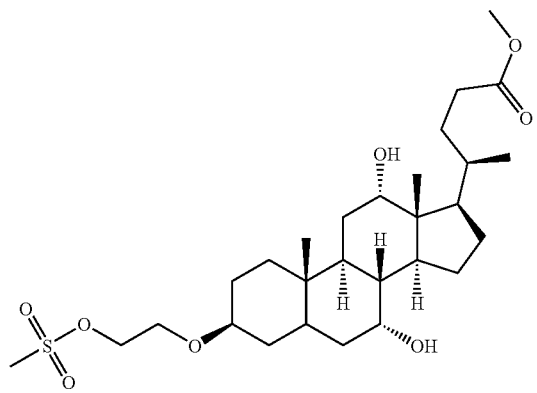

Example 2B

Methyl (3β,7α,12α)-7,12-dihydroxy-3-(2-((methylsulfonyl)oxy)ethoxy)cholan-24-oate The compound of example 1B (1.0 g, 2.1 mmol) was dissolved in THF (21 mL) and cooled at 0° C. To the cooled solution was added methanesulfonyl chroride (0.25 mL, 3.21 mmol) followed by the dropwise addition of triethylamine (0.45 mL, 3.21 mmol). The reaction solution was warmed to room temperature and allowed to stir overnight. Saturated aqueous $NH_4Cl$ was added and the solution was extracted twice with ethyl acetate. The organic phase was washed with brine, dried ($MgSO_4$), concentrated and purified via column chromatography (1:1 hexanes:ethyl acetate). The yield of the product was 429 mg (37%).

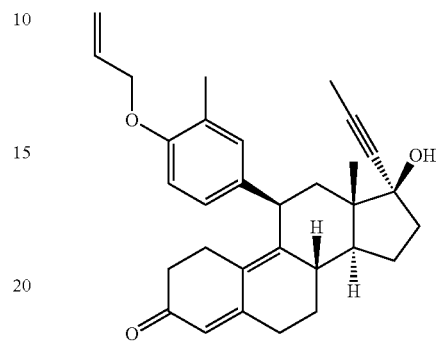

Example 2C (11β,17α)-11-4(allyloxy)-3-methylphenyl)-17-hydroxy-17-prop-1-ynylestra-4,9-dien-3-one Mg powder (916 mg, 38 mmol) was added to a round-bottom flask and flame dried. Upon cooling to room temperature, a crystal of iodine was added. To the combined solids was added 30 mL THF and the suspension was immersed in a water bath. The compound made in example 2A (8.6 g, 38 mmol as a solution in 10-30 mL THF) was then added dropwise. Reaction initiation, indicated by a loss of the iodine color, occurred within 15 minutes of addition of the bromide. The reaction solution was cooled to 0° C. and CuI (3.6 g, 19 mmol) was added in one portion. After 2 minutes, a solution of the epoxide from example 1F (2.8 g, 7.5 mmol) dissolved in 10 mL THF was added rapidly. After stirring at 0° C. for 1 hour, the reaction was quenched with aqueous $NH_4Cl$ and extracted with ethyl acetate. The organic extracts were washed with brine, dried ($MgSO_4$) and concentrated. The crude residue was dissolved in THF (150 mL) and 2M HCl (75 mL) was added. The reaction mixture was stirred at room temperature for 1 hour. Aqueous $NaHCO_3$ was added to neutralize the reaction and the resulting solution was extracted with ethyl acetate. The organic extracts were washed with brine, dried ($MgSO_4$) concentrated and purified by column chromatography (4:1 hexanes:ethyl acetate). The yield of the reaction was 737 mg (21%).

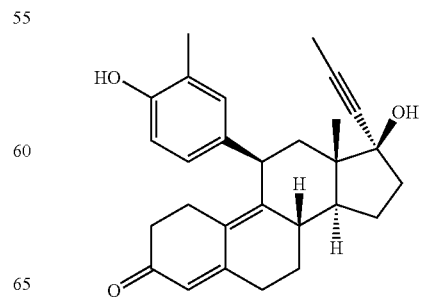

Example 2D (11β,17α)-17-hydroxy-11-(4-hydroxy-3-methylphenyl)-17-prop-1-ynylestra-4,9-dien-3-one The compound described in example 2C (737 mg, 1.6 mmol) was dissolved in methylene chloride (8 mL). To that solution was added phenylsilane (0.4 mL, 3.2 mmol) and Pd(Ph$_3$)$_4$ (186 mg, 0.2 mmol) at which point the reaction mixture turned black. After stirring for 1 hour at room temperature, the solution was diluted with brine and extracted twice with ethyl acetate. The combined organic fractions were dried over MgSO$_4$, concentrated and purified by column chromatography (70:30 hexanes:ethyl acetate) to provide 369 mg (55%) of white solid product.

Example 2E

Methyl (3β,7α,12α)-7,12-dihydroxy-3-(2-(4-((11β,17α)-17-hydroxy-3-oxo-17-prop-1-ynylestra-4,9-dien-11-yl)-2-methylphenoxy)ethoxy)cholan-24-oate The phenol from example 2D (252 mg, 0.6 mmol) and the mesylate made in Example 2B (390 mg, 0.7 mmol) were combined and dissolved in THF (6 mL). To that solution was added Cs$_2$CO$_3$ (600 mg, 1.8 mmol) and nBu4NI (450 mg, 1.2 mmol) and the resulting mixture was warmed to 55° C. for 24 hours. Upon cooling to room temperature, the mixture was diluted with brine and extracted with ethyl acetate. The organic fractions were dried over MgSO$_4$ and concentrated in vacuo and purified using column chromatography (70:30 hexanes:ethyl acetate). The yield of the coupling was 480 mg (93%).

Example 2F (3β,7α,12α)-7,12-dihydroxy-3-(2-(4-((11β,17β)-17-hydroxy-3-oxo-17-prop-1-ynylestra-4,9-dien-11-yl)-2-methylphenoxy)ethoxy)cholan-24-oic acid The ester described in Example 2E was dissolved in a mixture of THF (2 mL) and methanol (2 mL). To that mixture was added LiOH (1.4 mL of a 1 M solution in water). The resulting mixture was stirred at room temperature for 2 hours. The reaction mixture was then diluted with water and washed with diethyl ether. The aqueous fraction was acidified with 1 M H$_3$PO$_4$ and extracted with ethyl acetate. The combined organic fractions were dried over MgSO$_4$ and concentrated in vacuo. The crude, off-white solid was not purified further. $^1$H NMR (300 mHz, CDCl$_3$): δ 6.95 (d, J=2.03 Hz, 1H), 6.84 (m, 1H), 6.71 (d, J=8.48 Hz, 1H), 5.76 (s, 1H), 4.34 (d, J=6.10 Hz, 1H) 4.06 (m, 2H), 3.99 (s, 1H), 3.85 (d, J=2.37, 1H), 3.72 (dd, J=4.58, 6.27 Hz, 2H), 3.65 (d, J=2.71 Hz, 1H ), 2.75 (m, 2H), 2.59 (m, 4H), 2.36 (m, 12H), 2.19 (s, 3H), 1.97 (m, 4H), 1.90 (m, 3H), 1.54 (m, 19H), 1.01 (m, 3H), 0.90 (s, 3H), 0.71 (s, 3H), 0.53 (s, 3H). MS (ESI) m/e 851.6 (M+H)$^+$, 849.6 (M−H).

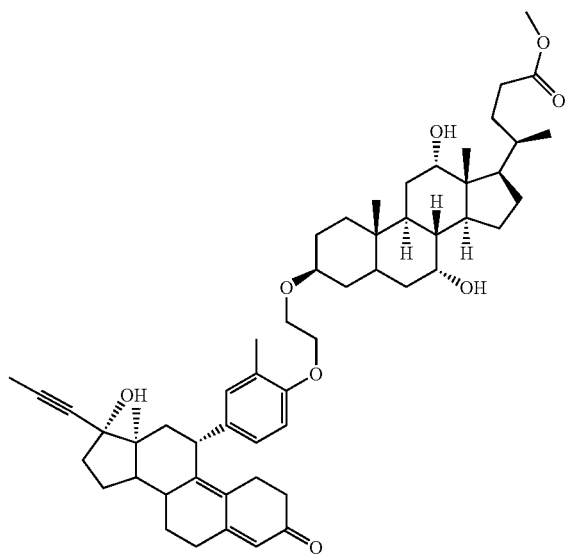

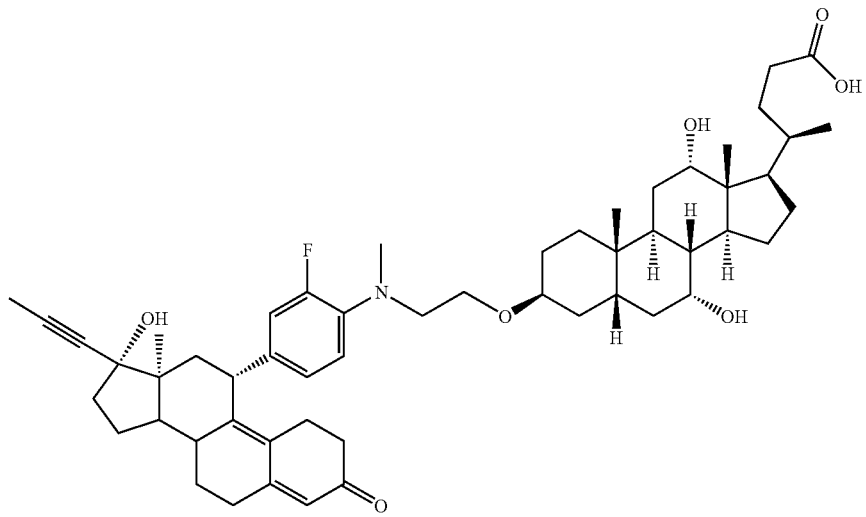

Example 3

(3β,5β,7α,12α)-7,12-dihydroxy-3-{2-[{4-[17β-hydroxy-3-oxo-17α-prop-1-ynylestra-4,9-dien-11β-yl]-2-fluorophenyl}(methyl)amino]ethoxy}cholan-24-oic acid

Example 3A

N-Boc-N-methyl-2-fluoro-4-bromoaniline

The compound was prepared according to the procedures of Example 1D, substituting 4-bromo-2-fluoroaniline for 4-bromoaniline.

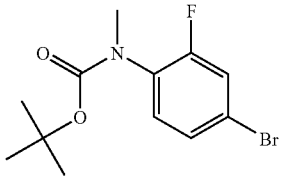

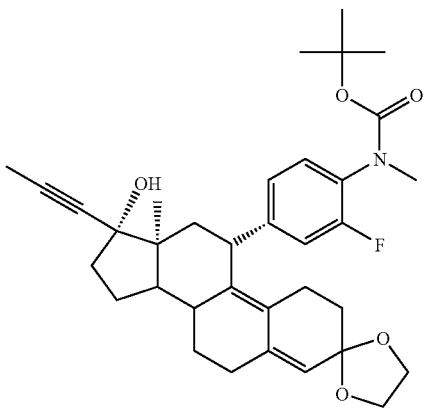

Example 3B tert-butyl 2-fluoro-4-((11R,13S,17S)-17-hydroxy-13-methyl-17-prop-1-ynyl-1,2,6,7,8,11,12,13,14,15,16,17-dodecahydrospiro[cyclopenta[a]phenanthrene-3,2'-[1,3]dioxolan]-11-yl)phenyl(methyl)carbamate The compound was prepared by using the procedures of Example 1G, substituting the compound of Example 3A for the compound of Example 1D (95% yield). $^1$H NMR (300 MHz, DMSO) δ 7.23 (t, J=8.4 Hz, 1H), 7.06 (m, 1H), 7.02 (m, 1H), 5.07 (s, 1H), 4.26 (d, J=6.3 Hz, 1H), 4.17 (m, 1H), 3.91-3.70 (m, 4H), 3.08 (s, 3H), 2.33-0.98 (m, 16H), 1.83 (s, 3H), 1.29 (s, 9H), 0.32 (s, 3H); MS (ESI) m/e 578 (M+H)$^+$.

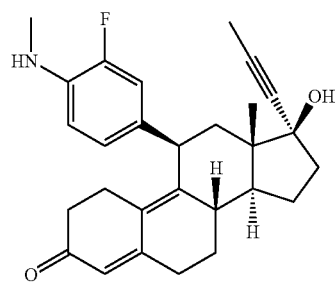

Example 3C (11β,17α)-11-(3-fluoro-4-(methylamino)phenyl)-17-hydroxy-17-prop-1-ynylestra-4,9-dien-3-one To a solution of the compound of Example 3B (490 mg, 0.85 mmol) in CH$_2$Cl$_2$ (2 mL) at 0° C. was added dropwise a solution of TFA in CH$_2$Cl$_2$ (6 mL of 50% solution). The resultant mixture was stirred at 0° C. for 35 minutes. The reaction mixture was neutralized by adding dropwise NaHCO$_3$ solution (saturated) and then extracted with EtOAc (3 times). The combined organic layer was washed with brine, dried over Na$_2$SO$_4$ and concentrated. The crude product was purified by silica gel chromatography (33% ethyl acetate/hexane) to afford the title compound (244 mg, 66% yield). $^1$H NMR (300 MHz, CDCl$_3$) δ 6.84-6.76 (m, 2H), 6.64 (t, J=8.3 Hz, 1H), 5.77 (s, 1H), 4.33 (d, J=6.9 Hz, 1H), 2.87 (s, 3H), 2.81-1.30 (m, 18 H), 1.89 (s, 3H), 0.55 (s, 3H); MS (ESI) m/e 434 (M+H)$^+$, 432 (M−H)$^−$.

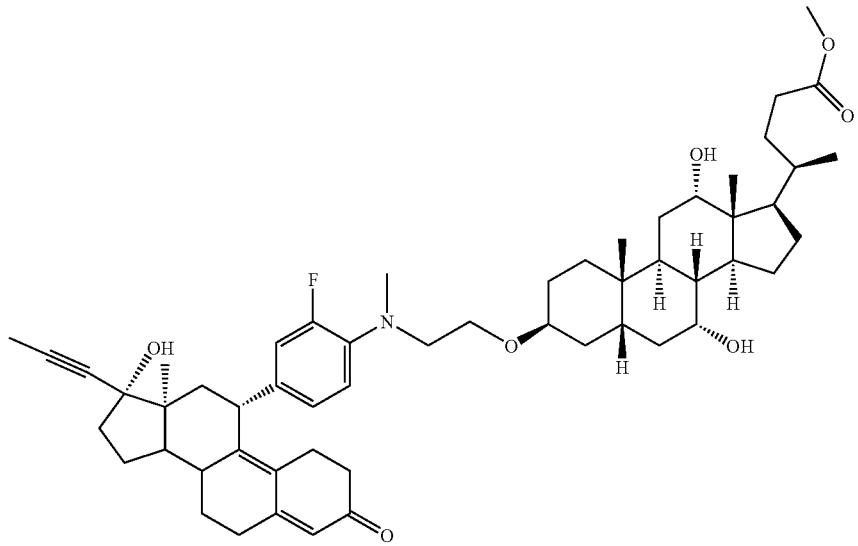

Exhibit 3D

Methyl (3β,5β,7α,12α)-7,12-dihydroxy-3-{2-[{4-[(11β,17α)-17-hydroxy-3-oxo-17-prop-1-ynylestra-4,9-dien-11-yl]-2-fluorophenyl}(methyl)amino]ethoxy}cholan-24-oic acid A mixture of the compound of Example 1C (79 mg, 0.13 mmol), the compound of Example 3C (55 mg, 0.13 mmol), diisopropylethylamine (25 mg, 0.193 mmol) and NaI (15 mg, 0.16 mmol) in CH₃CN (1.9 mL) in a sealed tube was heated at 115° C. for 40 hours. The reaction mixture was taken in EtOAc and washed with NH₄Cl solution and brine. The organic layer was dried over Na₂SO₄ and concentrated. The crude product was purified by silica gel chromatography (40% ethyl acetate/hexane) to provide the titled compound (68 mg, 61% yield). ¹H NMR (300 MHz, CDCl₃) δ 6.84-6.74 (m, 3H), 5.77 (s, 1H), 4.34 (d, J=6.9 HZ, 1H), 3.98 (m, 1H), 3.83 (m, 1H), 3.67 (s, 3H), 3.53-3.32 (m, 5H), 2.91 (s, 3H), 2.80-1.10 (m, 44H), 1.89 (s, 3H), 0.98 (d, J=6.3 Hz, 3H), 0.89 (s, 3H), 0.69 (s, 3H), 0.55 (s, 3 H); MS (ESI) m/e 882 (M+H)⁺, 880 (M−H)⁻.

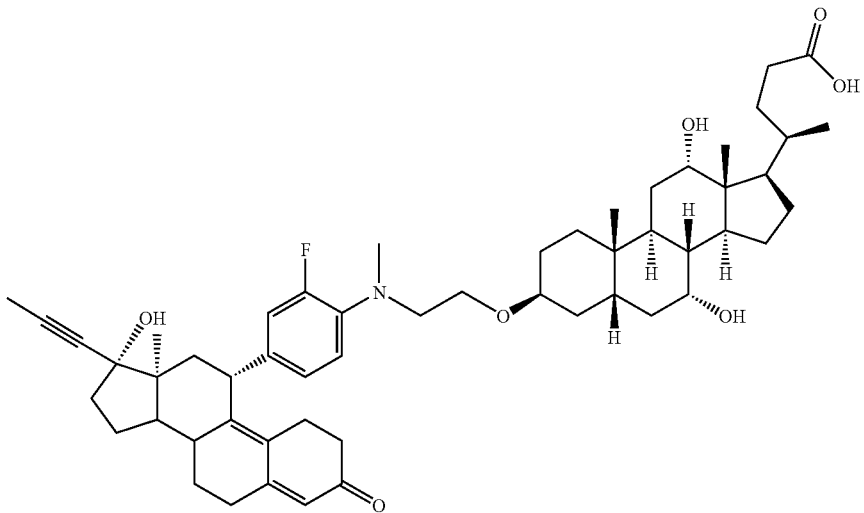

Example 3E (3β,5β,7α,12α)-7,12-Dihydroxy-3-{2-[{4-[(11β,17α)-17-hydroxy-3-oxo-17-1-ynylestra-4,9-dien-11-yl]-2-fluorophenyl}(methyl)amino]ethoxy}cholan-24-oic acid The compound of Example 3D (360 mg, 0.408 mmol) was dissolved in 6 ml of THF and CH₃OH (1:1). Then 2.5 ml of LiOH solution (1M, aqueous) was added at 0° C. The resulting mixture was stirred for 5 hour at ambient temperature. The organic solvent was removed in vacuo, and enough water was added to make one phase. The solution was acidified with acetic acid to precipitate a light yellow solid, which was extracted with EtOAc (3 times). The combined organic layer was washed with brine and dried over Na₂SO₄. Concentration in vacuo gave the title compound (350 mg, 98% yield). ¹H NMR (300 MHz, CDCl₃) δ 6.83-6.74 (m, 3H), 5.78 (s, 1H), 4.34 (d, J=7.2 Hz, 1H), 3.98 (m, 1H), 3.84 (m, 1H), 3.52-3.33 (m, 5H), 2.92 (s, 3H), 2.80-1.10 (m, 44H), 1.89 (s, 3H), 0.99 (d, J=6.0 Hz, 3H), 0.89 (s, 3H), 0.69 (s, 3H), 0.55 (s, 3H); MS (ESI) m/e 868 (M+MH)⁺, 866 (M−H)⁻.

Example 4

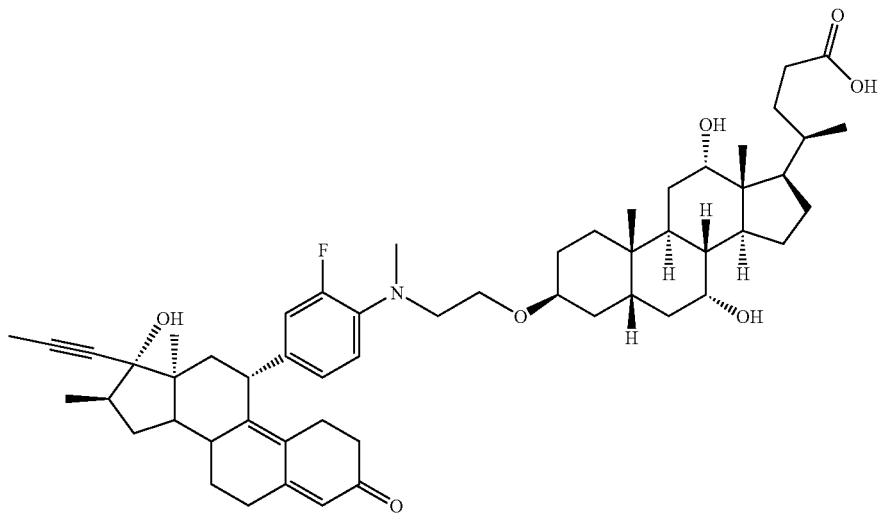

(3β,5β,7α,12α)-7,12-Dihydroxy-3-{2-[{4-[17β-hydroxy-16α-methyl-3-oxo17α-prop-1-ynylestra-4,9-dien-11β-yl]phenyl}(methyl)amino]ethoxy}cholan-24-oic acid Example 4A

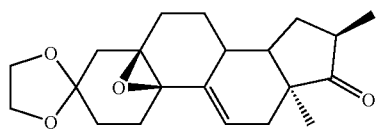

(5'R,10'R,13'S,16'R)-13',16'-dimethyl-1',2',6',7',8',12',13',14',15'-nonahydro-17'H-spiro[1,3-dioxolane-2,3'-[5,10]epoxycyclopenta[a]phenanthren]17'-one The compound of Example 1E (3.0 g, 9.1 mmol) was dissolved in 30 mL THF, cooled to −78° C. To the cooled solution was added LiHMDS (1.0 M in THF, 9.5 mL) and the resulting mixture was stirred for 1 hour at −78° C. MeI (6.0 mL, 91 mmol) was added rapidly via syringe and the solution was warmed to room temperature over 20 minutes. The reaction was quenched with the addition of aqueous NH₄Cl and extracted twice with ethyl acetate. The combined organics were washed with brine, dried (MgSO₄) and concentrated in vacuo to provide 3.03 g (97%) of the title compound, which was used without further purification.

Example 4B

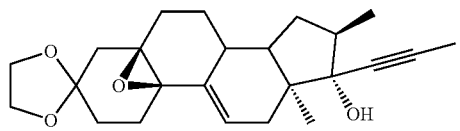

(5'R,10'R,13'S,16'R,17'S)-13',16'-dimethyl-17'-prop-1-ynyl-1',2',7',8',12',13',14',15',17'-nonahydro-6'H-spiro[1,3-dioxolane-2,3'-[5,10]epoxycyclopenta[a]phenanthren]-17'-ol The compound described in Example 4A (3.03 g, 8.80 mmol) was dissolved in THF (35 mL) and cooled to 0° C. Propynylmagnesiumbromide (0.5 M in THF, 35 mL) was added in one portion. The reaction mixture was stirred for 2.5 hour at 0° C. Upon completion, the reaction was quenched with aqueous NH₄Cl and extracted with ethyl acetate. The organic fraction was washed with brine, dried (MgSO₄) and concentrated in vacuo. The crude residue was purified by column chromatography (70:30 hexanes:ethyl acetate) to provide 1.0 g (29%) of the title compound.

Example 4C

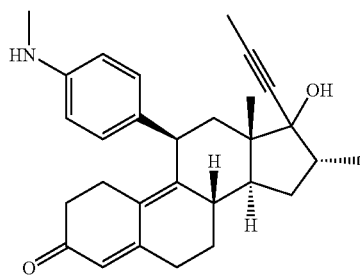

(11β,16α,17α)-17-hydroxy-16-methyl-11-(4-(methylamino)phenyl)-17-prop-1-ynylestra-4,9-dien-3-one Rieke Mg (1.0 M in THF, 13 mL) was added to a flame-dried three-necked round-bottom flask (fitted with a reflux condenser, glass stopper and rubber septum) along with 20 mL THF. The compound described in Example 1D (1.86 g, 6.50 mmol) was then added dropwise. After the addition of a small portion of the bromide, the flask was heated with a heat gun until the reaction initiated. The remaining bromide was added in portions, allowing for the reaction mixture to come to reflux and then cool. Upon completion of addition, the reaction solution cooled to room temperature and then was cooled in an ice bath. CuI (1.23, 6.50 mmol) was added in one portion. After 2 minutes, a solution of the compound described in Example 4B (1.0 g, 2.6 mmol) in 6 mL THF was added rapidly. After stirring at 0° C. for 1 hour, the reaction was quenched with aqueous NH$_4$Cl and extracted with ethyl acetate. The organic extracts were washed with brine, dried (MgSO$_4$) and concentrated. The crude residue was dissolved in 7.6 mL THF and 6 mL CH$_2$Cl$_2$. To that solution was added TsOH (3.8 g, 19.9 mmol) and the resulting solution was stirred at room temperature for 3 h. Sat. aq. NaHCO$_3$ was added to neutralize the reaction and the resulting solution was extracted with ethyl acetate. The organic extracts were washed with brine, dried (MgSO$_4$) concentrated and purified by column chromatography (70:30 hexanes:ethyl acetate). The title compound was isolated in 34% yield (250 mg).

Example 4D

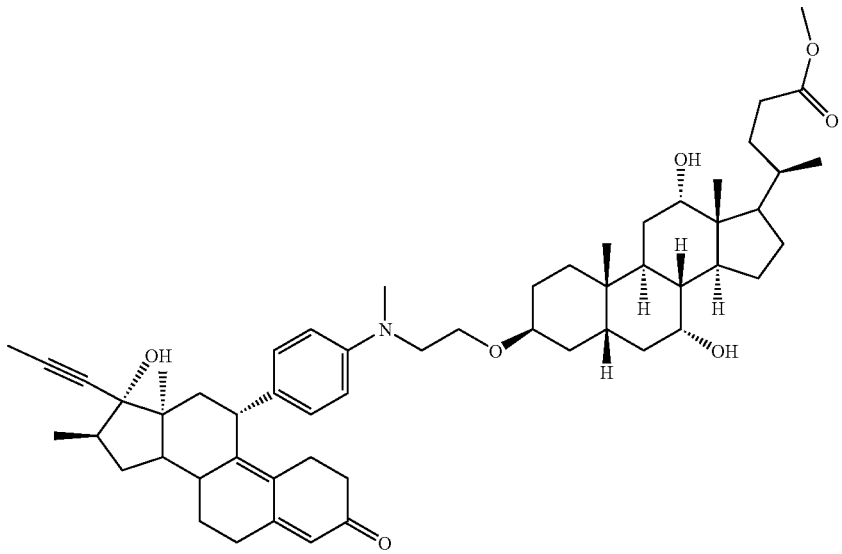

Methyl (3β,5β,7α,12α)-7,12-dihydroxy-3-{2-[4-[(11β,16α,17α)-17-hydroxy-16-methyl-3-oxo-17-prop-1-ynylestra-4,9-dien-11-yl]phenyl}(methyl)amino]ethoxy}cholan-24-oate In a pressure tube, the aniline described in Example 4C (250 mg, 0.581 mmol) was combined with the tosylate of Example 1C (361 mg, 0.581 mmol) and dissolved in 8 mL acetonitrile. To that solution was added NaI (104 mg, 0.696 mmol) and Hünig's base (0.2 mL, 0.873 mmol). The reaction mixture was stirred at 60° C. for 2 days. After cooling to room temperature, the solution was diluted with brine and extracted with ethyl acetate. The organic fraction was washed with brine, dried (MgSO$_4$) and concentrated in vacuo. The crude residue was purified by column chromatography (3:2 hexanes:ethyl acetate) to provide 215 mg (42% of the title compound.

Example 4E

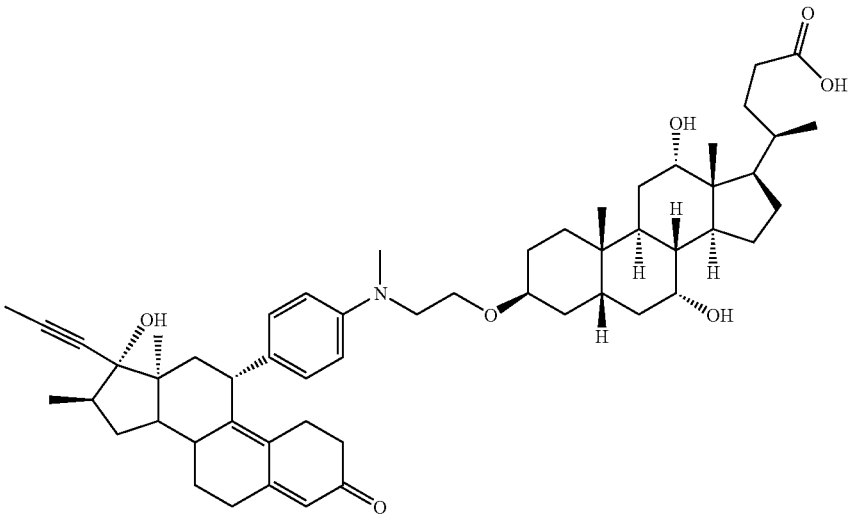

(3β,5β,7α,12α)-7,12-Dihydroxy-3-{2-[4-[(11β,16α,17α)-17-hydroxy-16-methyl-3-oxo-17-prop-1-ynylestra-4,9-dien-11-yl]phenyl}(methyl)amino]ethoxy}cholan-24-oic acid The compound described in Example 4D (215 mg, 0.244 mmol) was dissolved in 3 mL THF and 3 mL MeOH. An aqueous solution of LiOH (1.0 M, 1.0 mL) was then added and the resulting solution was stirred at room temperature for 3 hours. The alkaline solution was extracted once with $Et_2O$, acidified with 1N $H_3PO_4$ and extracted with ethyl acetate. The ethyl acetate fraction was dried with $Na_2SO_4$ and concentrated in vacuo. The while solid did not require further purification. $^1$H NMR (500 MHz, meOH) δ 7.07-7.71 (m, 4H), 5.76 (s, 1H), 4.4 (d, 1H), 3.95 (s, 1H), 3.78 (bs, 1H), 3.74 (5, 1H), 3.44 (m, 4H), 2.86 (m, 1H), 2.66 (m, 1H), 2.50 (m, 2H), 2.16-2.41 (m, 9H), 2.15 (m, 2H), 2.08 (m, 1H), 1.9 (m, 3H), 1.85 (m, 5H), 1.75 (m, 5H), 1.57 (m, 7H), 1.40 (m, 8H), 1.31 (m, 6H), 1.05 (d, 3H), 1.01 (d, 3H), 0.81 (s, 3H), 0.71 (s, 3H), 0.6 (s, 3H). MS (ESI) m/e 864 (M+H)$^+$, 863 (M−H)$^−$; Exact mass Calcd. for $C_{55}H_{78}NO_7$: 864.5769; found 864.5773.

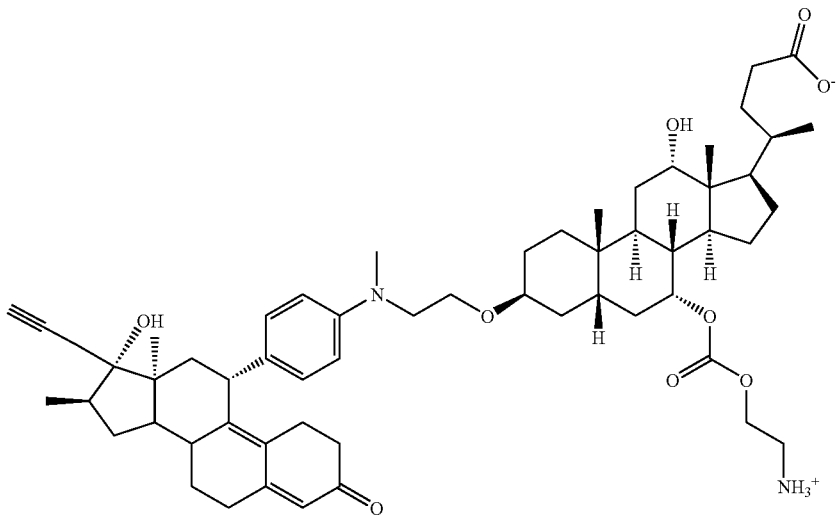

Example 5

(3β,5β,7α,12α)-7-[(2-ammonioethoxy)carbonyloxy]-12-hydroxy-3-{2-[{4-[(17β-hydroxy-3-oxo-17α-prop-1-ynylestra-4,9-dien-11β-yl]phenyl}(methyl)amino]ethoxyl cholan-24-oic acid

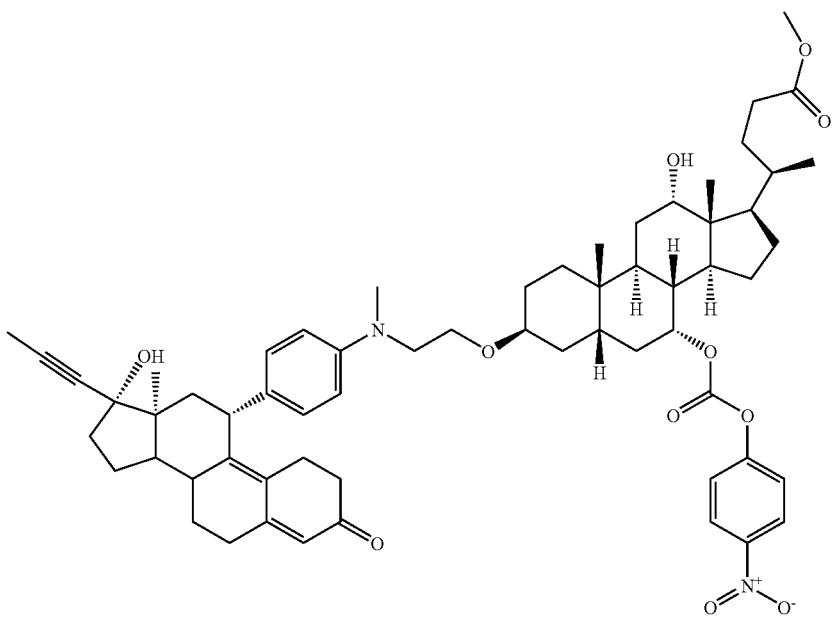

Example 5A

Methyl (3β,5β,7α,12α)-7-(4-nitrophenoxycarbonyloxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid To a well-stirred solution of the compound of Example 1I (1.20 g, 1.39 mmol) in pyridine (4.1 mL) at 0° C. was added 4-nitrophenylchloroformate (698 mg, 3.47 mmol) and warmed to room temperature overnight. The reaction mixture was partitioned between $H_3PO_4$ (1N) and EtOAc. The organic layer was dried over $Na_2SO_4$ and concentrated. The crude product was purified by silica gel chromatography (50% ethyl acetate/hexanes) to afford the title compound (0.70 g, 49% yield).

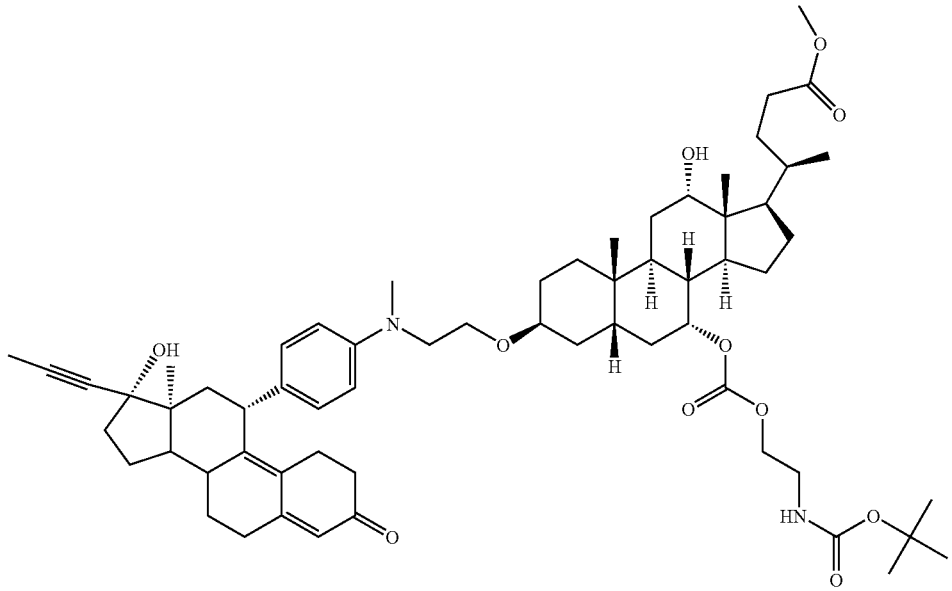

Example 5B

Methyl (3β,5β,7α,12α)-7-[2-(tert-butyloxycarbonylamino)ethoxycarbonyloxy]-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid A mixture of the compound of Example 5A (83 mg, 0.081 mmol), 2-(tert-butyloxy-carbonylamino)ethanol (26 mg, 0.161 mmol,) DMAP (10 mg) and Hunig's base (0.1 mL) in acetonitrile (1 mL) was stirred at 90° C. overnight. The reaction mixture was partitioned between $H_2O$ and EtOAc. The organic phase was dried over $Na_2SO_4$ and concentrated in vacuo. The residue was purified by silica gel chromatography (45% ethyl acetate/hexane) to give the title compound (73 mg, 86% yield).

Example 5C (3β,5β,7α,12α)-7-[(2-aminoethoxy)carboxy-12-hydroxy-3-{2-[{4-[11β,17β)-17-hydroxy-3-oxo-17-prop-1-ynylestra-4,9-dien-11-yl]phenyl}(methyl)amino]ethoxy}cholan-24-oic acid Added to a solution of HCl in 1,4-dioxane (4M, 0.3 mL) to the compound of Example 5B (20 mg, 0.019 mmol). The resultant mixture was stirred at room temperature for 6 hours. The reaction mixture was purified by HPLC (reverse phase) to afford the title compound (5 mg, 28% yield). $^1$H NMR (300 MHz, $CD_3OD$) δ 7.33-7.21 (m, 2H), 7.18-7.07 (m, 2H), 5.75 (s, 1H), 4.75 (m, 1H), 4.51 (d, J=7.2 Hz, 1H), 4.42-4.31 (m, 1H), 4.30-4.23 (m, 1H), 3.98 (m, 1H), 3.71-1.07 (m, 52H), 3.14 (s, 3H), 1.86 (s, 3H), 1.02 (d, J=6.6 Hz, 3H), 0.93 (s, 3H), 0.72 (s, 3 H), 0.51 (s, 3H); MS (ESI) m/e 937 (M+H)$^+$, 935 (M−H)$^-$.

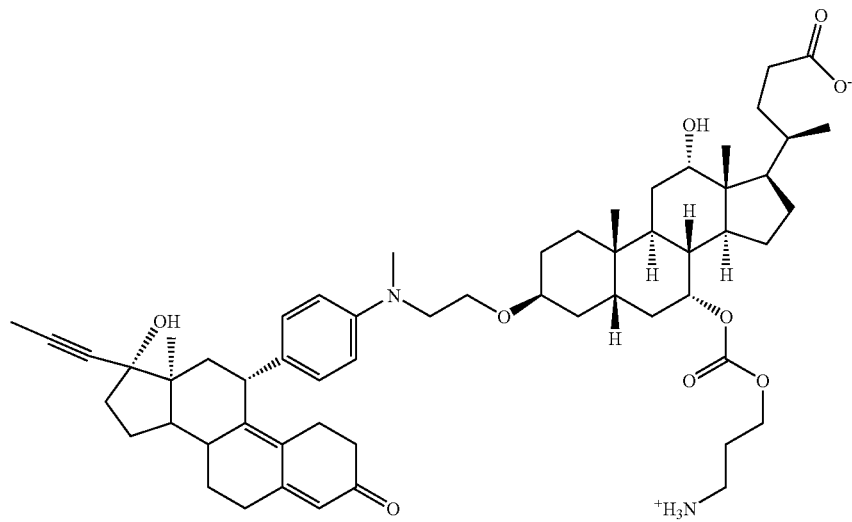
Example 6
(3β,5β,7α,12α)-7-[(3-ammoniopropoxy)carbonyloxy]-12-hydroxy-3-{2-[{4-[17β-hydroxy-3-oxo-17α-prop-1-ynylestra-4,9-dien-11β-yl]phenyl}(methyl)amino]ethoxy}cholan-24-oic acid
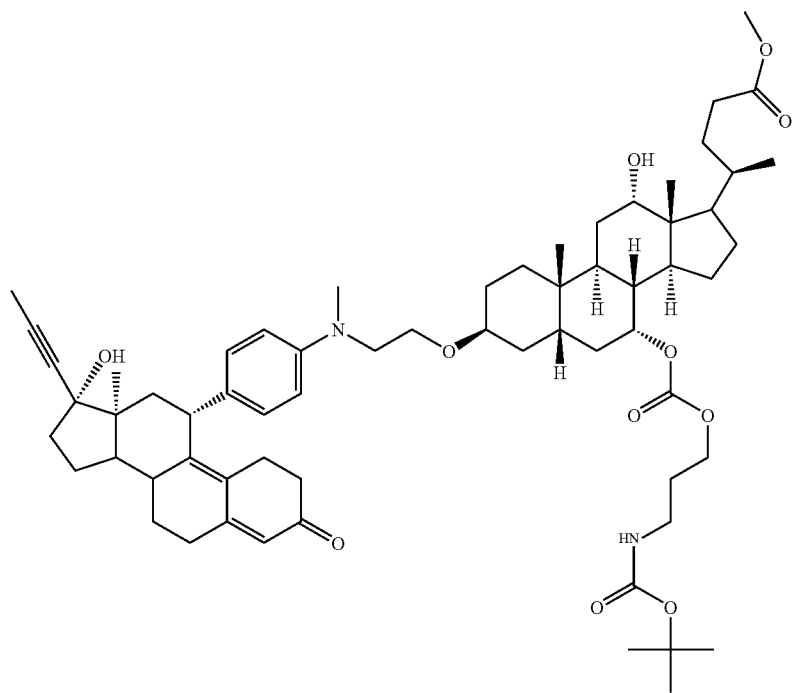

Example 6A

Methyl (3β,5β,7α,12α)-7-[3-(tert-butyloxycarbonyl)aminopropoxycarbonyloxy]-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The title compound was prepared by using the procedures of Example 5B, substituting 3-(t-butyloxycarbonylamino)propanol for 2-(t-butylcarbonylamino)ethanol (65%).

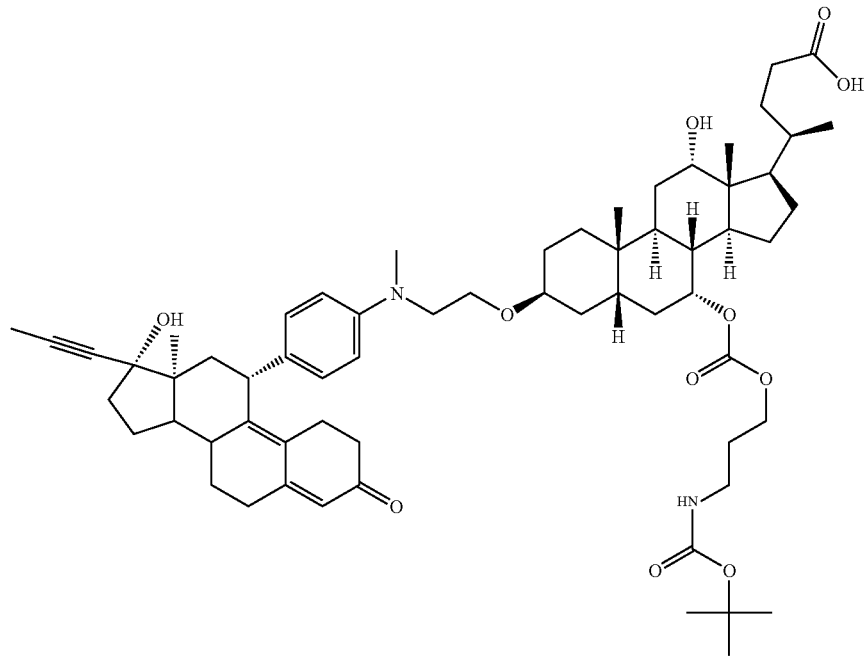

Example 6B (3β,5β,7α,12α)-7-[3-(tert-butyloxycarbonyl)aminopropoxycarbonyloxy]-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound 5 (46 mg, 0.043 mmol) was dissolved in 2.5 mL of THF and $CH_3OH$ (1:1.5). Then 0.8 ml of LiOH solution (1M, aqueous) was added at 0° C. The resulting mixture was stirred for overnight at ambient temperature. The organic solvent was removed in vacuo, and enough water was added to make one phase. The solution was acidified with $H_3PO_4$ (1 M) to precipitate a light yellow solid, which was extracted with EtOAc (2 times). The combined organic layer was washed with brine and dried over $Na_2SO_4$. Concentration in vacuo provided the title compound 6 (46 mg, 100% yield).

Example 6C (3β,5β,7α,12α)-7-[(3-ammoniopropoxy)carbonyloxy]-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid Added a solution of HCl in 1,4-dioxane (4M, 0.4 mL) to the compound of Example 6B (24 mg, 0.023 mmol) at 0° C. The resultant mixture was stirred at 0° C. for 0.5 hour and then room temperature for 0.5 hour. The reaction mixture was purified by HPLC (reverse phase) to provide the title compound (5 mg, 23% yield). $^1$H NMR (300 MHz, $CD_3OD$) δ 7.46-7.36 (m, 4 H), 5.77 (s, 1H), 4.73 (m, 1H), 4.57 (d, J=6.8 Hz, 1H), 4.31-4.21 (m, 1H), 4.21-4.10 (m, 1 H), 3.98 (m, 1H), 3.82-1.06 (m, 54H), 3.24 (s, 3H), 1.86 (s, 3H), 1.02 (d, J=6.4 Hz, 3H), 0.95 (s, 3H), 0.73 (s, 3H), 0.49 (s, 3H); MS (ESI) m/e 951 (M+H)$^+$, 949 (M−H)$^-$.

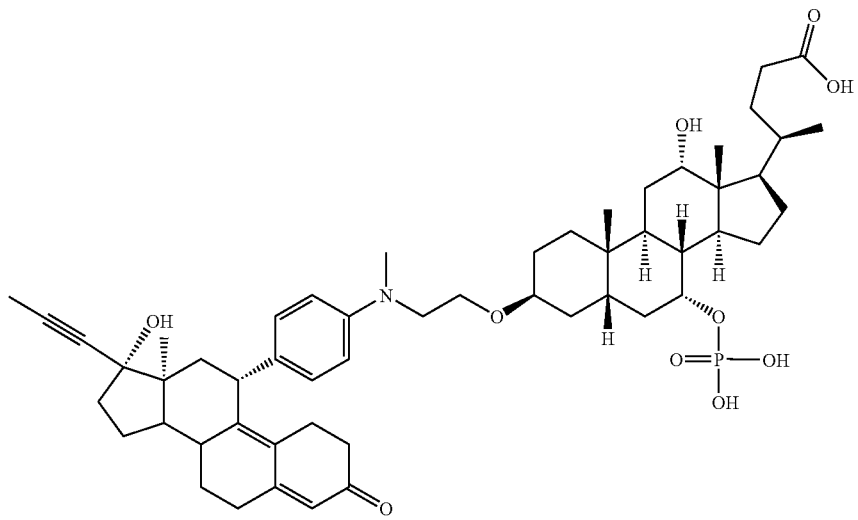

Example 7

(3β,5β,7α,12α)-7-Phosphoryloxy-12-hydroxy-3-{2-[{4-[17β-hydroxy-3-oxo-17α-prop-1-ynylestra-4,9-dien-11β-yl]phenyl}(methyl)amino]ethoxy}cholan-24-oic acid

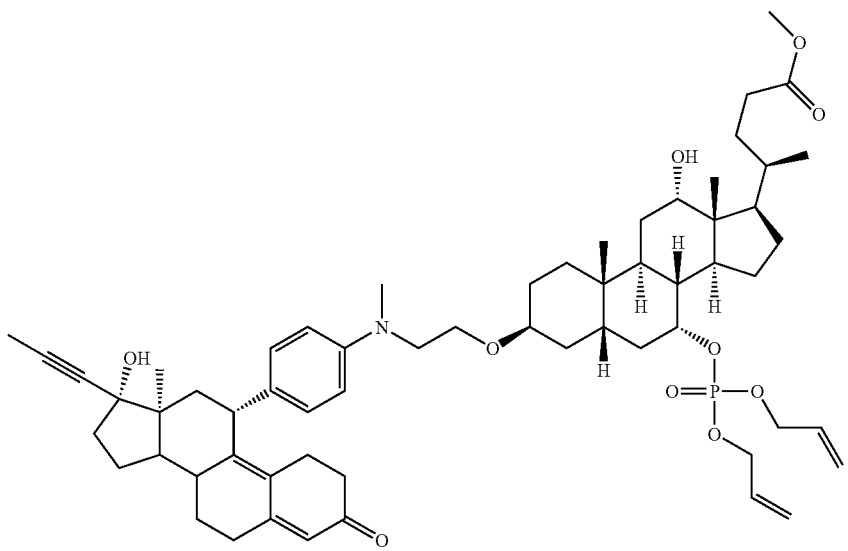

Example 7A

Methyl (3β,5β,7α,12α)-7-diallylphosphoriloxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 1I is dissolved in THF and cooled to 0° C. n-Butyllithium (2.5M solution in hexanes; 1.5 eq) is added dropwise; a white solid forms and disperses, and the solution turns light yellow. Diallyl phosphochloridate (2 eq) is added, causing a rapid discharge of the color; the solution is warmed slowly to ambient temperature and stirred overnight. The reaction is diluted with aqueous bicarbonate solution, and extracted with ethyl acetate. The organic layer is dried ($Na_2SO_4$), filtered, and concentrated in vacuo. The crude material is purified by column chromatography.

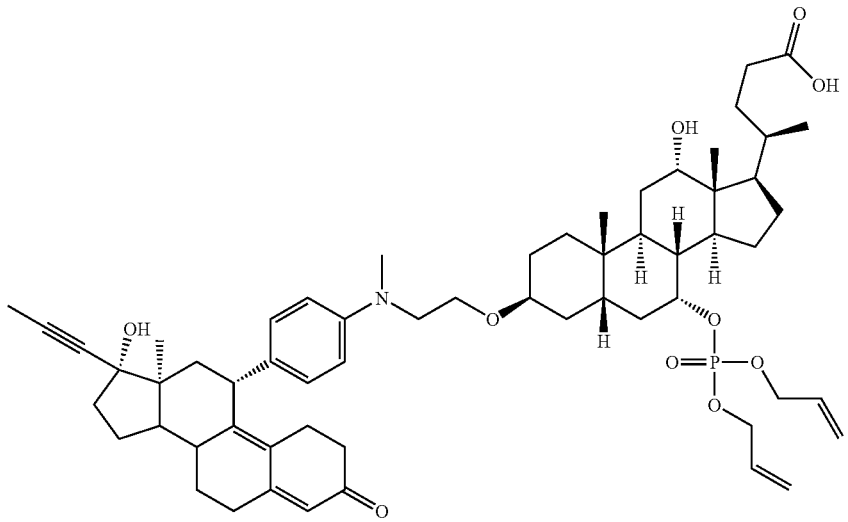

Example 7B (3β,5β,7α,12α)-7-Diallylphosphoryloxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 7A is dissolved in THF; an aqueous solution of LiOH is added, and the resultant mixture is stirred at ambient temperature for 3 hours. The reaction is quenched by addition of aqueous phosphoric acid (1N), and extracted with ethyl acetate. The combined organic layers were dried (NaSO₄), filtered, and concentrated under reduced pressure. The crude material is carried forward without further purification.

Example 7C (3β,5β,7α,12α)-7-Phosphoryloxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 7B is dissolved in THF; triphenylphosphine (0.5 eq), formic acid (2 eq), n-butylamine (2 eq), and tetrakis(triphenylphosphine)palladium(0) (0.3eq) are added, and the resultant mixture is stirred at ambient temperature for 3 hours. The solvents are removed in vacuo; the residue is taken up in aqueous 1N NaOH and extracted with dicholoromethane. The aqueous phase is acidified with aqueous phosphoric acid (1N); the product is purified by reverse-phase HPLC.

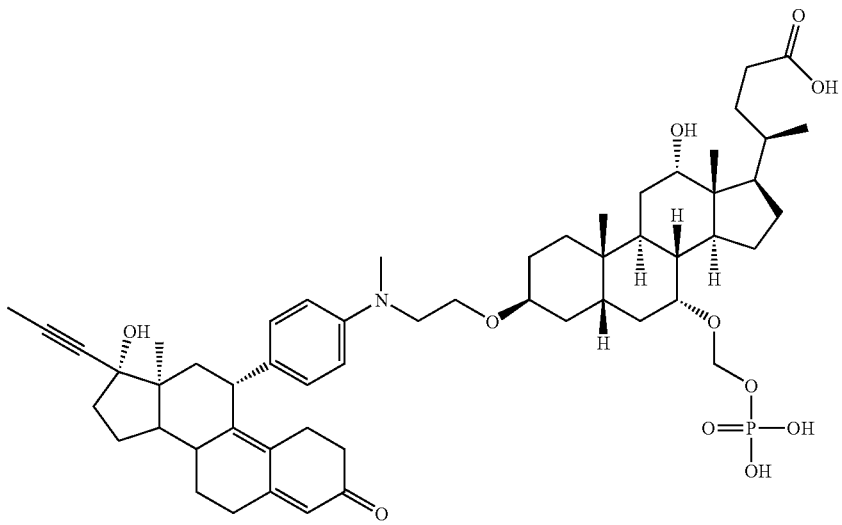

Example 8

(3β,5β,7α,12α)-7-Phosphoryloxymethoxy-12-hydroxy-3-{2-[{4-[17β-hydroxy-3-oxo-17α-prop-1-ynylestra-4,9-dien-11-yl]phenyl}(methyl)amino]ethoxy}cholan-24-oic acid

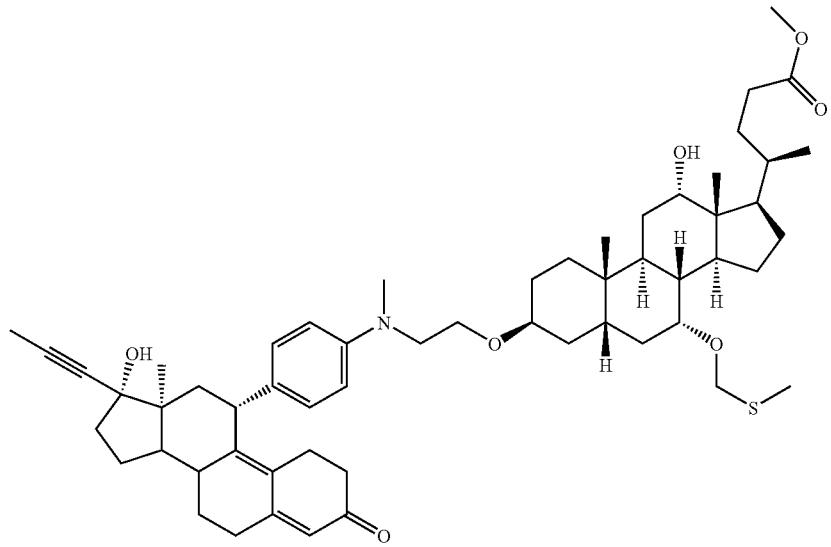

Example 8A

Methyl (3β,5β,7α,12α)-7-methylthiomethoxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 1I is dissolved in pyridine and cooled in an ice bath; methylthiomethyl chloride (1.2 eq) is added, and the mixture is warmed to ambient temperature, then heated to 90° C. overnight. The solvents are removed in vacuo; the residue is partitioned between aqueous phosphoric acid (1N) and ethyl acetate. The organic extract is washed with brine, dried ($Na_2SO_4$), filtered, and concentrated in vacuo. The crude material is purified by column chromatography.

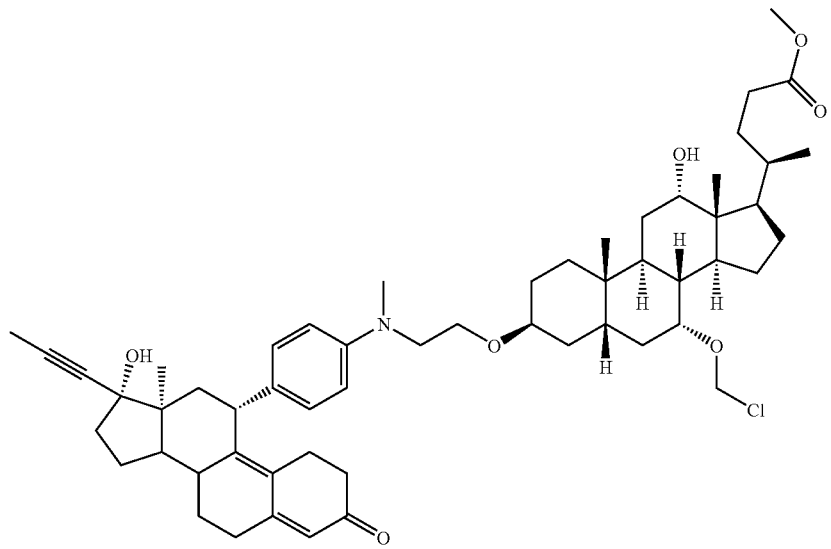

Example 8B

Methyl (3β,5β,7α,12α)-7-chloromethoxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8A is dissolved in dichloromethane; sulfuryl chloride (1.1 eq) is added, and the mixture is stirred at ambient temperature until starting material is consumed. The reaction is quenched by the addition of aqeous sodium bicarbonate; the organic layer is removed, and the aqueous phase is re-extracted with dichloromethane. The combined organic phases are dried (Na$_2$SO$_4$), filtered, and concentrated in vacuo. The crude material is used without further purification.

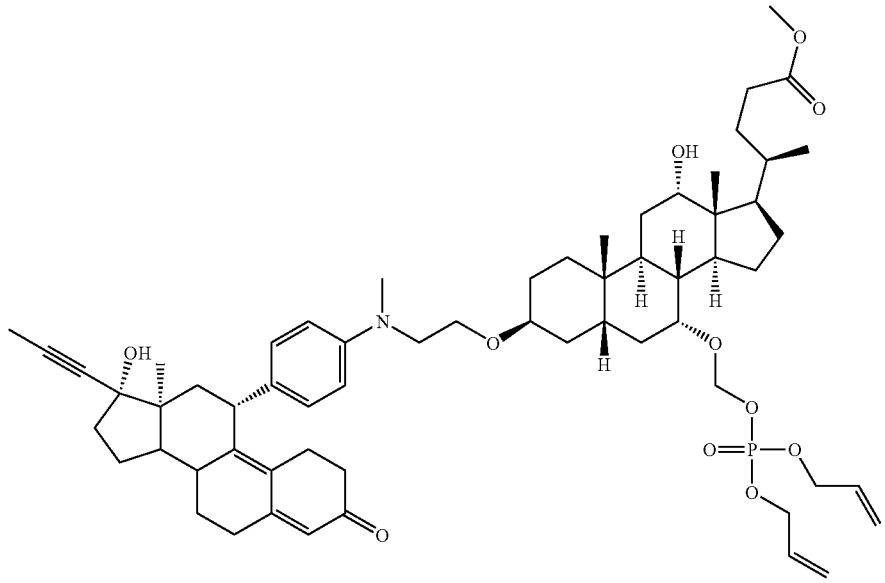

Example 8C

Methyl (3β,5β,7α,12α)-7-Diallylphosphoryloxymethoxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8B is dissolved in THF. Silver diallylphosphate is added, and the mixture is heated at reflux overnight. After cooling to ambient temperature, the crude reaction mixture is passed through a plug of silica gel to remove salts.

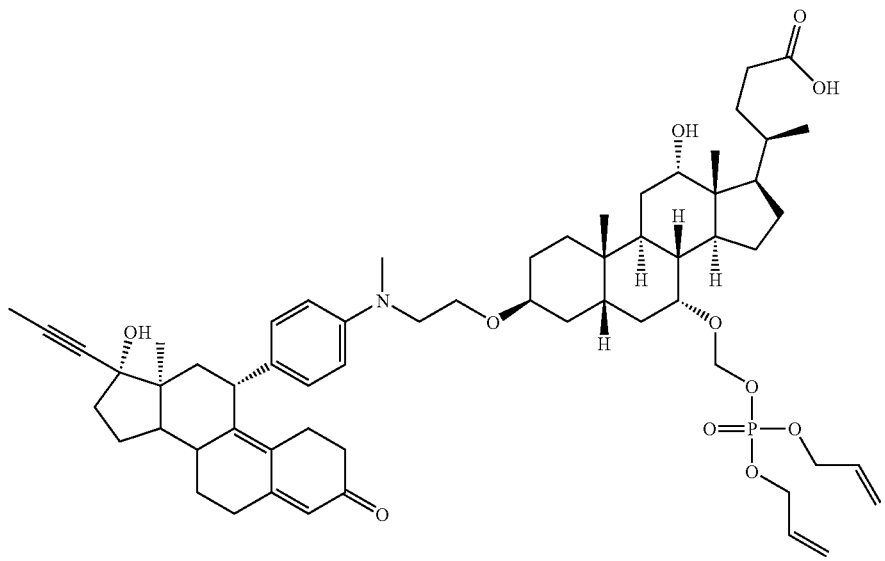

Example 8D (3β,5β,7α,12α)-7-Diallylphosphoryloxymethoxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8C is dissolved in THF; an aqueous solution of LiOH is added, and the resultant mixture is stirred at ambient temperature for 3 hours. The reaction is quenched by addition of aqueous phosphoric acid (1N), and extracted with ethyl acetate. The crude material is carried forward without further purification.

Example 8E (3β,5β,7α,12α)-7-Phosphoryloxymethoxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8D is dissolved in THF; triphenylphosphine (0.5 eq), formic acid (2 eq), n-butylamine (2 eq), and tetrakis(triphenylphosphine)palladium(0) (0.3 eq) are added, and the resultant mixture is stirred at ambient temperature for 3 hours. The solvents are removed in vacuo; the residue is taken up in aqueous 1N NaOH and extracted with dichloromethane. The aqueous phase is acidified with aqueous phosphoric acid (1N); the product is purified by reverse-phase HPLC.

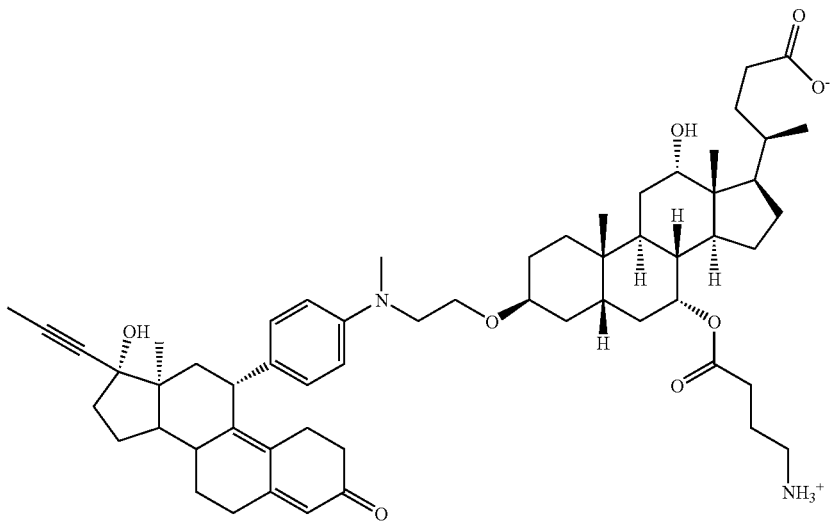

Example 9

(3β,5β,7α,12α)-7-(4-ammoniobutanoyloxy)-12-hydroxy-3-{2-[{4-[17β-hydroxy-3-oxo-17α-prop-1-ynylestra-4,9-dien-11β-yl]phenyl}(methyl)amino]ethoxyl cholan-24-oic acid

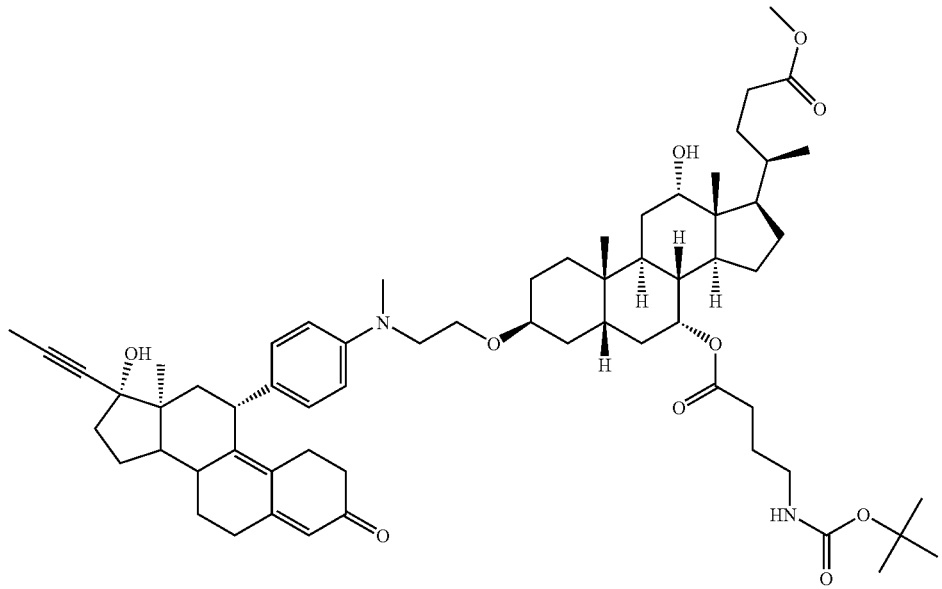

Example 9A

Methyl (3β,5β,7α,12α)-7-(4-tert-butoxycarbony-laminobutanoyloxy-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8B is dissolved in DMF; 4-tert-butoxycarbonylamino-butanoic acid (1.3 eq) is added, along with 1.2 equivalents of $Cs_2CO_3$. The resultant mixture is stirred overnight at ambient temperature. The reaction mixture is partitioned between aqueous phosphoric acid (1N) and ethyl acetate. The organic extract is dried ($Na_2SO_4$), filtered, and concentrated in vacuo. The crude material is purified on silica gel using a gradient of ethyl acetate in hexanes to provide the title compound.

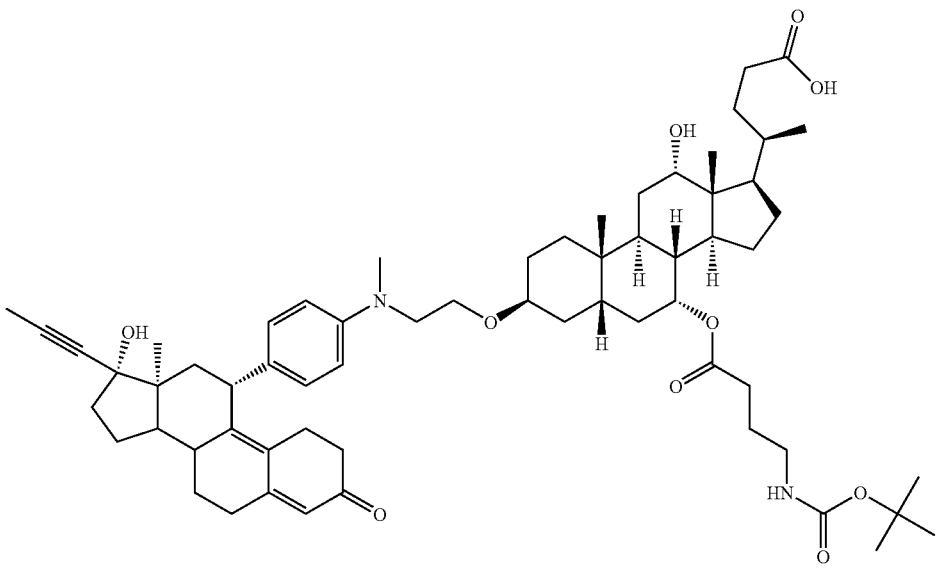

Example 9B (3β,5β,7α,12α)-7-(4-tert-butoxycarbonylaminobu-tanoyloxy-)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 9A is dissolved in THF; an aqueous solution of LiOH is added, and the resultant mixture is stirred at ambient temperature for 3 hours. The reaction is quenched by addition of aqueous phosphoric acid (1N), and extracted with ethyl acetate. The crude material is carried forward without further purification.

Example 9C (3β,5β,7α,12α)-7-(4-ammoniobutanoyloxy)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 9B is treated with a solution of HCl (4N) in dioxane. The resultant mixture is stirred at room temperature for 1 hour. The reaction mixture is purified by HPLC (reverse phase) to provide the title compound.

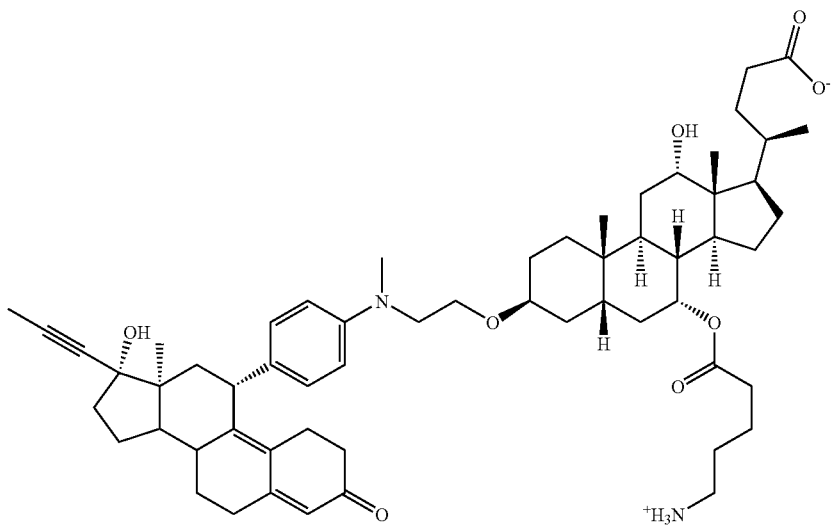
Example 10
(3β,5β,7α,12α)-7-(5-ammoniopentanoyloxy)-12-hydroxy-3-{2-[{4-[17β-hydroxy-3-oxo-17α-prop-1-ynylestra-4,9-dien-11β-yl]phenyl}(methyl)amino]ethoxy}cholan-24-oic acid
30
35
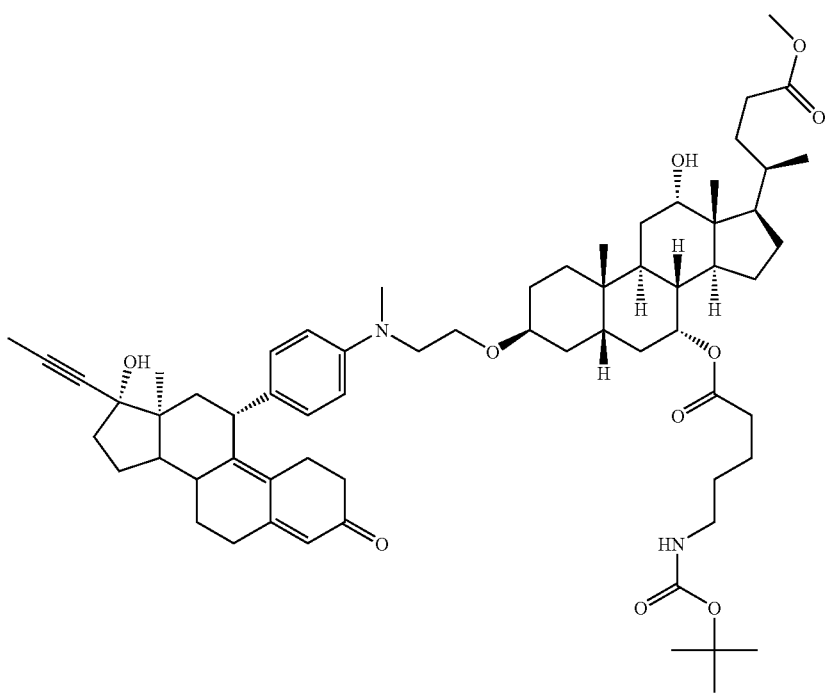

Example 10A

Methyl (3β,5β,7α,12α)-7-(5-tert-butoxycarbony-laminopentanoyloxy)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 8B is dissolved in DMF; 4-tert-butoxycarbonylamino-butanoic acid (1.3 eq) is added, along with 1.2 equivalents of $Cs_2CO_3$. The resultant mixture is stirred overnight at ambient temperature. The reaction mixture is partitioned between aqueous phosphoric acid (1N) and ethyl acetate. The organic extract is dried ($Na_2SO_4$), filtered, and concentrated in vacuo. The crude material is purified on silica gel using a gradient of ethyl acetate in hexanes to provide the title compound.

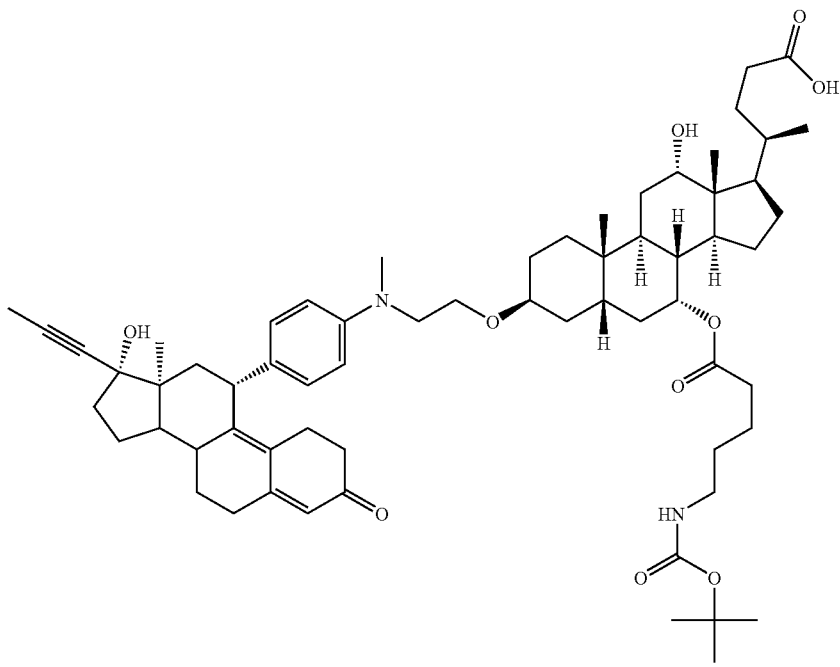

Example 10B (3β,5β,7α,12α)-7-(5-tert-butoxycarbonylaminopen-tanoyloxy)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 9A is dissolved in THF; an aqueous solution of LiOH is added, and the resultant mixture is stirred at ambient temperature for 3 hours. The reaction is quenched by addition of aqueous phosphoric acid (1N), and extracted with ethyl acetate. The crude material is carried forward without further purification.

Example 10C (3β,5β,7α,12α)-7-(5-ammoniopentanoyloxy)-12-hydroxy-3-{2-[{4-[(11β,17α)-17hydroxy-3-oxo-17-prop-1-ynylestra-4,9-dien-11-yl]phenyl}(methyl)amino]ethoxy}cholan-24-oic acid The compound of Example 9B is treated with a solution of HCl (4N) in dioxane. The resultant mixture is stirred at room temperature for 1 hour. The reaction mixture is purified by HPLC (reverse phase) to provide the title compound.

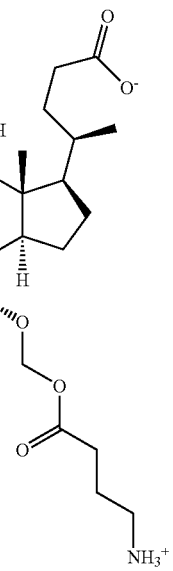

Example 11

(3β,5β, 7α,12α)-7-(4-ammoniobutanoy-
loxymethoxy)-12-hydroxy-3-{2-[{4-[17β-hydroxy-
3-oxo-17α-prop-1-ynylestra-4,9-dien-11-yl]phenyl}
(methyl)amino]ethoxy}cholan-24-oic acid

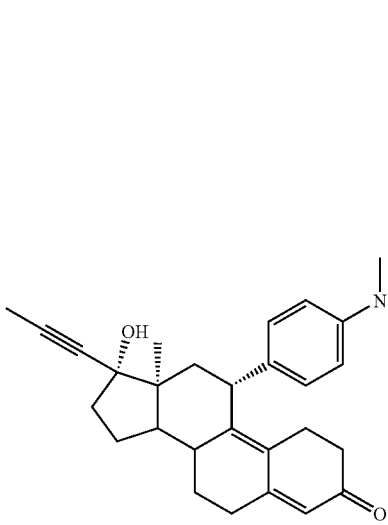

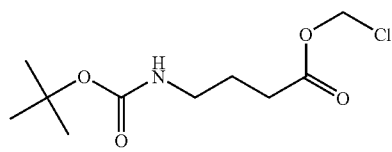

Example 11A 4-tert-butoxycarbonylaminobutanoic acid,
chloromethyl ester

4-N-tert-butoxycarbonylaminobutanoic acid (5 mmol) is dissolved in 20 mL of DMF; 10 mmol of triethylamine and 20 mmol of chloroiodomethane are added, and the resultant solution is stirred for 24 hrs at ambient temperature. The reaction mixture is partitioned between ethyl acetate and water; the organic layer is washed with water and brine. The resultant solution is dried (Na₂SO₄), filtered, and concentrated in vacuo. The crude material is purified on silica gel using a gradient of ethyl acetate in hexanes to provide the title compound.

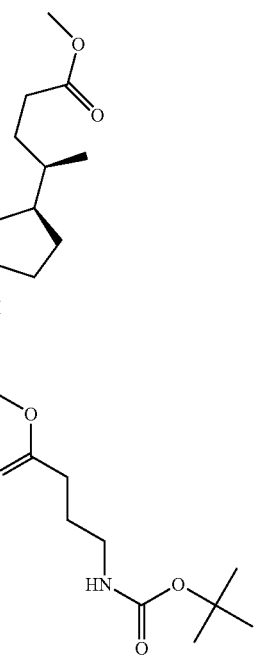

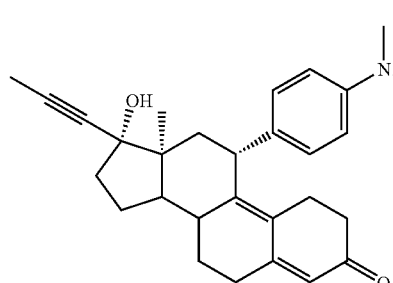

Example 11B

Methyl (3β,5β,7α,12α)-7-(4-tert-butoxycarbonylaminobutanoyloxymethoxy)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 1I (1 mmol) is combined with an equimolar amount of the compound of Example 11 A in 1 mL of acetonitrile. Diisopropylethylamine (2 eq) and NaI (20 mg) are added, and the resultant mixture is heated at 90° C. for 20 hrs. The reaction mixture is partitioned between ethyl acetate and water; the organic extract is washed with brine, dried (Na2SO₄), filtered, and concentrated in vacuo. The crude material is purified on silica gel using a gradient of ethyl acetate in hexanes to provide the title compound.

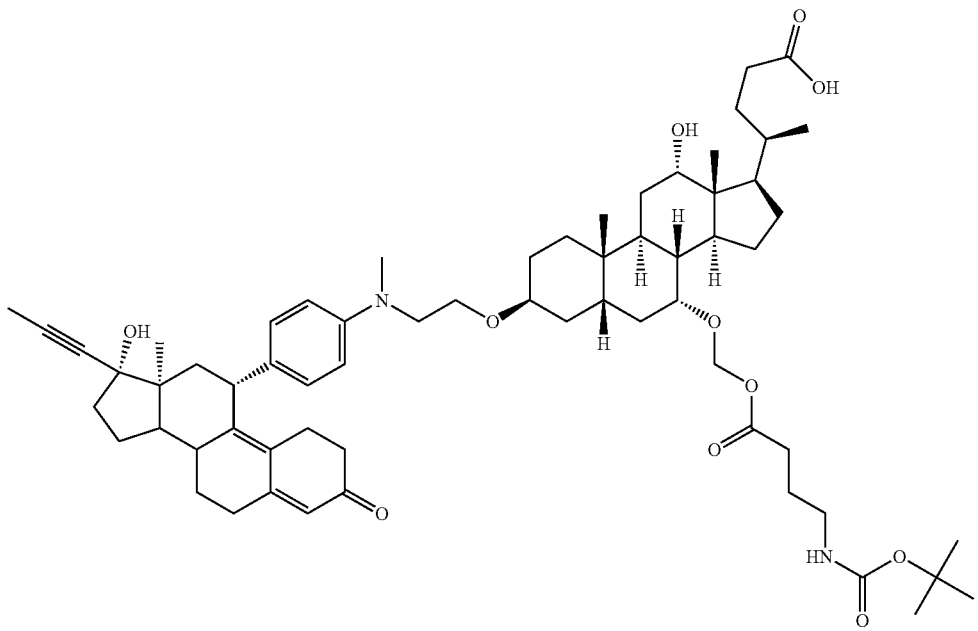

Example 11C (3β,5β,7α,12α)-7-(4-tert-Butoxycarbonylaminobutanoyloxymethoxy)-12-hydroxy-3-{2-[{4-[(11β,17α)-17-hydroxy-3-oxo-17-prop-1-ynylestra-4,9-dien-11-yl]phenyl}(methylamino]ethoxy}cholan-24-oic acid The compound of Example 11B is dissolved in THF; an aqueous solution of LiOH is added, and the resultant mixture is stirred at ambient temperature for 3 hours. The reaction is quenched by addition of aqueous phosphoric acid (1N), and extracted with ethyl acetate. The crude material is carried forward without further purification.

Example 11D (3β,5β,7α,12α)-7-(4-ammoniobutanoyloxymethoxy)-12-hydroxy-3-{2-[{4-[(11β,17α)-17-hydroxy-3-oxo-17-prop-1-ynylestra-4,9-dien-11-yl]phenyl}(methyl)amino]ethoxy}cholan-24-oic acid The compound of Example 11C is treated with a solution of HCl (4N) in dioxane. The resultant mixture is stirred at room temperature for 20 min. The reaction mixture is purified by HPLC (reverse phase) to provide the title compound.

Biological Data

One strategy for obtaining liver selective compounds is to conjugate them with a bile acid such as cholic acid. This strategy has been recently reviewed by Kramer and Wess (Kramer, W.; Wess, G.; "Bile acid transport systems as pharmaceutical targets"; *Eur. J. Clin. Invest.* 1996, 26, 715-732). For example, bile acid conjugates have been prepared with the thyroid hormone $T_3$ and with HMG-CoA reductase inhibitors. Both classes of conjugates were shown to reduce serum cholesterol levels while minimizing undesirable peripheral effects. These results demonstrate that bile acid conjugates can sometimes be liver selective and capable of delivering therapeutically useful concentrations of drug to the liver. An intriguing aspect of bile acid conjugates is that they are absorbed from the intestinal tract, excreted into the bile, and re-absorbed multiple times. Therefore bile acids can represent an extremely efficient sustained release delivery mechanism. However, bile acid conjugates must be carefully designed. Linkage sites on both the parent drug and the bile acid must be chosen to allow each to bring the desired properties to the linked species. A linker must be selected and attached to the parent drug molecule so as to retain an appropriate level of the desired biochemical activity (for example, enzymatic activity or receptor binding affinity) and selectivity. Similarly, the bile acid component must be selected and a linker attached in a manner that allows the bile acid to direct the conjugate selectively to the liver. In addition, in order to produce an orally-deliverable agent, the overall properties of the resultant conjugate must be optimized to allow uptake across the intestinal lumen, through either or a combination of active (transporter-mediated) and passive (diffusion) mechanisms.

EP0417725 describes bile acid derivatives for the treatment of various diseases. The derivatives in question have "a modified bile acid radical" attached, via a linker, to "an active compound moiety W, which is a peptide, an antibiotic, an antiviral substance, an anticancer agent, a hepatoprotective agent, an antilipidemic, a diuretic, a hypotensive, a renin inhibitor or a proline hydroxylase inhibitor." U.S. Pat. No. 5,780,444 describes a series of bile-acid conjugated nucleic acids as agents for transforming cells, and generically claims "a conjugate comprising a bile acid or its analog . . . covalently linked directly or indirectly to one or more second compounds". WO9944616 describes modified bile acids as antibiotic agents. One of the allowed modifications is "a linking group attached to a second steroid". These examples, along with the research summarized in the review of Kramer and Wess, all indicate that a bile acid conjugation strategy may lead to agents with selective activity in the liver. None, however, teaches how such a strategy might be implemented in the specific case where the active drug agent is a glucocorticoid antagonist. In fact, the factors which contribute to the development of an orally-deliverable and hepatoselective glucocorticoid antagonist are not obvious, as is summarized in the examples reported in Table I.

TABLE I

Effect of Bile Acid-Conjugate Steroids on Hepatic and Systemic Glucocorticoid Responses

| Compound | Inhibition of GR-mediated responses | | |
|---|---|---|---|
|  | TAT | Glycogen | Lymphocytes |
| RU-38486 | 100% | 74% | 108% |
| Compound 1 | 85% | 111% | 35% |
| Compound A | 39% | 9% | 9% |
| Compound B | 11% | 20% | 4% |
| Compound C | No inhibition | No inhibition | 14% |
| Compound D* | 22% | No inhibition | 8% |

All compounds dosed at 100 mpk orally in rats, except *Compound D, dosed subcutaneously at 23 mpk.

The analysis of both in vivo activity and liver selectivity may be accomplished using a single pharmacology study, involving a prednisolone challenge administered to rats. Prednisolone is a ubiquitously-distributed glucocorticoid agonist, and as such it demonstrates GR-agonist effects in both hepatic and extra-hepatic compartments. Administration of a 10 mg-per-kg (10 mpk) dose of prednisolone to normal rats leads to a 3-fold induction of the glucocorticoid-regulated enzyme tyrosine aminotransferase (TAT) during the course of a 7-hour experiment. At the same time, the agonist triggers an ~60%-increase in the deposition of hepatic glycogen. Both of the effects are believed to be mediated through direct activation of hepatic GR; the results of such experiments are demonstrated in FIG. 1.

Systemic glucocorticoid activity leads to an anti-inflammatory response, which is the result of a GR-linked suppression of lymphocytic activity. In practice, the prednisolone challenge protocol described above leads to a decrease in circulating lymphocyte levels in normal rats (results summarized in FIG. 2). Thus, the prednisolone challenge study allows for an internally-controlled evaluation of in vivo hepatic and systemic GR activation; and it provides an assay to determine the selective ability of any GR antagonist compound to block hepatic responses (a desirable trait) without effecting systemic glucocorticoid receptors (an undesired side effect).

RU-38486 is a prototype GR antagonist which is widely distributed throughout the body upon oral administration, and which demonstrates effects in a variety of tissue types. In the rat prednisolone challenge experiment, RU-38486 completely blocks the agonist effect on TAT induction at a dose of 30 mpk orally (Table I). In the same experiment, the prednisolone-induced deposition of hepatic glycogen is completely suppressed as well. Thus, RU-38486 has the desired profile of an orally-active agent to block hepatic glucocorticoid receptor. However, this agent also has effects in extra-hepatic compartments, as indicated by its ability to block the lymphopenic response produced by prednisolone in this same experiment. These extrahepatic effects make RU-38486 an unlikely candidate for long-term therapy.

A variety of conjugate molecules have been prepared by linking GR antagonists to bile acids (see FIG. 1 for representative structures). These compounds can be evaluated for in vivo activity and liver selectivity using the assay procedures described above. The compounds claimed herein are able to block the hepatic effects of prednisolone in this rat challenge model, without having a significant effect on systemic activity. For example, the compound of Example 1 causes nearly-complete blockade of the pred-induced increases in both TAT activity and glycogen levels (85% and 111% respectively), with little change in the number of circulating lymphocytes (only a 35% blockade of the pred-induced suppression), when dosed orally at 100 mpk (Table I). This profile of liver-selective antagonism is expected to be advantageous for long-term therapy, for example as would be required for the treatment of metabolic disorders like diabetes.

The specific details of chemical structure required to achieve an orally-deliverable, liver-selective agent for antagonizing glucocorticoid receptor, are not obvious. The Compound of Example 1 has three major components: a glucocorticoid antagonist-like fragment which confers the desired biochemical properties; a bile acid-like fragment which aids in targeting the conjugate to the hepatic compartment; and a linker fragment which not only must weld the other two components together to retain their individual activities, but also contributes to the overall physicochemical properties of the conjugate. Minor changes in any of these three components can unpredictably lead to a loss of this desirable pharmacological profile. For example, the bile acid component of the Compound of Example 1 can be switched from cholic acid to taurocholic acid, producing Compound A (FIG. 1). As expected, Compound A retains an affinity for GR similar to Compound 1 ($IC_{50}$ against human GR is 3.6 nM for Compound 1, 3.0 nM for Compound A). However, the pharmacologic activity (Table I) of the two compounds is quite distinct. Unlike Compound 1, this analog shows only a modest effect to inhibit TAT activation (39% inhibition at the same oral dose), and has essentially no effect on either the deposition of glycogen, or on the lymphopenic response. It is not selective for hepatic GR vs. systemic effects; in fact, it has minimal in vivo activity. Simple changes in the linker fragment, as demonstrated in Compounds B and C, can also lead to analogs that are not able to block hepatic glucocorticoid responses. This is true even in the most conservative case (as in Compound C) where the linker modifications do not result in a change in the attachment site on either the GR antagonist fragment or the bile acid fragment. These modest changes produce little effect on the affinity of the conjugate molecules for GR ($IC_{50}$ against human GR is 3.1 nM for Compound B, 4.3 nM for Compound C). Finally, a change in the choice of the specific GR antagonist that is targeted using this strategy, can have a significant effect on the properties of the conjugate molecule. RU-43044 is a steroidal GR antagonist with a potency ($IC_{50}$=2.2 nM against human GR) very similar to RU-38486 ($IC_{50}$=1.1 nM). RU-43044 may be linked to cholic acid in a fashion analogous to that described previously, to give Compound D. Compound D binds to GR with a potency similar to that of Compound 1 ($IC_{50}$=5.2 nM, vs 3.6 nM for Compound 1); but it is inactive in vivo and demonstrates no selectivity in the rat prednisolone challenge model. As the examples above demonstrate, the structural details leading to a compound with the desired liver-selective pharmacology are not easily discerned or predicted.

The systemic blockade of GR caused for example by RU-38486 treatment, would be expected to induce a compensatory response mediated through the hypothalamic-pituitary-adrenal (HPA) axis. Hypothalamic stimulation triggered by a suppressed systemic glucocorticoid leads to the secretion of adrenocorticotrophic hormone (ACTH) by the pituitary gland. ACTH acts on the adrenal gland to stimulate the production of endogenous glucocorticoids like cortisol (in man) or corticosterone (in rodents). In practice, an oral dose of RU-38486 produces increases in circulating levels of both ACTH and corticosterone in normal mice (see FIG. 3). A similar dose of the compound of Example 1 fails to stimulate the HPA axis, as evidenced by a lack of change in either of these parameters. This result confirms the result of the rat prednisolone challenge experiment, that Compound 1 demonstrates liver-selective pharmacology. It also provides additional evidence to suggest that Compound 1 might be able to lower glucose through hepatic GR blockade, without producing side effects resulting from HPA activation. Analogs like Compound 1 may thus have an improved efficacy and safety profile for the treatment of metabolic diseases like diabetes and obesity.

Methods for Radioligand Binding Studies with Human Glucocorticoid and Progesterone Receptor Cytosol $^3$(H)-dexamethasone (TRK 645) hereafter referred to as $^3$(H)-dex was purchased from Pharmacia Amersham, Uppsala, Sweden. Dexamethasone hereafter referred to as dex was purchased from SIGMA. The Costar 96-well polypropylene plates (3794 or 3365) were purchased from Life Technologies AB, Täby, Sweden. The GF/B filter (1450-521), filter cassette (1450-104), MeltiLex scintillating wax (1450-441), sample bag (1450-42), Microbeta™ 1450-PLUS and Microsealer 1495-021 were all purchased from Wallac Oy, Turkku, Finland. Human glucocorticoid receptors were extracted from Sf9 cells infected with a recombinant baculovirus transfer vector containing the cloned hGR genes. Recombinant baculovirus was generated utilizing the BAC-TO-BAC expression system (Life Technologies) in accordance to instruction from the supplier. The hGR coding sequences were cloned into a baculovirus transfer vector by standard techniques. The recombinant baculoviruses expressing hGR were amplified and used to infect Sf9 cells. Infected cells were harvested 48 hrs post infection. The receptors were extracted from the cell pellet with a phosphate buffer (1 mM EDTA, 20 mM $KPO_4$ (pH8), 8.6% Glycerol, 12 mM MTG, 20 mM $Na_2MoO_4$). The concentration of hGR in the extract was measured as specific $^3$(H)-dex binding with the G25-assay as described in J. Steroid Biochem. Molec. Biol. 50, No. 5/6, 313-318, 1994 and estimated to approximately 25 nM. The extract was aliquoted and stored at −70° C.

The filter binding assay: Dilution series of the test compounds and dexamethasone as reference were made from 10 mM (1 mM dex) stock solutions in DMSO. 10 µl of the dilutions was added in duplicates to the wells. The cell extracts were diluted 10 fold in EPMo+MTG buffer (1 mM EDTA, $HPO_4$ 20 mM (pH8), 6 mM MTG). The diluted extract was added to the wells (110µl). $^3$(H)-dex were diluted from the stock solution to 10-10.8 nM in EPMo+MTG buffer. 110µl of the diluted $^3$(H)-dex were added to the wells. The final concentration of hGR in the experiment was estimated to 1 nM. All preparations were made in ambient temperature (20-25° C.) on ice and with +4° C. temperated buffers. The plates were incubated overnight at +4° C. (15-20 hrs.).

The incubation was stopped by filtration through GF/B filter on the Tomtec Cellharvester. The filtration on the Tomtec Cellharvester was programmed as follows: 1) Preparation before filtration with EP buffer (1 mM EDTA 20 mM $HPO_4$ (pH8)) 2×(Wash/Asp 0.6 sec., Asp 0.5 sec.); 2) Prewet of GF/B filter with EP+PEI buffer (EP buffer, 0.3% Polyethylenimine) (Asp 0.8 sec.); 3) Filtration/harvesting of the 96-well incubation plate 3×(Wash/Asp 0.6 sec., Asp 0.5 sec.). The GF/B filter was dried for at least 1 hr at 65° C. A MeltiLex scintillation wax was melted onto the filter with the Microsealer. The filter was placed in a samplebag, which was thereafter trimmed with scissors to fit the filter cassette. The cassette were placed in the Microbeta and measured for 1 min/position, returning ccpm (corrected counts per minute).

For compounds able to displace the $^3$(H)-dexamethasone from the receptor an $IC_{50}$—value (the concentration required to inhibit 50% of the binding of $^3$(H)-dex was determined by a non-linear four parameter logistic model;

$$b=((b_{max}-b_{min})/(1+(I/IC_{50})^s))+b_{min}I$$

is added concentration of binding inhibitor, $IC_{50}$ is the concentration for inhibitor at half maximal binding and S is a slope factor.[1] For determinations of the concentration of $^3$(H)-dex in the solutions, regular scintillation counting in a Wallac Rackbeta 1214 was performed using the scintillation cocktail Superbix™ (Wallac).

[1] Haggblad, J., Carlsson, B., Kivelä, P., Siitari H., (1995) Biotechniques 18, 146-151

The Microbeta-instrument generates the mean cpm (counts per minute) value/minute and corrects for individual variations between the detectors thus generating corrected cpm values. It was found that the counting efficiency between detectors differed with less than five percent.

A similar protocol was employed to measure affinity of the compounds of the present invention for progesterone receptor (PR).

Compounds of the present invention demonstrate binding affinity for glucocorticoid receptor, and selectivity for GR over PR, as indicated below:

| Example # | GR Binding (IC$_{50}$, μM) | PR Binding ((IC$_{50}$, μM) |
|---|---|---|
| 1 | 0.0036 | 0.0087 |
| 2 | 0.0028 | 0.0023 |
| 3 | 0.0020 | 0.0045 |
| 4 | 0.0033 | 0.0016 |

Compounds of the present invention may be evaluated for their activity in vivo using the models described below. These same in vivo models may also be used to provide indication for the ability of certain compounds to block glucocorticoid action selectively in the liver.

Rat Prednisolone Challenge Model for Evaluation of Liver-Targeted Glucocorticoid Receptor Antagonists Overnight fasted 150 g male Sprague Dawley rats are orally dosed with vehicle, RU-486 (30-100 mg/kg), or selected glucocorticoid receptor antagonists (30-100 mg/kg), 60 minutes prior to an oral challenge with prednisolone at 10 mg/kg. Six hours following the prednisolone challenge, rats are euthanized with $CO_2$, and bled via cardiac puncture for evaluation of blood lymphocytes and plasma drug levels. 7 mm liver biopsy punches are harvested for evaluation of tyrosine aminotransferase (TAT), hepatic glycogen and GR antagonist levels. Additional liver tissue, retroperitoneal fat, skeletal muscle, kidney and skin from an ear biopsy are also removed for isolation an evaluation of mRNA. Prednisolone increases hepatic TAT and glycogen levels, and induces severe lymphopenia during the 6 hour challenge interval. At doses of 100 mpk, RU-486 completely antagonizes these hepatic and peripheral responses.

Compounds of the present invention demonstrate in vivo efficacy and hepatic selectivity in the above model, as demonstrated in Table 1.

Mouse Hypothalamic-Pituitary-Adrenal (HPA) Activation Model

Non-fasted CD-1 male mice, weighing approximately 25 g, are dosed with vehicle, RU-486 (30-100 mg/kg), or GR antagonist (30-100 mg/kg) at 0800 hr when corticosterone levels are low. Two hours later, mice are euthanized with $CO_2$, bled by cardiac puncture, and plasma analyzed for corticosterone by mass spectroscopy and for adrenocorticotropic hormone (ACTH) levels by ELISA. Brains and plasma are also removed for analysis of GR antagonist levels. At doses of 100 mpk, RU-486 significantly increases ACTH and corticosterone levels compared to vehicle controls. The present invention shows a reduced ability to stimulate the HPA axis as indicated in FIG. 3.

Compounds of the present invention may be used for the treatment of diseases associated with an excess of hepatic glucocorticoid response. Such diseases include but are not limited to the following: diabetes, obesity, Syndrome X, hyperglycemia, inadequate glucose clearance, hypertension, hyperinsulinemia, hyperlipidemia, or elevated hepatic glucocorticoid levels.

For the treatment of diabetes, Syndrome X, or hyperglycemia, compounds of the present invention may be used alone or in combination with any existing antidiabetic or antihyperglycemic agent. Agents which may used as part of such combination therapy include but are not limited to insulin, insulin mimetics such as mecasermin or the like, insulin secretagogues such as nateglinide, exendin, or the like, insulin sensitizers such as pioglitazone, rosiglitazone or the like, sulfonylureas such as glipizide, glyburide or the like, biguanides such as metformin, phenformin or the like, metiglinides such as repaglinide or the like, and α-glucosidase inhibitors such as acarbose, miglitol or the like. Other similar agents are known to one skilled in the art. The ability of the compounds of the present invention to treat diabetes, Syndrome X, or hyperglycemia, alone or in combination with another agent, can be demonstrated using the models and procedures described herein, or according to the methods of Friedman et al, in J. Biol. Chem. 1997, 272(50), 31475-31481. Other such methods for testing the efficacy of compounds of the present invention are known to one skilled in the art.

For the treatment of obesity, compounds of the present invention may be used alone or in combination with any existing antiobesity agent. Agents which may be used as part of such combination therapy include but are not limited to anorectic agents such as bromocryptine, dexfenfluramine and the like, monoamine reuptake inhibitors such as sibutramine and the like, sympathomimetics such as phentermine, phendimetrazine and the like, fatty acid uptake inhibitors such as orlistat or the like, and thyromimetics such as triiodothyronine or the like. Other such anti-obesity agents are known to one skilled in the art. The ability of compounds of the present invention to treat obesity, alone or in combination with another agent, can be demonstrated according to the models and procedures described by Langley and York, in Am. J. Physiol. 1990, 259 (Reg. Int. Comp. Phys. 28) R539-544, or by Walker and Romsos, in Am. J. Physiol. 1992, 262 (Endo. Metab. 25) E-110-117. Other such methods for testing the efficacy of compounds of the present invention are known to one skilled in the art.

For the treatment of inadequate glucose clearance or elevated hepatic glucocorticoid levels, compounds of the present invention may be used alone or in combination with any existing agent effecting glucose uptake or hepatic glucose production. Agents which may be used as part of such combination therapy include but are not limited to insulin, insulin mimetics such as mecasermin or the like, insulin secretagogues such as nateglinide, exendin, or the like, insulin sensitizers such as pioglitazone, rosiglitazone or the like, sulfonylureas such as glipizide, glyburide or the like, biguanides such as metformin, phenformin or the like, and metiglinides such as repaglinide or the like. Other such agents are known to one skilled in the art. The ability of compounds of the present invention to treat inadequate glucose clearance or elevated hepatic glucocorticoid response, alone or in combination with another agent, can be demonstrated according to the models and procedures described herein, or according to the methods of Terrettaz, Assimacopoulos-Jeannet, and Jeanrenaud, in Endocrinology. 1986, 118: 674-678. Other such methods for testing the efficacy of compounds of the present invention are known to one skilled in the art.

For the treatment of diabetic hypertension, compounds of the present invention may be used alone or in combination with any existing antihypertensive agent. Agents which may be used as part of such combination therapy include but are not limited to ACE inhibitors such as captopril, enanlipril, or the like, diuretics such as furosemide, hydrochlorothiazide, or the like, β-blockers such as atenolol, carvedilol, or the like, and calcium blockers such as amlodipine, nifedipine, or the like. Other such agents are known to one skilled in the art. The ability of compounds of the present invention to treat diabetic hypertension, alone or in combination with another agent, can be demonstrated according to the models and procedures described by Velasquez et al., in Hypertension 1997 (5), 1232-1237. Other such methods for testing the efficacy of compounds of the present invention are known to one skilled in the art.

For the treatment of hyperinsulinemia, compounds of the present invention may be used alone or in combination with any existing agent effecting insulin levels or insulin sensitivity. Agents which may be used as part of such combination therapy include but are not limited to insulin, insulin mimetics such as mecasermin or the like, insulin secretagogues such as nateglinide, exendin, or the like, and insulin sensitizers such as pioglitazone, rosiglitazone or the like. Other such agents are known to one skilled in the art. The ability of compounds of the present invention to treat hyperinsulinemia, alone or in combination with another agent, can be demonstrated according to the models and procedures described herein, or according to the methods of Shulman, et al., in Metabolism 1991, 40(10): 1025-1030; or according to the procedures described by Hevener, Reichart, and Olefsky, in Diabetes 2000, 49(12): 2154-2159. Other such methods for testing the efficacy of compounds of the present invention are known to one skilled in the art.

For the treatment of hyperlipidemia, compounds of the present invention may be used alone or in combination with any existing antihyperlipidemic agent. Agents which may be used as part of such combination therapy include but are not limited to niacin, statins such as lovastatin, simvastatin, or the like, fibrates such as fenofibrate, gemfibrozil, or the like, and bile acid sequestrants such as cholestyramine, colestipol, or the like. Other such agents are known to one skilled in the art. The ability of compounds of the present invention to treat hyperlipidemia, alone or in combination with another agent, can be demonstrated according to the models and procedures described by Olivier, et al., in Atherosclerosis 1988, 74 (1-2), 15-21. Other such methods for testing the efficacy of compounds of the present invention are known to one skilled in the art.

We claim:

1. A method of selectively antagonizing the effects of the glucocorticoid receptors in a mammal comprising administering a therapeutically effective amount of a compound of formula (I):

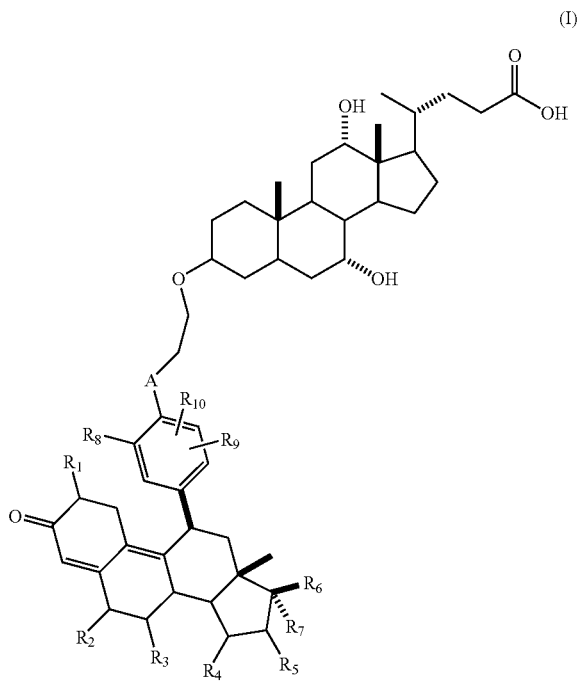

or a pharmaceutically suitable salt thereof, wherein

A is a member selected from the group consisting of —O— or $NR_A$ wherein $R_A$ is a member selected from the group consisting of hydrogen and alkyl;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, alkoxy, hydroxy, alkoxyalkyl, hydroxyalkyl, and halogen; and $R_8$, $R_9$ and $R_{10}$ are independently members selected from the group consisting of hydrogen, alkyl, alkenyl, alkynyl, alkoxy, hydroxy, cyano, halogen, and —$NR_BR_C$ wherein $R_B$ and $R_C$ are independently members selected from the group consisting of hydrogen and alkyl.

2. A method according to claim 1, wherein the glucocorticoid receptors are liver glucocorticoid receptors.

3. A method of regulation of metabolism in a mammal comprising administering a therapeutically effective amount of a compound of formula (I):

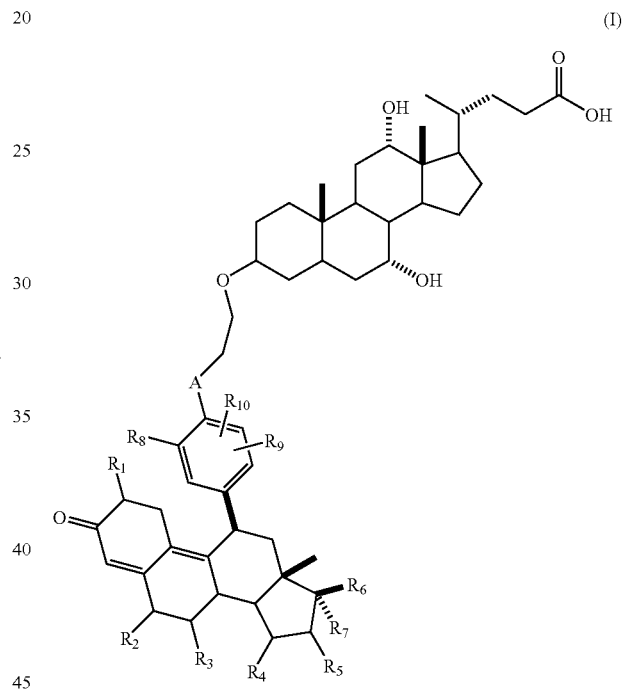

or a pharmaceutically suitable salt thereof, wherein

A is a member selected from the group consisting of —O— or $NR_A$ wherein $R_A$ is a member selected from the group consisting of hydrogen and alkyl;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, alkoxy, hydroxy, alkoxyalkyl, hydroxyalkyl, and halogen; and $R_8$, $R_9$ and $R_{10}$ are independently members selected from the group consisting of hydrogen, alkyl, alkenyl, alkynyl, alkoxy, hydroxy, cyano, halogen, and —$NR_BR_C$ wherein $R_B$ and $R_C$ are independently members selected from the group consisting of hydrogen and alkyl.

4. A method of lowering serum glucose levels and/or decreasing body weight in a mammal comprising administering a therapeutically effective amount of a compound of formula (I):

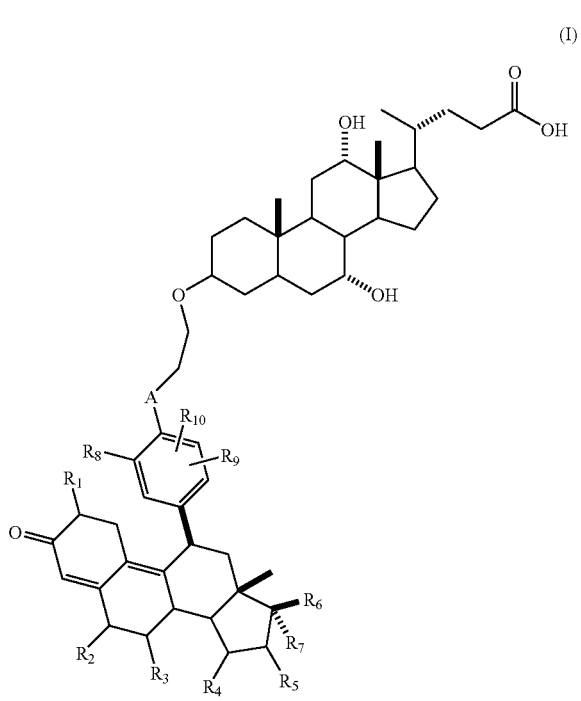

(I)

or a pharmaceutically suitable salt thereof, wherein
- A is a member selected from the group consisting of —O— or $NR_A$ wherein $R_A$ is a member selected from the group consisting of hydrogen and alkyl;
- $R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, alkoxy, hydroxy, alkoxyalkyl, hydroxyalkyl, and halogen; and
- $R_8$, $R_9$ and $R_{10}$ are independently members selected from the group consisting of hydrogen, alkyl, alkenyl, alkynyl, alkoxy, hydroxy, cyano, halogen, and $-NR_BR_C$ wherein $R_B$ and $R_C$ are independently members selected from the group consisting of hydrogen and alkyl.

5. A method of selectively antagonizing the effects of the glucocorticoid receptors in a mammal comprising administering a therapeutically effective amount of a compound of formula (II):

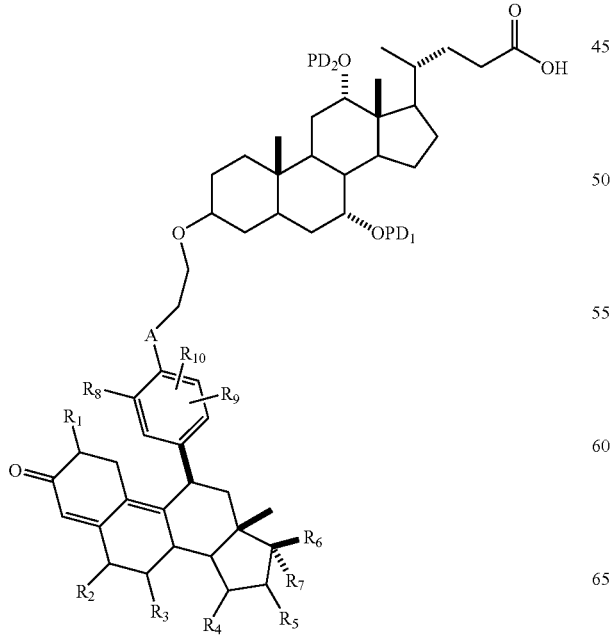

(II)

or a pharmaceutically suitable salt thereof, wherein
- A is a member selected from the group consisting of —O— and $-NR_A$;
- $R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, hydroxy, alkoxyalkyl, hydroxyalkyl, and halogen;
- $R_8$, $R_9$ and $R_{10}$ are independently members selected from the group consisting of hydrogen, alkyl, alkenyl, alkynyl, alkoxy, hydroxy, cyano, halogen and $-NR_BR_C$;
- $R_A$ is a member selected from the group consisting of hydrogen and alkyl;
- $R_B$ and $R_C$ are selected from the group consisting of hydrogen and alkyl; and
- one of $PD_1$ and $PD_2$ is a group such that the compound of formula (II) is selected from the group consisting of an ester, a phosphate, a phosphoryloxy-methyl carbonate, a carbamate, an acyloxymethyl ether, or a phosphoryloxymethyl ether, which are cleaved in vivo; and the other is as defined or is a hydrogen atom.

6. A method according to claim 5, wherein
one of $PD_1$ and $PD_2$ is selected from the group consisting of (2-ammonioethoxy)carbonyl, (3-ammoniopropoxy)carbonyl, phosphoryl, phosphoryloxymethyl, 4-ammoniobutanoyl, 5-ammoniopentanoyl, and 4-ammoniobutanoyloxymethyl; and the other is as defined or is a hydrogen atom.

7. A method according to claim 1, wherein the glucocorticoid receptors are liver glucocorticoid receptors.

8. A method of regulation of metabolism in a mammal comprising administering a therapeutically effective amount of a compound of formula (II):

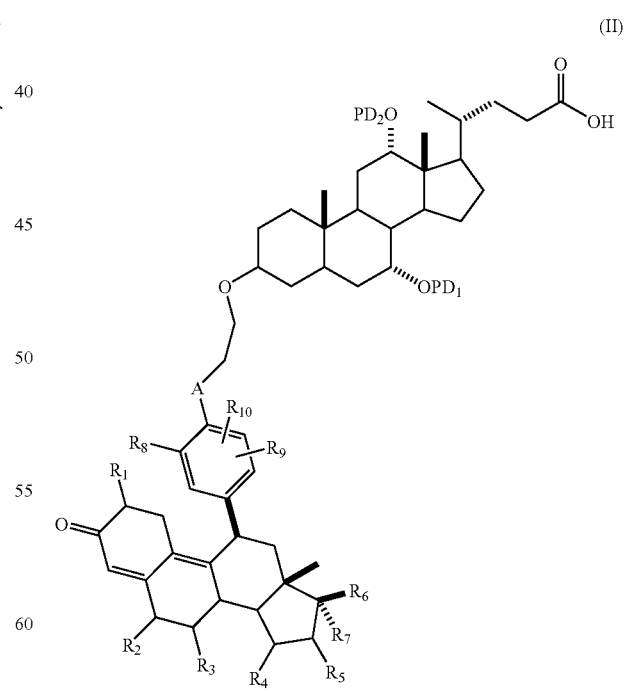

(II)

or a pharmaceutically suitable salt thereof, wherein
A is a member selected from the group consisting of —O— and $-NR_A$;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, hydroxy, alkoxyalkyl, hydroxyalkyl, and halogen;

$R_8$, $R_9$ and $R_{10}$ are independently members selected from the group consisting of hydrogen, alkyl, alkenyl, alkynyl, alkoxy, hydroxy, cyano, halogen and —$NR_BR_C$;

$R_A$ is a member selected from the group consisting of hydrogen and alkyl;

$R_B$ and $R_C$ are selected from the group consisting of hydrogen and alkyl; and one of $PD_1$ and $PD_2$ is a group such that the compound of formula (II) is selected from the group consisting of an ester, a phosphate, a phosphoryloxy-methyl carbonate, a carbamate, an acyloxymethyl ether, or a phosphoryloxy-methyl ether, which are cleaved in vivo; and the other is as defined or is a hydrogen atom.

9. A method of lowering serum glucose levels and/or decreasing body weight in a mammal comprising administering a therapeutically effective amount of a compound of formula (II):

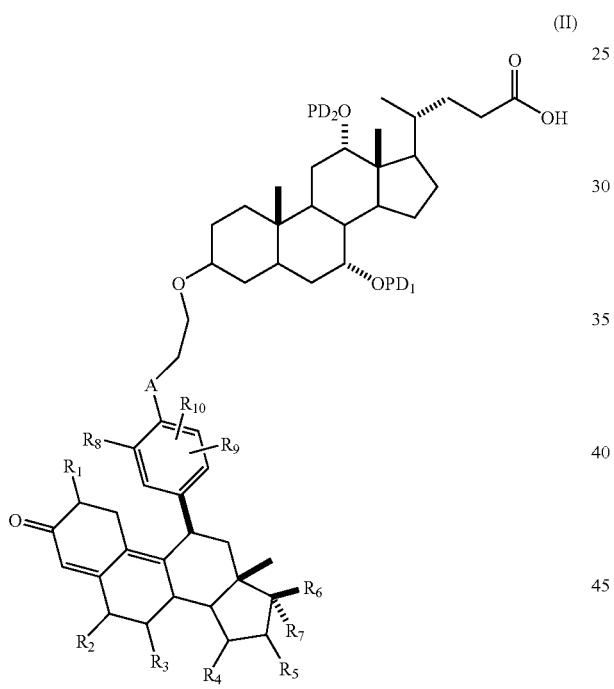

(II)

or a pharmaceutically suitable salt thereof, wherein
A is a member selected from the group consisting of —O— and —$NR_A$;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, hydroxy, alkoxyalkyl, hydroxyalkyl, and halogen;

$R_8$, $R_9$ and $R_{10}$ are independently members selected from the group consisting of hydrogen, alkyl, alkenyl, alkynyl, alkoxy, hydroxy, cyano, halogen and —$NR_BR_C$;

$R_A$ is a member selected from the group consisting of hydrogen and alkyl;

$R_B$ and $R_C$ are selected from the group consisting of hydrogen and alkyl; and one of $PD_1$ and $PD_2$ is a group such that the compound of formula (II) is selected from the group consisting of an ester, a phosphate, a phosphoryloxy-methyl carbonate, a carbamate, an acyloxymethyl ether, or a phosphoryloxy-methyl ether, which are cleaved in vivo; and the other is as defined or is a hydrogen atom.

10. A method according to claim 1, wherein the glucocorticoid recepters are liver glucocorticoid receptors.

11. A method of regulation of metabolism in a mammal comprising administering a therapeutically effective amount of a compound of formula (II):

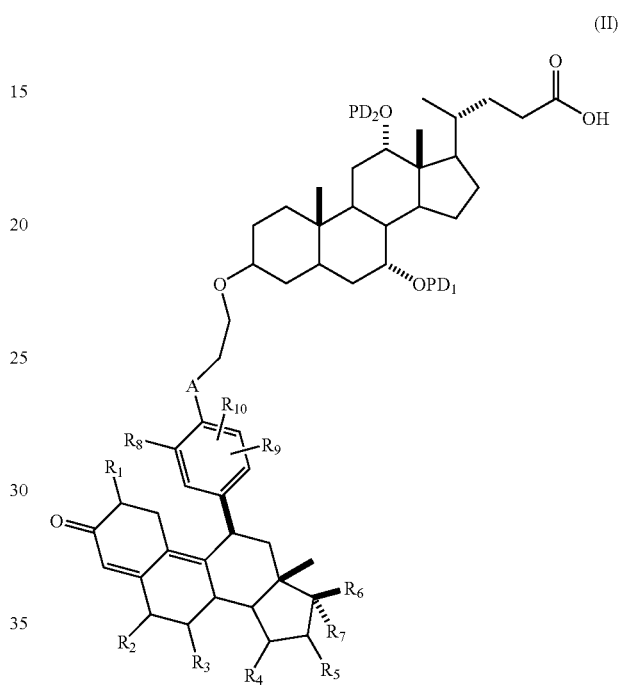

(II)

or a pharmaceutically suitable salt thereof, wherein
A is a member selected from the group consisting of —O— and —$NR_A$;

$R_1$, $R_2$, $R_3$, $R_4$, $R_5$, $R_6$ and $R_7$ are independently members selected from the group consisting of hydrogen, ($C_1$-$C_6$)-alkyl, alkenyl, alkynyl, hydroxy, alkoxyalkyl, hydroxyalkyl, and halogen;

$R_8$, $R_9$ and $R_{10}$ are independently members selected from the group consisting of hydrogen, alkyl, alkenyl, alkynyl, alkoxy, hydroxy, cyano, halogen and —$NR_BR_C$;

$R_A$ is a member selected from the group consisting of hydrogen and alkyl;

$R_B$ and $R_C$ are selected from the group consisting of hydrogen and alkyl; and one of $PD_1$ and $PD_2$ is selected from the group consisting of (2-ammonioethoxy) carbonyl, (3-ammoniopropoxy) carbonyl, phosphoryl, phosphoryloxymethyl, 4-ammoniobutanoyl, 5-ammoniopentanoyl, and 4-ammoniobutanoyloxymethyl; and the other is as defined or is a hydrogen atom.

12. A method of lowering serum glucose levels and/or decreasing body weight in a mammal comprising administering a therapeutically effective amount of a compound of formula (II):

(II)

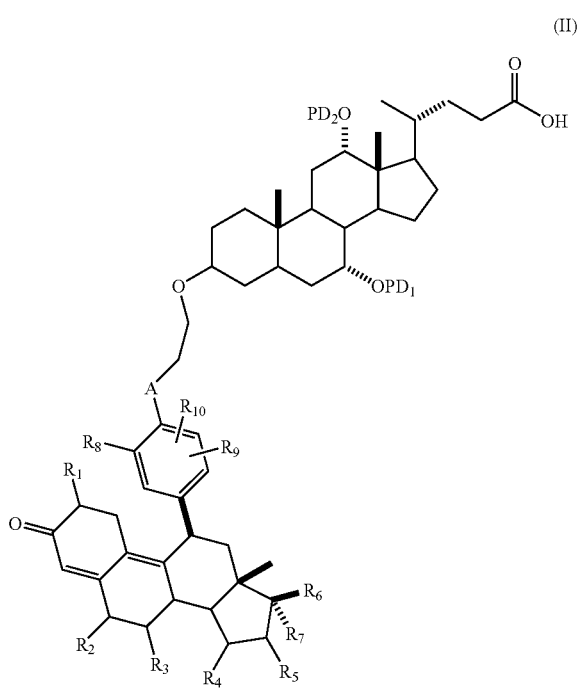

or a pharmaceutically suitable salt thereof, wherein

A is a member selected from the group consisting of —O— and —NR$_A$;

R$_1$, R$_2$, R$_3$, R$_4$, R$_5$, R$_6$ and R$_7$ are independently members selected from the group consisting of hydrogen, (C$_1$-C$_6$)-alkyl, alkenyl, alkynyl, hydroxy, alkoxyalkyl, hydroxyalkyl, and halogen;

R$_8$, R$_9$ and R$_{10}$ are independently members selected from the group consisting of hydrogen, alkyl, alkenyl, alkynyl, alkoxy, hydroxy, cyano, halogen and —NR$_B$R$_C$;

R$_A$ is a member selected from the group consisting of hydrogen and alkyl;

R$_B$ and R$_C$ are selected from the group consisting of hydrogen and alkyl; and one of PD$_1$ and PD$_2$ is selected from the group consisting of (2-ammonioethoxy) carbonyl, (3-ammoniopropoxy) carbonyl, phosphoryl, phosphoryloxymethyl, 4-ammoniobutanoyl, 5-ammoniopentanoyl, and 4-ammoniobutanoyloxymethyl; and the other is as defined or is a hydrogen atom.

\* \* \* \* \*

UNITED STATES PATENT AND TRADEMARK OFFICE
CERTIFICATE OF CORRECTION

PATENT NO.        : 7,521,439 B2                                  Page 1 of 1
APPLICATION NO.   : 11/491337
DATED             : April 21, 2009
INVENTOR(S)       : Richard D. Bishop et al.

It is certified that error appears in the above-identified patent and that said Letters Patent is hereby corrected as shown below:

On the cover page, item (75) "Jacobsen" should be "Jacobson".

Claim 2, line 13, "recepters" should be "receptors".

Claim 7, line 32, "recepters" should be "receptors".

Claim 10, line 5, "recepters" should be "receptors".

Claim 7, line 31, "1" should be "5".

Claim 10, line 4, "1" should be "6".

Signed and Sealed this

Twenty-first Day of July, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,521,439 B2                                    Page 1 of 1
APPLICATION NO. : 11/491337
DATED              : April 21, 2009
INVENTOR(S)        : Richard D. Bishop et al.

It is certified that error appears in the above-identified patent and that said Letters Patent is hereby corrected as shown below:

On the cover page, item (75) "Jacobsen" should be "Jacobson".

Column 96, Claim 2, line 13, "recepters" should be "receptors".

Column 98, Claim 7, line 31, "1" should be "5".

Column 98, Claim 7, line 32, "recepters" should be "receptors".

Column 100, Claim 10, line 4, "1" should be "6".

Column 100, Claim 10, line 5, "recepters" should be "receptors".

This certificate supersedes the Certificate of Correction issued July 21, 2009.

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

PATENT NO.         : 7,521,439 B2                                    Page 1 of 1
APPLICATION NO. : 11/491337
DATED              : April 21, 2009
INVENTOR(S)        : Richard D. Bishop et al.

It is certified that error appears in the above-identified patent and that said Letters Patent is hereby corrected as shown below:

At column 62, lines 11-33, the structural formula

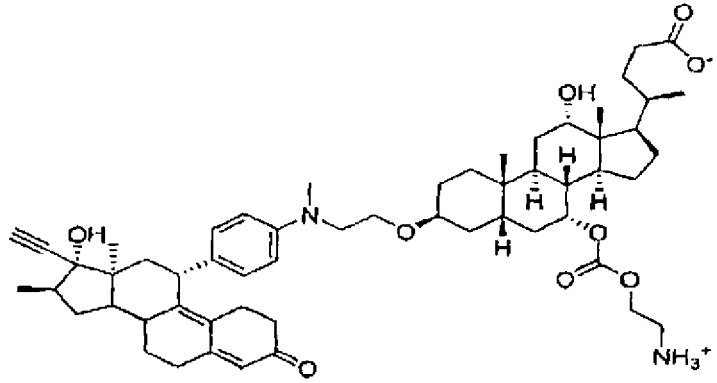

should be

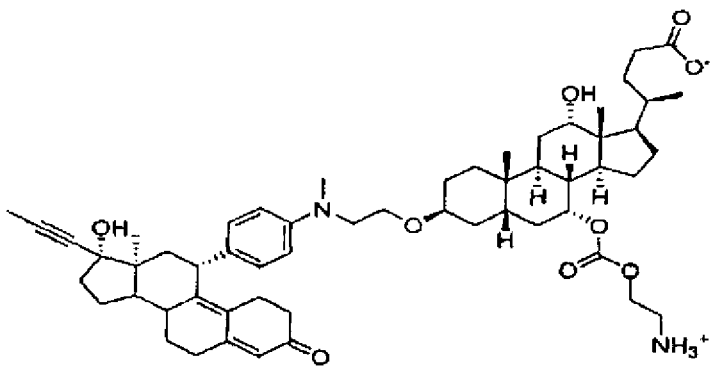

Signed and Sealed this

Twentieth Day of October, 2009

David J. Kappos
*Director of the United States Patent and Trademark Office*